(12) United States Patent
Niedernhofer et al.

(10) Patent No.: US 10,293,001 B2
(45) Date of Patent: *May 21, 2019

(54) COMPOSITIONS AND METHODS FOR RESTORING OR REJUVENATING STEM/PROGENITOR CELL FUNCTION

(71) Applicant: University of Pittsburgh—Of the Commonwealth System of Higher Education, Pittsburgh, PA (US)

(72) Inventors: Laura J. Niedernhofer, Juno Beach, FL (US); Mitra Lavasani, Chicago, IL (US); Paul D. Robbins, Juno Beach, FL (US); Johnny Huard, Houston, TX (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/051,754

(22) Filed: Feb. 24, 2016

(65) Prior Publication Data

US 2016/0243170 A1    Aug. 25, 2016

Related U.S. Application Data

(62) Division of application No. 13/912,927, filed on Jun. 7, 2013, now Pat. No. 9,295,696.

(60) Provisional application No. 61/657,104, filed on Jun. 8, 2012.

(51) Int. Cl.
| | |
|---|---|
| *A61K 35/34* | (2015.01) |
| *A61K 31/436* | (2006.01) |
| *A61K 38/17* | (2006.01) |
| *C12N 5/077* | (2010.01) |

(52) U.S. Cl.
CPC ............ *A61K 35/34* (2013.01); *A61K 31/436* (2013.01); *A61K 38/1709* (2013.01); *C12N 5/0658* (2013.01)

(58) Field of Classification Search
None
See application file for complete search history.

(56) References Cited

U.S. PATENT DOCUMENTS

| | | | |
|---|---|---|---|
| 5,538,722 | A  | 7/1996  | Blau et al. |
| 6,025,332 | A  | 2/2000  | Mascarenhas |
| 6,866,842 | B1 | 3/2005  | Chancellor et al. |
| 7,837,993 | B2 | 11/2010 | Conboy et al. |
| 7,906,110 | B2 | 3/2011  | Chancellor et al. |
| 9,295,696 | B2 | 3/2016  | Niedernhofer et al. |
| 2009/0175836 | A1 | 7/2009 | Brodsky |
| 2010/0081681 | A1 | 4/2010 | Blagosklonny |
| 2014/0010801 | A1 | 1/2014 | Niedernhofer et al. |
| 2016/0243170 | A1 | 8/2016 | Niedernhofer et al. |

FOREIGN PATENT DOCUMENTS

WO    WO-2011/109834 A2    9/2011

OTHER PUBLICATIONS

Tanaka (2003) "Regeneration: If They Can Do It, Why Can't We?" Cell, 113(5): 559-62.*
McCullagh (May 28, 2012) "Can a young muscle's stem cell secretome prolong our lives?", Stem Cell Research & Therapy, 3:19, pp. 1-3.*
Van Harten (1999) "Acute dystonia induced by drug treatment", BMJ, 319: 623 (printed from https://www.bmj.com/content/319/7210/623), 6 pages long.*
Acsadi et al. "A Differential Efficiency of Adenovirus-Mediated in vivo Gene Transfer Into Skeletal Muscle Cells of Different Maturity." Hum. Mol. Genet. 3.4(1994):579-584.
Ahrens et al. "Stage-Related Capacity for Limb Chondrogenesis in Cell Culture." Dev. Biol. 60.1(1977):69-82.
Andrews et al. "Monoclonal Antibody 12-8 Recognizes a 115-kd Molecule Present on both Unipotent and Multipotent Hematopoietic Colony-Forming Cells and Their Precursors." Blood. 67.3(1986):842-845.
Anonymous, (2016) 'Progeroid syndromes,' Wikipedia. Website: https://en.wikipedia.org/wiki/Progeroid_syndromes Accessed Feb. 29, 2016 (17 pages).
Anonymous, LAMIN A/C: LMNA, OMIM Entry #150330 LAMIN A/C LMNA. Website: <http://www.omim.org/entry/150330?search=hutchinsongilford%20progeria%20syndrome&highlight=syndrome%20hutchinsongilford%20syndr> . . . Accessed Feb. 29, 2016 (32 pages).
Anonymous, XFE Progeroid Syndrome: XFEPS. OMIM entry #610965 XFE Progeroid Syndrome: XFEPS. Website: <http://www.omim.org/entry/610965>. Accessed Feb. 29, 2016 (2 pages).
Ashman. "The Biology of Stem Cell Factor and Its Receptor C-Kit." Int. J. Biochem. Cell Biol. 31(1999):1037-1051.
ATCC "H9c2(2-1)(ATCCOCRL—1446th product sheet", available from company webpage, 2006.
Blanton et al. "Isolation of Two Populations of Myoblasts From Porcine Skeletal Muscle." Musc. Nerve. 22.1(1999):43-50.
Brunet et al. "Ageing: From Stem to Stern." Nature. 449.7160(2007):288-291.
Cavallini et al. "Evidence for Selective Mitochondrial Autophagy and Failure in Aging." Autophagy. 3.1(2007):26-27.
Chen et al. "mTOR Regulation and Therapeutic Rejuvenation of Aging Hematopoietic Stem Cells." Sci. Signal. 2.98(2009):ra75.

(Continued)

*Primary Examiner* — Robert M Kelly
(74) *Attorney, Agent, or Firm* — Goodwin Procter LLP

(57) ABSTRACT

This invention relates to the use of autologous stem/progenitor cells to restore or rejuvenate adult stem cell function in a mammal, wherein the restoration or rejuvenating extends lifespan and/or improves health of the mammal. In addition, the invention also relates to compositions containing one or more regulatory factors secreted or released from isolated mammalian stem/progenitor cells and use of such compositions to extend lifespan and/or improve health of a mammal. Also provided are methods of treating, delaying, preventing or reversing progeria or related syndromes in a mammal using isolated autologous or allogeneic stem/progenitor cells and/or regulatory factors secreted or released therefrom.

9 Claims, 31 Drawing Sheets

Specification includes a Sequence Listing.

(56) References Cited

OTHER PUBLICATIONS

Chen et al., (2008), 'TSC-mTOR Maintains Quiescence and Function of Hematopoietic Stem Cells by Repressing Mitochondrial Biogenesis and Reactive Oxygen Species,' J Exp Med, 205. 10(2008):2397-2408.
Civin et al. "Antigenic Analysis of Hematopoiesis. III. A Hematopoietic Progenitor Cell Surface Antigen Defined by a Monoclonal Antibody Raised against Kg-1a Cells." J. Immunol. 133.1(1984):157-165.
Deasy et al. "Effect of VEGF on the Regenerative Capacity of Muscle Stem Cells in Dystrophic Skeletal Muscle." Mol. Ther. 17.10(2009):1788-1798.
Dominiv et al. "Bcl-2 Expression Identifies an Early Stage of Myogenesis and Promotes Clonal Expansion of Muscle Cells." J. Cell Biol. 142.2(1998):537-544.
Esther Landuis, Jan. 6, 2012, http://www.alzforum.org/news/research-news/muscle-derived-stem-cells-slow- -aging-progeria-mouse-model, published by Alzforum, Cambridge, MA, no journal, no volume, no issue number, no pages, 8 pages long.
Faustman et al. "Prevention of Xenograft Rejection by Masking Donor HLA Class I Antigens." Science. 252.5013(1991)1700-1702.
Fina et al. "Expression of the CD34 Gene in Vascular Endothelial Cells." Blood. 75.12(1990):2417-2426.
Gan et al. "mTORC1 Signaling Governs Hematopoietic Stem Cell Quiescence." Cell Cycle. 8.7(2009):1003-1006.
Gharaibeh et al. "Isolation of a Slowly Adhering Cell Fraction Containing Stem Cells from Murine Skeletal Muscle by the Preplate Technique." Nat. Protoc. 3.9(2008)1501-1509.
Hands et al. "mTOR's Role in Ageing: Protein Synthesis or Autophagy?" Aging. 1.7(2009):586-597.
Harkema et al., (2016), 'Pathology of Mouse Models of Accelerated Aging,' Vet Pathol, Feb. 10 Issue (24 pages).
Helmholtz Association of German Research Centres, (2013), 'Rapamycin: Limited Anti-aging Effects,' Sci Daily, Jul. 25 issue, downloaded from <https://www.sciencedaily.com/releases/2013/07/130725141715.htm>.
Hirschfield G et al., (2007), 'Progeroid Syndromes, Clinical Symptoms and Molecular Causes of Premature Aging,' Stsch Artzebl, 104(6):A346-53.
Irintchev et al. "Expression Pattern of M-Cadherin in Normal, Denervated, and Regenerating Mouse Muscles." Dev. Dyn. 199. 4(1994):326-337.
Katagiri et al. "Bone Morphogenetic Protein-2 Converts the Differentiation Pathway of C2C12 Myoblasts into the Osteoblast Lineage." J. Cell. Biol. 127.6(1994):1755-1766.
Kishimoto et al. "Stimulation of the Side Population Fraction of ATDC5 Chondroprogenitors by Hypoxia." Cell Biol. Int. 33.12(2009):1222-1229.
Koretzky et al. "Role of the CD45 Tyrosine Phosphatase in Signal Transduction in the Immune System." FASEB J. 7.5(1993):420-426.
Kurosu et al. "Suppression of aging in mice by the hormone Klotho", Science 309(5742): 1829-1833, 2005.
Landhuis E, (2012), 'Muscle-Derived Stem Cells Slow Aging in Progeria Mouse Model,' Alzforum, Cambridge, MA (Pub), (8 pages), downloaded from <http://www.alzforum.org/news/research-news/muscle-derived-stem-cells-slow-aging-progeria-mouse-model_on_May_10>, 2014.
Lavasani M et al, (2012), 'Muscle-Derived Stem/Progenitor Cell Dysfunction Limits Healthspan and Lifespan in a Murine Progeria Model,' Nat Commun, 3:608 (12 pages).
Lipton et al. "Developmental Fate of Skeletal Muscle Satellite Cells." Science. 205(1979):1292-1294.
Liu et al., (2013), 'Prelamin A Accelerates Vascular Calcification via Activation of the DNA Damage Response and Senescence-Associated Secretory Phenotype in Vascular Smooth Muscle Cells,' Circ Res, 112(10):e99-109.
Ma et al. "Molecular Mechanisms of mTOR-Mediated Translational Control." Nat. Rev. Mol. Cell. Biol. 10.5(2009):307-318.

Mann et al., (2011), 'Aberrant Repair and Fibrosis Development in Skeletal Muscle,' Skel Mus, 1(21):1-20.
Martin et al. "The Expanding TOR Signaling Network." Curr. Opin. Cell. Biol. 17.2(2005):158-166.
McMahon et al. "C2C12 cells: biophysical, biochemical, and immunocytochemical properties", American Journal of Physiology 266 (Cell Physiology 35): C1795-C1802, 1994.
Merriam-Webster Dictionary Online, "myoblast", Merriam-Webster Inc., 2014.
Miller et al. "Seeking Muscle Stem Cells." Curr. Top. Dev. Biol. 43(1999):191-219.
Mizushima et al. "How to Interpret LC3 Immunoblotting." Autophagy. 3.6(2007):542-545.
Morgan et al. "Partial Correction of an Inherited Biochemical Defect of Skeletal Muscle by Grafts of Normal Muscle Precursor Cells." J. Neurol. Sci. 86(1988):137-147.
Morselli et al. "Autophagy Mediates Pharmacological Lifespan Extension by Spermidine and Resveratol." Aging. 1.12(2009):961-970.
Neff et al., (2013), 'Rapamycin Extends Murine Lifespan but has Limited Effects on Aging,' J Clin Invest, 123(8):3272-91.
Niedernhofer et al. "A New Progeroid Syndrome Reveals that Genotoxic Stress Suppresses the Somatotroph Axis." Nature. 444. 7122(2006)1038-1043.
Osawa et al. "In Vivo Self-Renewal of c-Kit.sup.+ Sca-1.sup.+ Lin.sup.low/—Hemopoietic Stem Cells." J. Immunol. 156(1996):3207-3214.
Partridge et al. "Conversion of mdx Myofibres From Dystrophin-Negative to -Positive by Injection of Normal Myoblasts." Nature. 337.6203(1989):176-179.
Partridge et al. "Evidence of Fusion Between Host and Donor Myoblasts in Skeletal Muscle Grafts." Nature. 273.5660(1978):306-308.
Price et al. "Lineage Analysis in the Vertebrate Nervous System by Retrovirus-Mediated Gene Transfer." PNAS. 84(1987):156-160.
Qu-Petersen et al. "Identification of a Novel Population of Muscle Stem Cells in Mice: Potential for Muscle Regeneration." J. Cell. Biol. 157.5(2002):851-864.
Quirós-González et al., (2016), 'Lamin A is Involved in the Development of Vascular Calcification Induced by Chronic Kidney Failure and Phosphoroous Load,' Bone, 84:160-8.
Ragnauth et al., (2009), 'Expanded Materials and Methods Supplementary Material,' (17 pages).
Ragnauth et al., (2010), 'Prelamin A Acts to Accelerate Smooth Muscle Cell Senescence and is a Novel Biomarker of Human Vascular Aging,' Circulation, 121(20):2200-10.
Ramos et al. "Rapamycin Reverses Elevated mTORC1 Signaling in Lamin A/C-Deficient Mice, Rescues Cardiac and Skeletal Muscle Function, and Extends Survival." Sci. Transl. Med. 4.144(2012):144ra103.
Ravikumar et al. "Inhibition of mTOR Induces Autophagy and Reduces Toxicity of Polyglutamine Expansions in Fly and Mouse Models of Huntington Disease." Nat. Genet. 36.6(2004):585-595.
Roobrouck et al. "Self-Renewal and Differentiation Capacity of Young and Aged Stem Cells." Exp. Cell Res. 314.9(2008):1937-1944.
Rossi et al. "Deficiencies in DNA Damage Repair Limit the Function of Haematopoietic Stem Cells with Age." Nature. 447. 7145(2007):725-730.
Salemi et al. "Autophagy is Required for Self-Renewal and Differentiation of Adult Human Stem Cells." Cell Res. 22.2(2012):432-435.
San Antonio et al. "Regulation of Chondrogenesis by Heparan Sulfate and Structurally Related Glycosaminoglycans." Dev. Biol. 123.1(1987):17-24.
Sanes et al. "Use of a Recombinant Retrovirus to Study Post-Implantation Cell Lineage in Mouse Embryos." EMBO J. 5.12(1986):3133-3142.
Schuierer et al., (2005), 'Analysis of the Differentiation Potential of Satellite Cells from myoD-/-, mdx, and PMP22 C22 Mice,' BMC Musculo Disord, 6(15):1-13.

(56) References Cited

OTHER PUBLICATIONS

Sheikh-Hamad D (2015), "Mammalian Stanniocalcin-1 Activates Mitochondrial Antioxidant Pathways: New Paradigms for Regulation of Macrophages and Endothelium." Am J Physiol—Renal Physiol, 298.2 (2010): F248-F254.
Simmons et al. "CD34 Expression by Stromal Precursors in Normal Human Adult Bone Marrow." Blood. 78(1991):2848-2853.
Stanfel et al. "The TOR Pathway Comes of Age." Biochim. Biophys. Acta. 1790.10(2009):1067-1074.
Tilstra JS, (2009), 'Evaluating the Role of NF-κβ suppression in Ameliorating Mammalian Disease: An Examination of Inflammatory Bowel Diseases Associated with Aging,' Thesis Dissertation, University of Pittsburgh.
Van de Rijn et al. "Mouse Hematopoietic Stem-Cell Antigen Sca-1 is a Member of the Ly-6 Antigen Family." PNAS. 86(1989):4634-4638.
Watt et al. "Long Term Survival of Allografted Muscle Precursor Cells Following a Limited Period of Treatment with Cyclosporin A." Clin. Exp. Immunol. 55.2(1984):419-426.
Webster et al. "Isolation of Human Myoblasts with the Fluorscence-Activated Cell Sorter." Exp. Cell Res. 174.1(1988):252-265.
Wullschleger et al. "TOR Signaling in Growth and Metabolism." Cell. 124.3(2006):471-484.
Ziegler et al. "KDR Receptor: A Key Marker Defining Hematopoietic Stem Cells." Science. 285.5433(1999):1553-1558.
Hasty et al. "Aging and Genome Maintenance: Lessons from the Mouse?," Science 299(2003):1355-1359.
Prasher et al. "Reduced hematopoietic reserves in DNA interstrand crosslink repair-deficient Ercc1 mice," The EMBO Journal 24(2005):861-871.

\* cited by examiner

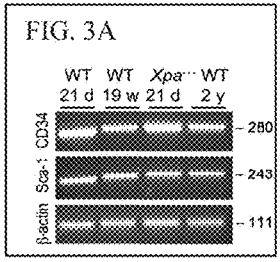
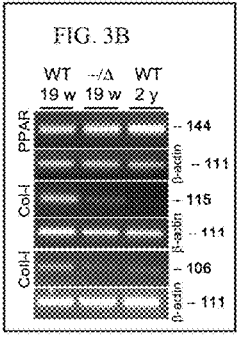
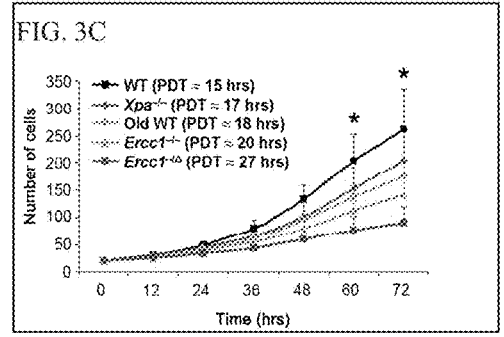
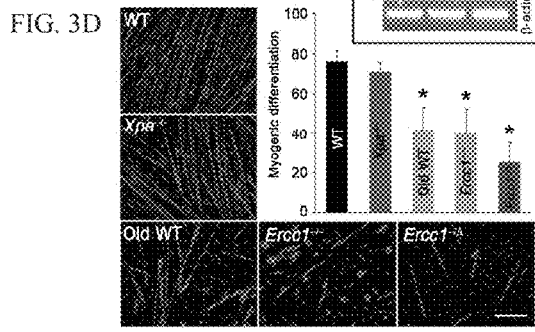
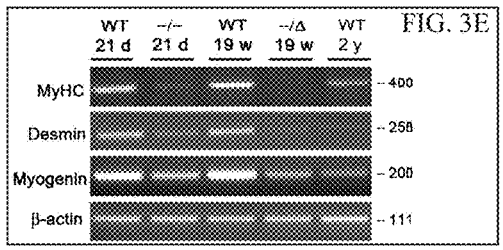
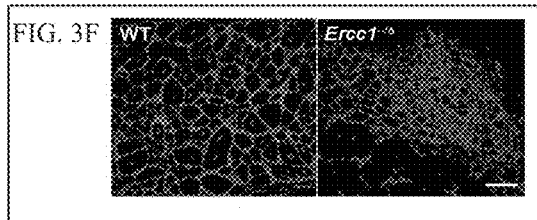
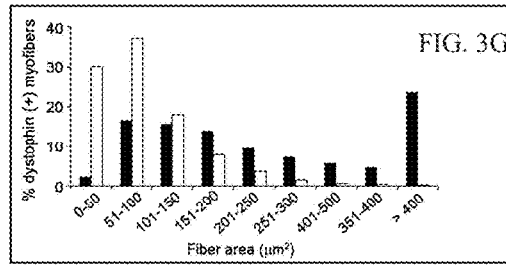

FIG. 4A
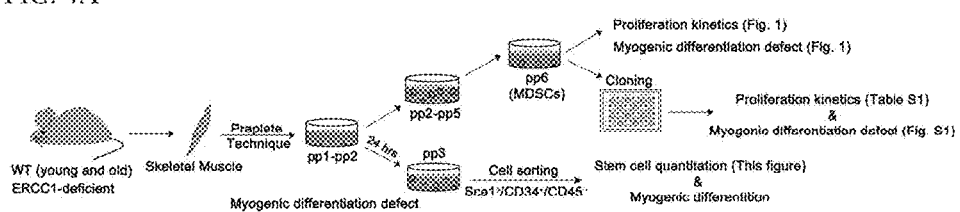
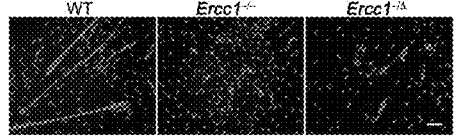
FIG. 4B
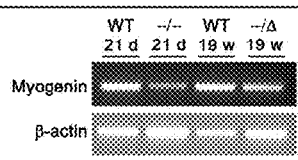
FIG. 4C
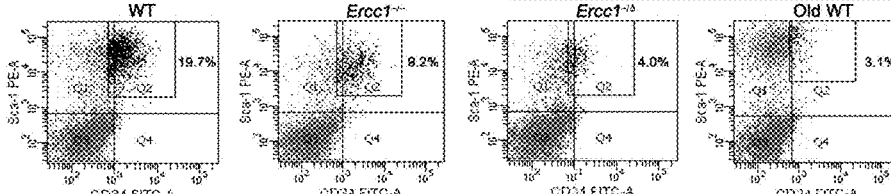
FIG. 4D
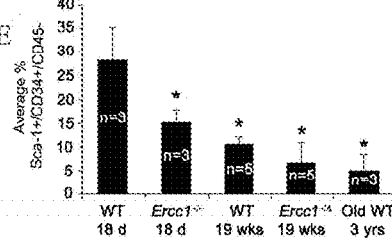
FIG. 4E
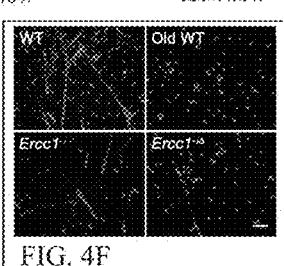
FIG. 4F
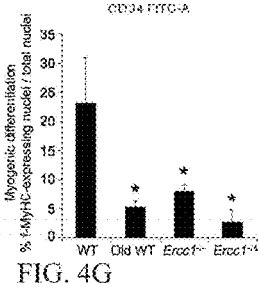
FIG. 4G FIG. 13A
FIG. 13B
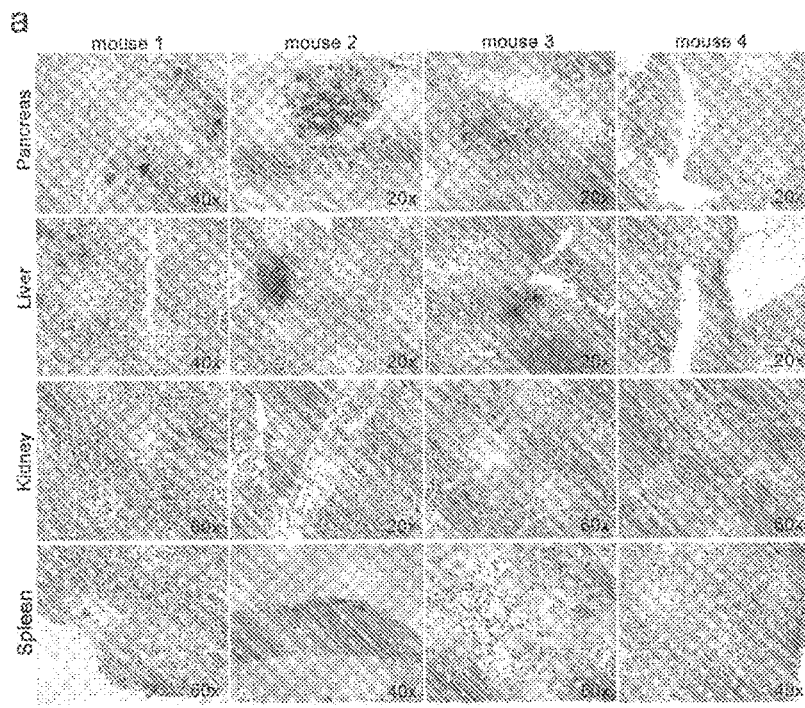
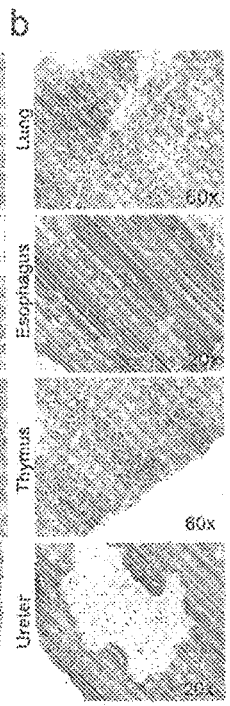

| Symptom | Age at onset (wks) |
|---|---|
| Dystonia | 8.9 |
| Trembling | 11.2 |
| Kyphosis | 12.9 |
| Ocular changes | 14.9 |
| Ataxia | 15.1 |
| Muscle wasting | 15.3 |
| Priapism | 17.1 |
| Urinary incontinence | 19.6 |
| Reduced activity | 20.4 |

FIG. 14

FIG. 15A
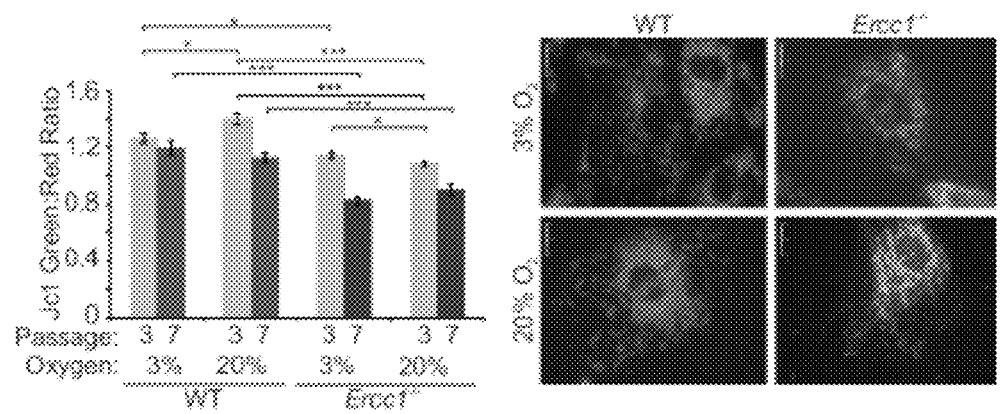
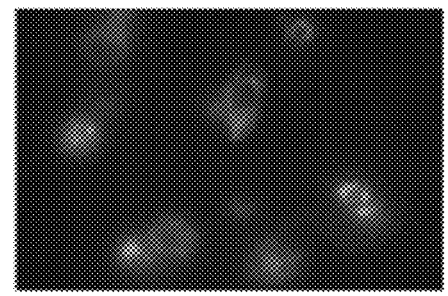
FIG. 15B
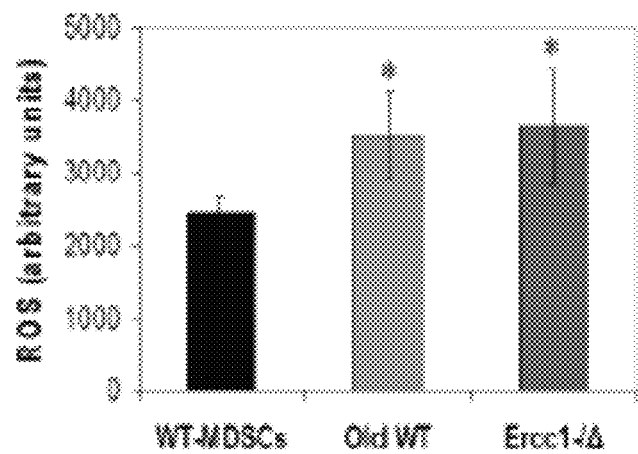

| Symptoms | Age at onset (wks) | | Change of onset (wks) | Number of Ercc1−/− mice (p65−/−, WT) |
|---|---|---|---|---|
| | Ercc1−/− | Ercc1−/− p65−/− | | |
| Dystonia | 7.7 | 7.4 | -0.3 | 6,10 |
| Trembling | 7.1 | 7.2 | 0.1 | 6,9 |
| Kyphosis | 10.3 | 11.5 | 1.2 | 6,12 |
| Ataxia | 12.1 | 12.4 | 0.3 | 6,12 |
| Sarcopenia | 13.2 | 12.9 | -0.3 | 6,12 |
| Priapism | 18.4 | 20.9 | 2.5 | 3,5 |
| Incontinence | 19.1 | 25.1 | 6.0 | 2,4 |
15 week old Ercc1−/−
15 week old Ercc1−/−p65−/−
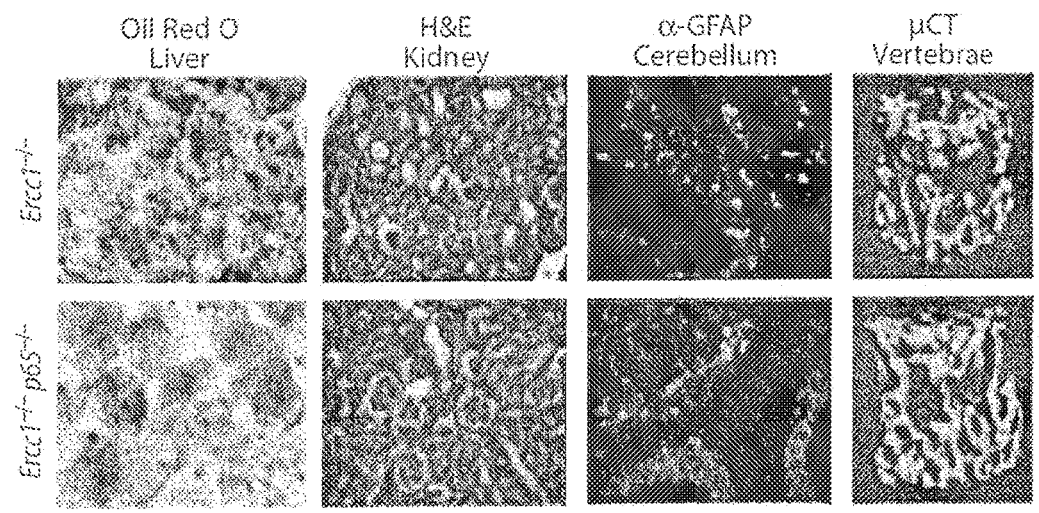
Fig. 20

FIG. 21A
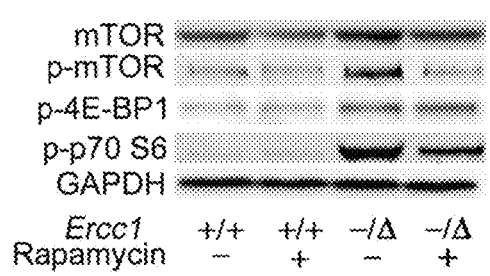
FIG. 21B
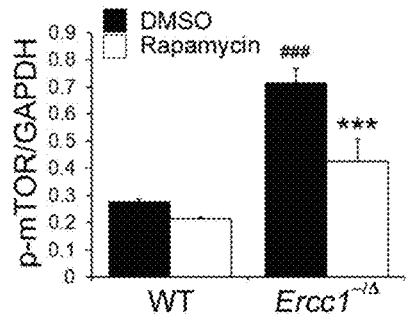
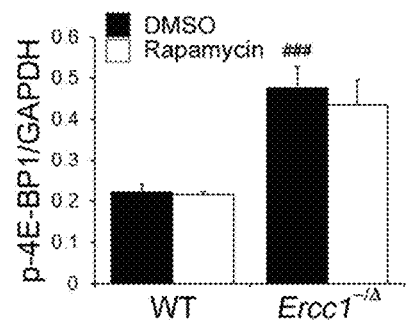
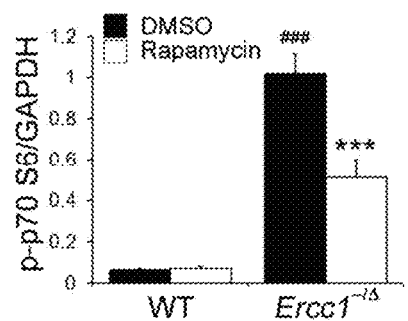
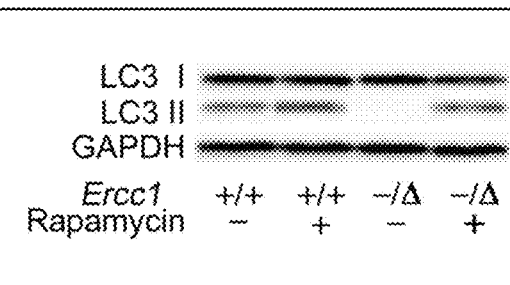
FIG. 21C
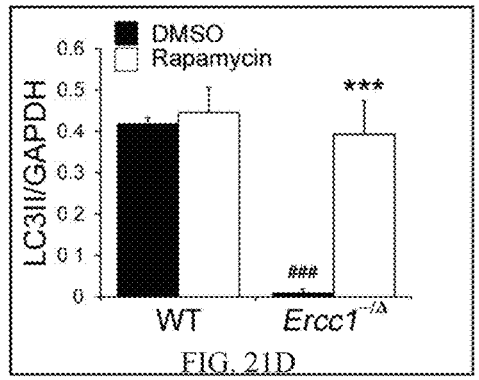
FIG. 21D

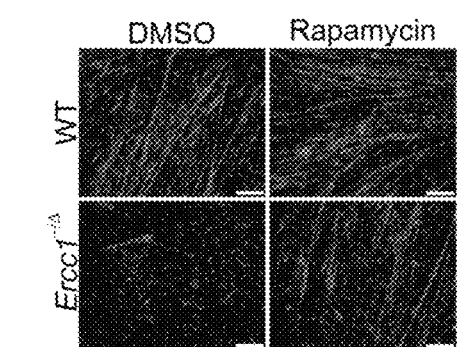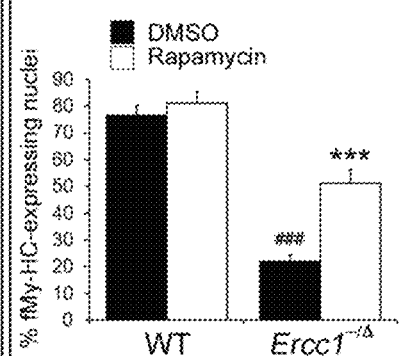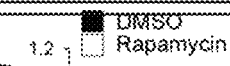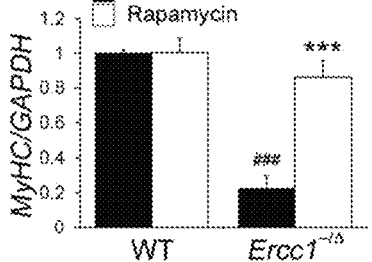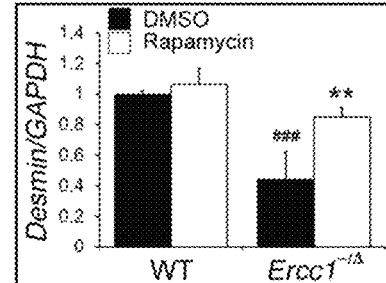

FIG. 25A
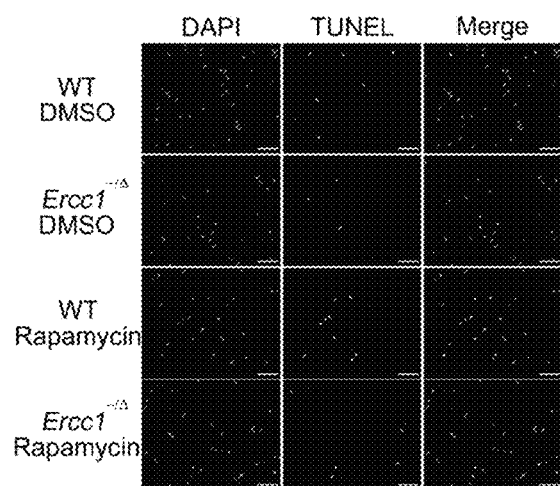
FIG. 25B
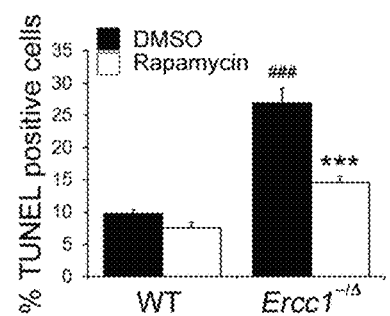
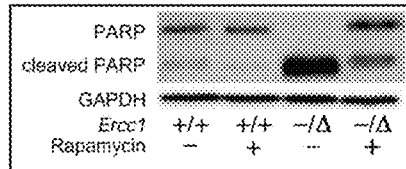
FIG. 25C

COMPOSITIONS AND METHODS FOR RESTORING OR REJUVENATING STEM/PROGENITOR CELL FUNCTION

RELATED APPLICATIONS

This application is a divisional of U.S. patent application Ser. No. 13/912,927, filed Jun. 7, 2013 (now U.S. Pat. No. 9,295,696), which claims the benefit U.S. Provisional Application No. 61/657,104, filed on Jun. 8, 2012; the contents of each of which is incorporated herein by reference in its entirety.

GOVERNMENT INTERESTS

This invention was made with government support under Grant No. AR051456 awarded by the National Institutes of Health. The Government has certain rights in the invention.

INCORPORATION-BY-REFERENCE OF SEQUENCE LISTING

The contents of the text file named "28682-511001US_ST25.txt", which was created on Jun. 6, 2013 and is 7 KB in size, are hereby incorporated by reference in their entirety.

FIELD OF THE INVENTION

The invention relates generally to the use of autologous or allogeneic stem or progenitor cells, or factors that are secreted or released therefrom, to restore or rejuvenate the function of endogenous stem or progenitor cells in a mammal. The invention also relates to methods for identifying candidate compounds or molecules that modulate expression, function, release and/or secretion of one or more regulatory factors secreted or released from the stem or progenitor cells.

BACKGROUND OF THE INVENTION

A universal characteristic of aging is the loss of regenerative capacity leading to an impaired ability to respond to stress and therefore increased morbidity and mortality. This loss of regenerative capacity suggests that aging is associated with or is caused, in part, by the loss of functional stem cells necessary for tissue regeneration.

Mice greater than two years of age are known to have a significant reduction in the number and proliferative capacity of neural stem cells and male germ-line stem cells. In contrast hematopoietic stem cell (HSC) numbers are preserved as mice age, but the function of the cells is impaired. Muscle satellite cells also lose stem cell properties with aging, but how many satellite cells are present as the animal ages remains controversial. Aging-related changes in bone marrow-derived mesenchymal stem cells (MSCs) include loss of proliferation and differentiation potentials; increase in senescence; and loss of capacity to form bone in vivo. MSCs derived from the bone marrow of patients with Hutchinson-Gilford progeria syndrome, a disease of dramatically accelerated aging, are defective in their ability to differentiate. Adipose-derived multipotent cells display an age-dependent loss of self-renewal capacity and an increased propensity for adipogenesis.

Despite the observed correlation of decline in stem cell population with aging, it is unclear whether the decline of number of stem cells or the dysfunction of remaining stem cells results in aging-related degenerative changes.

Numerous studies provide evidence that the number and/or function of diverse adult stem/progenitor cell populations decline with aging. However, these are largely correlative studies that do not discriminate if changes in the stem cell compartment play a causative role in aging or are merely a consequence of aging. Moreover, prior studies fail to disprove that loss of stem cell population is not merely a biomarker of aging.

Genetic studies revealed proteins and pathways essential for the maintenance of stem cell function. Mutation of these genes leads to foreshortened lifespan and early onset of some aging-related pathologies. For example, mice deficient in the polycomb protein BMI-1 have a short lifespan along with defects in self-renewal of HSCs leading to adult stem cell depletion. Similarly, mice deficient in HMGA2 display reduced stem cell numbers and function (self-renewal) throughout the central and peripheral nervous systems. Finally, HSC function and regenerative capacity are significantly diminished in mice harboring mutations in diverse DNA repair genes or telomerase ($Lig4^{Y288C}$, $Ku80^{-/-}$, $Xpd^{TTD}$, and $mTR^{-/-}$) indicating that genome and telomere maintenance are crucial for stem cell function. However, there is no evidence that loss of stem cell function is directly responsible for decreased lifespan and aging-related pathology in these models.

Thus, there is a need in the art for additional means for extending lifespan and/or improving health in an aging or aged mammal.

SUMMARY OF THE INVENTION

The invention provides methods for restoring or rejuvenating adult stem/progenitor cell function in a mammal in need thereof, by administering an exogenous amount of isolated autologous or allogeneic stem/progenitor cells (e.g., adult stem/progenitor cells) to the mammal, wherein endogenous adult stem/progenitor cells of the mammal are depleted or dysfunctional, and wherein the isolated autologous or allogeneic stem/progenitor cells secrete or release one or more regulatory factors; wherein the one or more secreted stimulatory factors restore or rejuvenate the adult stem cell function.

For example, restoring or rejuvenating adult stem/progenitor cell function may extend lifespan and/or improve health of the mammal.

In one embodiment, between about $2\times10^5$ and about $5\times10^5$ stem/progenitor cells per gram of body weight of a mammal may be administered to the mammal.

Those skilled in the art will recognize that restoring or rejuvenating adult stem/progenitor cell function in a mammal treats, delays, prevents, and/or ameliorates one or more symptoms associated with aging. Moreover, restoring or rejuvenating adult stem/progenitor cell function in a mammal treats, delays, prevents, and/or ameliorates one or more symptoms of dystonia, kyphosis, ataxia, sarcopenia, incontinence, lethargy, and/or trembling in a mammal.

Also provided are methods for restoring or rejuvenating adult stem/progenitor cell function in a mammal wherein administration of isolated stem/progenitor cells (e.g., adult stem/progenitor cells) promote neovascularization of a tissue in the mammal. Those skilled in the art will recognize that the tissue being neovascularized can be selected from, for example, bone, skeletal muscles, cardiac muscles, brain, kidney, spinal cord, nervous system, pancreas, islets, liver, bladder, ureter, bone marrow, ligaments, tendons, cartilage, and/or any combination(s) thereof.

In any of the methods of the invention, the isolated autologous or allogeneic stem/progenitor cells (e.g., adult stem/progenitor cells) are administered in combination with one or more mTOR inhibitors to the mammal, and wherein the one or more mTOR inhibitors restore or rejuvenate the adult stem cell function. The one or more mTOR inhibitors may be administered prior to, simultaneously with, or following administration of the isolated stem/progenitor cells. Examples of suitable mTOR inhibitors include, for example, sirolimus (rapamycin, RAPAMUNE®), everolimus (ZORTRESS®, RAD001), temsirolimus (TORISEL®, CCI-779), deforolimus (AP23573, MK-8669, RIDAFOROLIMUS®), Torin1, Torin2, PP242, KU0063794, WYE-687 dihydrochloride, WYE-354, WYE-125132, WAY-600, AZD8055, AZD2014, OSI-027, PP242, PF04691502, PF05212384, INK128 (MLN0128), as well as derivatives, analogs, and/or combination(s) thereof.

In any of the methods of the invention, the administration of stem/progenitor cells (e.g., adult stem/progenitor cells) promotes tissue regeneration in the mammal. For example, the tissue being regenerated can be selected from, for example, bone, skeletal muscles, cardiac muscles, brain, kidney, spinal cord, nervous system, pancreas, islets, liver, bladder, ureter, bone marrow, ligaments, tendons or cartilage, and/or any combination(s) thereof.

Also provided are methods for restoring or rejuvenating adult stem/progenitor cell function in a mammal by extending lifespan of a mammal, wherein the mammal carries a xeroderma pigmentosum complement group F mutation. The mice have a mutation in Excision repair cross-complementation group 1. The effect of the mutation is reduced expression of the protein complex ERCC1-XPF. This models a human progeroid syndrome caused by mutations in XPF.

In other embodiments, the invention further provides methods of treating, preventing, or reversing progeria or related syndromes (e.g., a progeroid-like syndrome) in a mammal by administering an effective amount of isolated autologous or allogeneic stem/progenitor cells (e.g., adult stem/progenitor cells) to the mammal, wherein the isolated autologous or allogeneic stem cells secrete or release one or more regulatory factors; wherein the one or more secreted or released regulatory factors treat, prevent, and/or reverse one or more symptoms of progeria or related syndromes in the mammal.

In any of the methods of the invention, administration of isolated stem/progenitor cells (e.g., adult stem/progenitor cells) into a mammal stimulates regeneration of bone, skeletal muscles, cardiac muscles, brain, kidney, spinal cord, nervous system, pancreas, islets, liver, bladder, ureter, bone marrow, ligaments, tendons, cartilage, and/or any combination(s) thereof.

Those skilled in the art will recognize that in any of the methods and compositions described herein, stem/progenitor cells can include, by way of non-limiting example, skeletal muscle-derived stem/progenitor cells (MDSPCs), hematopoietic stem/progenitor cells, neural stem/progenitor cells, heart-derived stem/progenitor cells, intestinal stem/progenitor cells, mesenchymal stem/progenitor cells, endothelial stem/progenitor cells, epithelial stem/progenitor cells, olfactory adult stem/progenitor cells, neural crest stem/progenitor cells, testicular stem/progenitor cells, embryonic stem cells, placental derived stem/progenitor cells, amniotic fluid-derived stem/progenitor cells, cord blood stem/progenitor cells, and/or inducible pluripotent stem cells.

In addition, in any of the methods of the invention, restoring or rejuvenating adult stem cell function increases the body weight of the mammal.

Also provided are compositions containing one or more secreted or released regulatory factors from isolated mammalian stem/progenitor cells (e.g., adult stem/progenitor cells).

By way of non-limiting example, the one or more secreted or released regulatory factors can be peptides, proteins, RNA, microRNAs, small non-coding RNAs, carbohydrates, lipids, hormones, and/or any mixture(s) thereof.

In one embodiment of the invention, the one or more secreted or released regulatory factors isolated from mammalian stem/progenitor cells can include: RBP-JK inhibitory factor, Stanniocalcin-1, Wnt3a, KLOTHO, CCL11, miRNA-489, VEGF, HGF, IGF, microvesicles and/or exosomes.

These one or more secreted or released regulatory factors can stimulate regeneration of bone, skeletal muscles, cardiac muscles, brain, kidney, spinal cord, nervous system, pancreas, islets, liver, bladder, ureter, bone marrow, ligaments, tendons, cartilage, and/or any combination(s) thereof.

Moreover, the one or more secreted or released factors of this invention promote neovascularization in bone, skeletal muscles, cardiac muscles, brain, kidney, spinal cord, nervous system, pancreas, islets, liver, ureter, bladder, and/or any combination(s) thereof.

In one embodiment of the invention, the one or more secreted or released regulatory factors promotes tissue regeneration of one or more tissues selected from, for example, bone, skeletal muscles, cardiac muscles, brain, kidney, spinal cord, nervous system, pancreas, islets, liver, bladder, ureter, bone marrow, ligaments, tendons, and/or cartilage.

In one embodiment of the invention, the composition contains one or more secreted or released regulatory factors from isolated mammalian stem/progenitor cells and/or one or more mTOR inhibitors.

The invention further provides pharmaceutical compositions containing one or more regulatory factors secreted or released from isolated mammalian stem/progenitor cells (e.g., adult stem/progenitor cells) and one or more pharmaceutically acceptable excipients.

In one embodiment of the invention, the pharmaceutical composition contains one or more secreted or released regulatory factors from isolated mammalian stem/progenitor cells, and/or one or more mTOR inhibitors, and one or more pharmaceutically acceptable excipients.

Methods are also provided for extending lifespan of a mammal, or improving health of a mammal, or both, by administering an effective amount of the composition containing one or more secreted or released regulatory factors from isolated mammalian stem/progenitor cells (e.g., adult stem/progenitor cells) to a mammal, wherein endogenous adult stem/progenitor cells in the mammal (e.g., in the skeletal muscle of the mammal) are depleted or dysfunctional due to age, and wherein the composition extends lifespan and/or improves health of said mammal.

Methods are also provided for extending lifespan of a mammal, or improving health of a mammal, or both, by administering an effective amount of the composition containing one or more secreted or released regulatory factors from isolated mammalian stem/progenitor cells (e.g., adult stem/progenitor cells) and/or one or more mTOR inhibitors to a mammal, wherein endogenous adult stem/progenitor cells in the mammal (e.g., in the skeletal muscle of the mammal) are depleted or dysfunctional due to age, and wherein the composition extends lifespan and/or improves health of said animal.

In one embodiment, methods are provided for extending lifespan of a mammal, or improving health of a mammal, or both, by administering an effective amount of the composition containing one or more mTOR inhibitors to a mammal to increase autophagy, wherein the composition prevents loss of differentiation capacity of endogenous stem/progenitor cells or extends lifespan and/or improves health of said animal.

By means of non-limiting example, the administration of the composition may treat, delay, prevent, and/or ameliorate one or more symptoms in the mammal associated with one or more of aging, dystonia, kyphosis, ataxia, sarcopenia, incontinence, lethargy, and/or trembling.

Likewise, any of the compositions of the invention can be used to promote neovascularization and/or tissue regeneration in the mammal.

Additionally, these compositions can be used to treat, delay, and/or ameliorate one or more symptoms associated with aging in a mammal, wherein the mammal carries Xeroderma pigmentosum complement group F mutation, wherein the mammal has a progeroid like syndrome, and/or wherein the mammal has progeria.

This invention provides methods for identifying one or more candidate compounds that modulate expression of one or more secreted or released regulatory factors in a population of isolated mammalian stem/progenitor cells (e.g., adult stem/progenitor cells), wherein the method involves, without being limited to, the steps, exposing said population of stem/progenitor cells to the one or more candidate compounds; determining expression of the one or more regulatory factors in the population of stem/progenitor cells exposed to the candidate compound and in a control population of stem/progenitor cells that are not exposed to the candidate compound; and comparing the expression of the one or more regulatory factors in the exposed population of stem/progenitor cells with expression in the control population of stem/progenitor cells; thereby identifying the one or more candidate compounds that modulate expression of the one or more secreted regulatory factors.

Those skilled in the art will recognize that when the expression of one or more secreted or released regulatory factors is greater in the exposed population compared to the control population, the one or more candidate compound increases expression of the one or more secreted or released regulatory factors.

Similarly, when the expression of one or more secreted or released regulatory factors is lower in the exposed population compared to the control population, the one or more candidate compound decreases expression of one or more secreted or released regulatory factors.

In yet another embodiment of the invention, methods are provided for treating, preventing, or reversing progeria or related syndromes in a mammal by administering an effective amount of a composition containing one or more secreted or released regulatory factors to the mammal, wherein the one or more secreted or released regulatory factors treat, prevent, or reverse one or more symptoms of progeria or related syndromes in the mammal.

DESCRIPTION OF THE DRAWINGS

FIGS. 3A-3G depicts measurement of MDSPC proliferation, differentiation and regenerative potential. (a) (FIG. 3A) RT-PCR to measure stem/progenitor cell markers CD34 and Sca-1 in MDSPCs isolated from muscle of mice at various ages. Shown is a representative image from analysis of 3-4 independent MDSPC populations per genotype/age at passage 23-25. (b) (FIG. 3B) RT-PCR to measure differentiation markers. Peroxisome Proliferator-Activated Receptor (PPAR) is an adipocyte marker; collagen 1 (Col-1) is an osteocyte marker; collagen-2 (Col-2) is a chondrocyte marker. β-actin was the loading control. Shown is a representative image from analysis of 3 independent MDSPC populations of each genotype/age. (c) (FIG. 3C) Proliferation of MDSPCs measured by Live Cell Imaging. Plotted are the average number of cells at each time point calculated from 3-4 populations per genotype±s.d. (*$P<0.05$, Tukey test). Average population doubling time (PDT) was calculated from analysis of 40 images per time point. (d) (FIG. 3D) Representative images of in vitro myogenic differentiation. Cells were immunostained for the terminal differentiation marker, f-MyHC (red). Scale bar=100 μm. Quantification of myogenic differentiation was calculated as the fraction of cells (DAPI, blue) expressing f-MyHC (red) from 3-4 cell populations per genotype±s.d; *$P<0.001$ relative to young WT-MDSPCs (black bar), Kruskal-Wallis ANOVA on ranks. (e) (FIG. 3E) RT-PCR to measure expression of the terminal differentiation markers, MyHC, desmin, and myogenin, after myogenic differentiation of MDSPCs isolated from mice of various genotypes/ages. Shown is a representative image from 3 MDSPC populations tested per group. (f) (FIG. 3F) Representative image of gastrocnemius muscle sections from dystrophic mice 14 days post-injection of WT or Ercc1$^{-/\Delta}$ MDSPCs to test myogenic differentiation in vivo. The sections were immunostained for dystrophin (red) to identify myofibers from donor cells. Scale bar=100 µm. (g) (FIG. 3G) Quantification of the donor myofiber area in dystrophic mice transplanted with WT-MDSPCs (black bars) or MDSPCs from Ercc1$^{-/\Delta}$ mice (white bars). Plotted is the average number of myofibers of each size range calculated from >2000 fibers analyzed per mdx/SCID mouse (n=8) treated with 2 independent MDSPC populations per genotype. ($P<0.001$, for all distribution ranges except 101-150; Mann-Whitney Rank sum test).

FIGS. 4A-4G shows measurements of the number of MDSPCs isolated from murine muscle and their myogenic potential. (a) (FIG. 4A) A schematic diagram showing the early passage cells analyzed in this FIG. and the method used to isolate various populations of MDSPCs (pp1-pp6). (b) (FIG. 4B) Representative images of pp1-pp2 cells induced to undergo myogenic differentiation. Cells directly isolated from skeletal muscle of mice, using preplate technique (pp1-pp2), were incubated in fusion media to induce myogenic differentiation. Twenty-four hours post-isolation, adhering cells were trypsinized and plated at equal density and induced to undergo myogenic differentiation over 2-3 days. Cells from 2-3 independent populations of each genotype were immunostained for the terminal myogenic differentiation marker, f-MyHC (red). Scale bar=100 µm. (c) (FIG. 4C) RT-PCR to measure the expression of the myogenic differentiation marker, myogenin in pp1-pp2 cells, induced to undergo myogenic differentiation. (d) (FIG. 4D) Quantification of Sca-1$^+$/CD34$^+$/CD45$^-$ cells in young WT-, old WT-, and progeroid-(Ercc1$^{-/-}$, Ercc1$^{-/\Delta}$) murine skeletal muscle. Twenty-four hours after isolation from muscle, the cells that did not adhere in preplate 1 and 2 (i.e., pp3) were analyzed for stem/progenitor cell markers by FACS. The number in the upper right quadrants indicates the percent of Sca-1$^+$/CD34$^+$/CD45$^-$ cells isolated from 3-5 mice of each genotype/age. (e) (FIG. 4E) Graph indicating the average fraction of Sca-1$^+$/CD34$^+$/CD45$^-$ cells normalized to the weight of the cell pellet of pp3 cell populations. Error bars indicate ±s.d. *$P<0.05$, Tukey test, relative to young WT cells. (f) (FIG. 4F) Representative images of Sca-1$^+$/CD34$^+$/CD45$^-$ sorted cells plated at equal density and induced to undergo myogenic differentiation. The cells were stained for the terminal myogenic marker, f-MyHC (red). Scale bar=100 µm. (g) (FIG. 4G) Quantitation of myogenic differentiation of Sca-1$^+$/CD34$^+$/CD45$^-$ cells isolated from the skeletal muscle of mice of various genotypes/ages measured as the percent of cells (DAPI, blue) expressing f-MyHC (red). Error bars indicate ±s.d. for cell populations isolated from 2-3 animals per genotype *$P<0.001$, Kruskal-Wallis ANOVA on ranks relative to young WT cells.

(FIG. 5A) Representative images of damaged muscle sections. Scale bar=100 µm. (FIG. 5B) Quantification of the cross-sectional area of regenerating myofibers after muscle injury of adult WT mice (black bars), progeroid Ercc1$^{-/\Delta}$ littermates (white bars) and old WT mice (grey bars). The area of >1000 myofibers was measured per group of mice. The distribution of fiber size is indicated on the x-axis, representing increasingly more mature fibers with increased size. The fraction of regenerating, centronucleated myofibers of each size range is plotted. ($P<0.001$, Kruskal-Wallis ANOVA on ranks at 0-250, 251-500, and >1000). (FIG. 5C) Trichrome staining of sections from the same damaged muscles to reveal areas of fibrosis (blue). Shown are representative images from 1 of 2-3 mice of each genotyped analyzed. (FIG. 5D) Histogram indicating the area of fibrotic scarring following cardiotoxin injection. Plotted is the average fraction (n=2-3 animals per genotype/age) of the area examined that is fibrotic in percent±s.d. *$P<0.05$, Tukey test, relative to young WT. Scale bar=100 µm.

(FIG. 6A) A schematic diagram of the co-culture system used to evaluate the effect of young functional MDSPCs on dysfunctional MDSPCs isolated from progeroid or old WT mice. Ercc1$^{-/-}$ MDSPCs were plated in the lower compartment of the transwell system in proliferation media. WT-MDSPCs were seeded onto the upper transwell membrane inserts, at the same density, and in the same media. These co-cultures were placed in the LCI system for 72 hrs to acquire time-lapsed images in order to measure proliferation of the MDSPCs. As a control, each plate contained wells of Ercc1$^{-/-}$ MDSPCs without transwell membrane inserts. (FIG. 6B) Plotted is the average cell number at each time point calculated from the analysis of 3 independent populations of Ercc1$^{-/-}$ MDSPCs co-cultured with young WT-MDSPCs±s.d. *$P<0.001$, Mann-Whitney Rank sum test. (FIG. 6C) The transwell inserts were removed after 72 hrs and the proliferation media was switched to differentiation media. After 2-3 days, myogenic differentiation was tested by immunostaining the cells for f-MyHC. Shown are representative images. The nuclear counterstain is DAPI. Scale bar=100 µm. (FIG. 6D) Quantitation of myogenic differentiation of old WT-MDSPCs after growth in media conditioned from young WT-MDSPCs. Young WT-MDSPCs were cultured for 2 days in proliferation media in collagen coated flasks then treated with differentiation media for 3 days. The supernatant from these cultures was collected for use as conditioned media. MDSPCs from 21 day-old progeroid Ercc1$^{-/-}$ mice and 2 yr-old WT mice were grown in the presence of this conditioned media or unconditioned differentiation media to determine the impact on myogenic differentiation as measured by immunoblot detection of MyHC. Densitometric quantification of MyHC corrected for β-actin is indicated below each lane.

(FIG. 7A) Representative sections from the gastrocnemius muscle of 15 day-old WT and Ercc1$^{-/-}$ mice, as well as Ercc1$^{-/-}$ mice transplanted with young WT-MDSPCs at 17 days of age and allowed to live their full lifespan, immunostained for dystrophin, CD31, and DAPI. Arrows indicate myofibers lacking adjacent CD31+ cells (microvasculature). Scale bars=100 µm. (FIG. 7B) Quantitation of microvasculature and myofiber size in these mice. Images from 4-8 sections and 500-1000 fibers from 3 animals per group were analyzed. Reported is the ratio of CD31$^+$ cells to dystrophin-positive muscle fibers (left) and the average muscle fiber size (cross-sectional area; right). Error bars indicate s.e.m. *P<0.001, Students t-test comparing the Ercc1$^{-/-}$ mice with WT mice and $^§$ P<0.05, Tukey test comparing untreated and treated Ercc1$^{-/-}$ mice; for myofiber size *P=0.002, Mann-Whitney Rank sum test comparing the Ercc1$^{-/-}$ mice with WT mice and P<0.05, Dunn's Method comparing untreated and treated Ercc1$^{-/-}$ mice. (FIG. 7C) Representative images from sections of the cerebral cortex of 21 day old WT and Ercc1$^{-/-}$ mice, and Ercc1$^{-/-}$ mice transplanted with young WT-MDSPCs. Tissue sections were stained for CD31 to detect the microvasculature. The percent of the tissue area representing vasculature was quantified using brightfield images and Northern Eclipsed software. Each circle plotted represents an individual mouse. The horizontal bar is the median (50$^{th}$ percentile) area. The box represents the 25$^{th}$-75$^{th}$ percentile, and the error bars represent the 10$^{th}$-90$^{th}$ percentile.

(FIG. 8A) The gastrocnemius muscle of 12 day-old Ercc1$^{-/-}$ mice (n=3 mice) was injected with young WT-MDSPCs. Tissues were isolated 5 days later (17 d) and sections were immunostained for dystrophin, CD31, and DAPI and compared to untreated 15 day-old WT and Ercc1$^{-/-}$ mice (from FIG. 7A). The white arrow denotes a centronucleated fiber. Scale bar=100 m. (FIG. 8B) Quantitation of microvasculature and myofiber size in transplanted and untreated mice. Images from 4-8 sections from 3 animals per group were analyzed. Reported is the ratio of CD31$^+$ cells to dystrophin-positive muscle fibers (left), $^§$ P<0.05 between untreated and treated Ercc1$^{-/-}$ mice, Tukey test. On the right is the average muscle fiber size (cross-sectional area), $^§$ P<0.05 between untreated and treated Ercc1$^{-/-}$ mice, Dunn's test. Error bars indicate s.e.m. (FIG. 8C) Seventeen day-old progeroid Ercc1$^{-/-}$ mice (n=10) were injected IM with WT-MDSPCs expressing nuclear LacZ to determine if donor cells integrate into muscle fibers and contribute to blood vessels. Five days later, the mice were euthanized and the gastrocnemius muscles were isolated for analysis. Muscle sections at the injection site were stained with X-gal to detect donor cells and eosin. Scale bar=50 μm. (FIG. 8D) Histogram of the cross-sectional area distribution of myofibers in the treated gastrocnemius muscles (black bars) compared the contralateral non-injected muscle (white bars). Data were collected from 6,000 fibers from multiple sections of 4 mice per group. The distribution of fiber size is indicated on the x-axis, representing increasingly more mature fibers with increased size (P<0.001, Mann-Whitney Rank sum test at 151-300 and 301-450). (FIG. 8E) Sections from the injected muscles stained for CD31 to identify blood vessels and X-gal to identify donor cells. Arrowheads indicate CD31$^+$ capillary structures. Sections from dystrophic (mdx/SCID) mice treated the same way are included as a positive control (right panels). Scale bars=50 μm.

FIGS. 13A-13B depicts the determination of the site for donor cell engraftment after transplantation of progeroid Ercc1$^{-/-}$ mice with young WT-MDSPCs. 2-4×10$^5$ young WT-MDSPCs expressing nuclear LacZ per gram body-weight were injected IP into Ercc1$^{-/-}$ mice to determine the sites of engraftment. Mice were injected at 12 days of age and euthanized 8-9 days later (n=4) or injected at 17-19 days of age and tissues harvested at the end of their lifespan (4-9 wks of age; n=4). Fourteen organs/tissues were isolated, sectioned and stained with X-gal to identify donor cells. (a) (FIG. 13A) Donor cells (LacZ+ stained) were detected in the pancreas, liver, spleen, and kidney of all host animals. Shown are representative images from 4 mice illustrating the site and extent of engraftment of donor cells. (b) (FIG. 13B) Donor cells were detected in the lung, esophagus, thymus, bladder, and bone marrow of at least 1 mouse. Shown are images at multiple levels of magnification from tissue sections of 1 mouse per organ to illustrate the site and extent of engraftment. The level of magnification is indicated for each tissue section image. The last row depicts brightfield image (left) of cells isolated from the bone marrow of the long bones (hindlimb) depicting LacZ+ donor cells (black arrows). The right panel is a fluorescent image of the same sample illustrating co-localization (white arrows) of the LacZ+ donor cells with leukocyte marker CD45.

FIG. 14 shows the age at onset of progeroid symptoms in Ercc-1$^{-/-}$ mice as determined from a cumulative history of examining >200 mice. Shading indicates symptoms caused by neurodegeneration.

FIGS. 15A-15B depict the effects of hyperoxia on the mitochondrial membrane potential in primary Mouse Embryonic Myoblasts (MEFs) isolated from wild-type (WT) and Ercc1$^{-/-}$ mice. Mitochondrial depolarization is indicated by a decrease in the red/green fluorescence intensity ratio. The graph represents the ratio of JC1 red (aggregates): JC1 green (monomers) for n=100 cells from three independent cell lines for WT and Ercc1$^{-/-}$ at 3% and 20% $O_2$. Independent cell lines for WT and Ercc1$^{-/-}$ at 3% and 20% 02. Error bars represent the S.E.M. *indicates significance using a two tailed Student's t-test where p<0.05, and *** indicates p<0.001. Representative images are shown in the right-hand panels. The data showed that DNA repair-deficient Ercc1$^{-/-}$ MEFs had lower mitochondrial membrane potential compared to WT MEFs, when cultured at 3% or 20% O2 (FIG. 15A) suggesting that failure to repair nuclear DNA damage drives loss of mitochondrial membrane potential. (FIG. 15B) shows that muscle derived stem/progenitor cells (MDSPCs) isolated from old WT and progeroid Ercc1$^{-/\Delta}$ mice show increased oxidative stress compared to stem cells from young adult mice. ROS, primarily generated by mitochondria, DNA damage and stem cell dysfunction are all implicated in aging. Ercc1$^{-/\Delta}$ mice are DNA repair-deficient. Thus, they accumulate DNA damage faster than WT mice and as a consequence age rapidly and lose stem cell function. Because their accelerated aging is spontaneous, it is attributed to oxidative DNA damage caused by mitochondrial-derived ROS.

FIG. 20 shows that genetic depletion of the p65 NF-κB subunit delays accelerated aging. Ercc1$^{-/\Delta}$ and Ercc1$^{-/\Delta}$ p65$^{+/-}$ mice were evaluated biweekly for spontaneous symptoms associated with aging. Shown is the average age-at-onset for each symptom for each group and the difference between the group averages. Yellow shaded cells indicate symptoms delayed in the p65 heterozygous mice. Also shown are representative images of Ercc1$^{-/\Delta}$ and Ercc1$^{-/-}$ p65$^{+/-}$ sex-matched littermates at 15 weeks of age and histopathologic changes. Liver sections were stained with oil red O to detect neutral lipids in 10 wk-old mice. Kidney specimens from 15 wk-old mice were stained with haematoxlin and eosin to detect proteinaceous renal hyaline tubular casts and glomerulosclerosis. Cerebellar sections were immunostained for GFAP, a marker of neurodegeneration, in 10 wk-old mice. Nuclei were counter-stained with DAPI. Osteoporosis was measured by μCT analysis.

FIGS. 21A-21D depicts measurement of mTOR activity and autophagy in MDSPCs isolated from progeroid Ercc1$^{-/\Delta}$ mice. (FIG. 21A) Shown is a representative image of immunoblotting to measure mTOR, p-mTOR, p-4E-BP1 and p-p70 S6 expressions in MDSPCs isolated from Ercc1$^{-/\Delta}$ and WT mice cultured with and without rapamycin. (FIG. 21B) Quantification of p-mTOR, p-4E-BP1 and p-p70 S6 expression relative to GAPDH. Error bars indicate the standard deviation. Statistical significance was determined using one-way ANOVA or Kruskal-Wallis test with Tukey-Kramer or Scheffe's post-hoc test (n=4). ###p<0.001 versus WT-DMSO, *p<0.001 versus Ercc1$^{-/\Delta}$-DMSO. (FIG. 21C) Representative image of immunoblotting to measure autophagy markers LC3 I and II expression in MDSPCs isolated from Ercc1$^{-/\Delta}$ and WT mice cultured with and without rapamycin. (FIG. 21D) Quantification of LC3II expression relative to GAPDH was calculated. Error bars indicate the standard deviation. Statistical significance was determined using Kruskal-Wallis test with Scheffe's post-hoc test (n=4). ###p<0.001 versus WT-DMSO, *p<0.001 versus Ercc1$^{-/\Delta}$-DMSO.

FIGS. 22A-22D depicts measurement of the effect of rapamycin on myogenic differentiation of MDSPCs isolated from progeroid Ercc1$^{-/\Delta}$ mice. (FIG. 22A) Images of in vitro myogenic differentiation. Cells were immunostained for the terminal differentiation marker, f-MyHC (red). Scale bar=50 μm. (FIG. 22B) Quantification of myogenic differentiation was calculated as the fraction of cells (DAPI blue) expressing f-MyHC (red) from 4 independent MDSPC populations. Error bars indicate the standard deviation. Statistical significance was determined using one-way ANOVA test with Tukey-Kramer post-hoc test. ###p<0.001 versus WT-DMSO, *p<0.001 versus Ercc1$^{-/\Delta}$-DMSO. (FIGS. 22C-22D: Quantitative RT-PCR to measure the expression level of the terminal myogenic differentiation markers MyHC and desmin after myogenic differentiation of MDSPCs isolated from Ercc1$^{-/\Delta}$ and WT mice cultured with and without rapamycin. Error bars indicate the standard deviation. Statistical significance was determined using one-way ANOVA test with Tukey-Kramer or Scheffe's post-hoc test (n=4). ###p<0.001 versus WT-DMSO, p<0.01, ***p<0.001 versus Ercc1$^{-/\Delta}$-DMSO.

(FIG. 23A) Representative images of in vitro chondrogenic differentiation. Micromass cultures were maintained in chondrogenic differentiation medium for 6 days and stained with Alcian blue. Scale bar=3 mm (FIG. 23B) Quantification of Alcian blue staining from 4 independent MDSPC populations. Absorbance of Alcian blue was measured at a wavelength of 595 nm. Error bars indicate the standard deviation. Statistical significance was determined using one-way ANOVA test with Scheffe's post-hoc test. ###p<0.001 versus WT-DMSO, **p<0.01 versus Ercc1$^{-/\Delta}$-DMSO. (FIGS. 23C-23D) Quantitative RT-PCR to measure the expression of the chondrogenic differentiation markers, Collagen Type II (Col2a1) and aggrecan after chondrogenic differentiation of MDSPCs isolated from Ercc1$^{-/\Delta}$ and WT mice cultured with and without rapamycin. Error bars indicate the standard deviation. Statistical significance was determined using one-way ANOVA test with Tukey-Kramer or Scheffe's post-hoc test (n=4). ##p<0.01, ###p<0.001 versus WT-DMSO, *p<0.01, ***p<0.001 versus Ercc1$^{-/\Delta}$-DMSO.

(FIG. 24A) Representative images of in vitro adipogenic differentiation. Cells were stained with AdipoRed (red). Scale bar=20 m. (FIG. 24B) Quantification of AdipoRed staining from 4 independent MDSPC populations. Fluorescence was measured with excitation at 485 nm and emission at 572 nm. Error bars indicate the standard deviation. Statistical significance was determined using Kruskal-Wallis test with Scheffe's post-hoc test. ###$p<0.001$ versus WT-DMSO, *$p<0.001$ versus Ercc1$^{-/\Delta}$-DMSO. (FIGS. 24C-24D) Quantitative RT-PCR to measure the expression of the adipogenic differentiation markers, PPAR γ and LPL (Lipoprotein Lipase) after adipogenic differentiation of MDSPCs isolated from Ercc1$^{-/\Delta}$ and WT mice cultured with and without rapamycin. Error bars indicate the standard deviation. Statistical significance was determined using one-way ANOVA with Tukey-Kramer or Scheffe's post-hoc test (n=4). ###$p<0.001$ versus WT-DMSO, $p<0.01$, ***$p<0.001$ versus Ercc1$^{-/\Delta}$-DMSO.

FIGS. 25A-25C depicts the measurement of the effect of rapamycin on apoptosis in MDSPCs isolated from progeroid Ercc1$^{-/\Delta}$ mice. (FIG. 25A) Representative images of TUNEL assay marking cell death (green). Scale bar=100 μm. (FIG. 25B) Percent of TUNEL positive cells reported from images obtained from 4 independent MDSPC populations. Error bars indicate the standard deviation. ###$p<0.001$ versus WT-DMSO, ***$p<0.001$ versus Ercc1$^{-/\Delta}$-DMSO, Statistical significance was determined using Kruskal-Wallis test with Scheffe's post-hoc test. (FIG. 25C) Immunoblotting to measure the expression of the apoptosis related marker cleaved PARP in MDSPCs isolated from Ercc1$^{-/\Delta}$ and WT mice cultured with and without rapamycin.

(FIG. 26A) The histogram indicates the percent of SA β-gal positive cells from 4 independent MDSPC populations. Error bars indicate the standard deviation. ###$p<0.001$ versus WT-DMSO, ***$p<0.001$ versus Ercc1$^{-/\Delta}$-DMSO. Statistical significance was determined using one-way ANOVA test with Scheffe's post-hoc test. (FIG. 26B) Immunoblotting to measure the expression of senescence related markers p16 and p21 in MDSPCs isolated from Ercc1$^{-/\Delta}$ and WT mice cultured with and without rapamycin.

DETAILED DESCRIPTION OF THE INVENTION

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. All patents and publications cited in this specification are incorporated by reference in their entirety.

For convenience, certain terms used in the specification, examples and claims are collected here. Unless otherwise defined, all technical and scientific terms used herein have the same meaning as commonly understood by one of ordinary skill in the art to which this invention pertains.

The present invention relates to at least in part on the finding that allogeneic or autologous stem/progenitor cells and/or factors secreted or released from functional stem/progenitor cells were able to restore or rejuvenate function of adult stem cells in mammals whose endogenous adult stem/progenitor cells are depleted, damaged, and/or dysfunctional. Accordingly, the invention provides methods of restoring or rejuvenating stem/progenitor cell function in mammals. The present invention is based on the discovery that when functional stem/progenitor cells (e.g., adult stem/progenitor cells) are administered to a mammal, these cells secrete or release factors that restore or rejuvenate the function of endogenous adult stem/progenitor cells that are depleted, damaged, and/or dysfunctional via paracrine means.

Figure 1A:
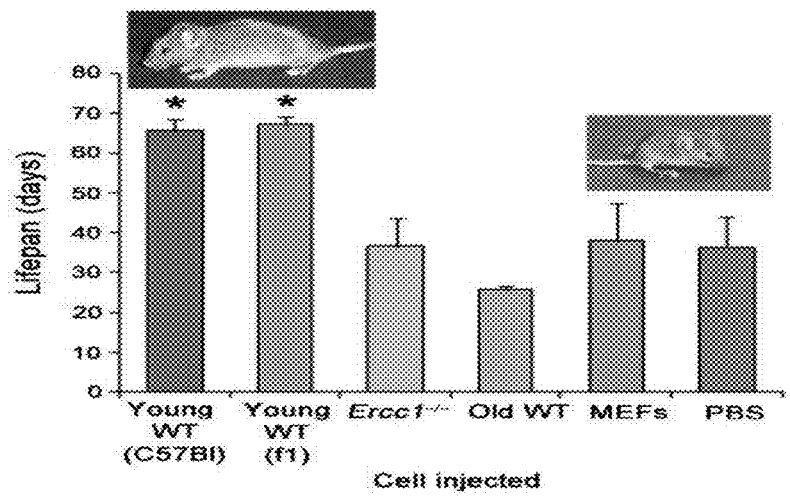
FIGS. 1A-1B depicts measurement of the impact of MDSPC transplantation on the lifespan and healthspan of progeroid mice. (a) (FIG. 1A) $2\text{-}4 \times 10^5$ MDSPCs per gram body-weight were injected into the peritoneal cavity of 17 day-old $Ercc1^{-/-}$ mice and lifespan measured. The median lifespan of $Ercc1^{-/-}$ mice is 21 days; the maximum is 28 days. (See Niedernhofer et al. Nature 444, 1038-2043 (2006) (incorporated by reference herein by reference)). The lifespan of $Ercc1^{-/-}$ mice injected with two independent MDSPC populations isolated from young WT mice were compared to $Ercc1^{-/-}$ mice injected with vehicle only (PBS), an equivalent number of WT mouse embryonic fibroblasts (MEFs), or MDSPCs isolated from old WT or progeroid $Ercc1^{-/-}$ mice. Reported is the average lifespan from 4-10 mice injected per treatment group. Error bars indicate s.e.m. *$P<0.05$, Dunn's test comparing the WT groups with all other treatment groups. (b) (FIG. 1B) $2\text{-}4 \times 10^5$ MDSPCs per gram body-weight were injected into the peritoneal cavity of 7 wk-old $Ercc1^{-/\Delta}$ mice and again at 13 wks of age. The age at onset of the characteristic, spontaneous, aging-related symptoms seen in $Ercc1^{-/\Delta}$ mice was measured (MDSPC-treated mice diamonds) and compared to mice injected with vehicle only (PBS; squares). Reported is the average age at onset of each progeroid symptom in wks±s.d. (n=8 mice per treatment group). The aging score is calculated as the fraction of symptoms that were delayed in a single $Ercc1^{-/\Delta}$ mice injected with young WT-MDSPCs compared to an age and sex-matched mouse (usually a littermate) injected with PBS. The black bars denote the average aging score for each group (***$P<0.0008$, Student's t-test).

Transplantation of functional autologous or allogeneic stem/progenitor cells (e.g., adult stem/progenitor cells) into hosts having dysfunctional, damaged, and/or depleted adult stem/progenitor cells (e.g., MDSPCs), and/or administration of secreted or released factors isolated from stem/progenitor cells (e.g., adult stem/progenitor cells), can lead to a significant extension of healthspan and/or lifespan (see FIG. 1A).

The loss of adult stem cell function directly contributes to various aging-related phenotypes. Therefore, the administration of isolated stem/progenitor cells (and/or factors released from such cells) into a mammal having dysfunctional and/or depleted adult stem/progenitor cells can be used to increase lifespan and/or improve health or healthspan of the mammal.

Those skilled in the art will recognize that any stem/progenitor cells can be used in accordance with the methods and composition of the instant invention. For example stem/progenitor cells can include, by way of non-limiting example, skeletal muscle-derived stem/progenitor cells (MDSPCs), hematopoietic stem/progenitor cells, neural stem/progenitor cells, heart-derived stem/progenitor cells, intestinal stem/progenitor cells, mesenchymal stem/progenitor cells, endothelial stem/progenitor cells, epithelial stem/progenitor cells, olfactory adult stem/progenitor cells, neural crest stem/progenitor cells, testicular stem/progenitor cells, embryonic stem cells, placental derived stem/progenitor cells, amniotic fluid-derived stem/progenitor cells, cord blood stem/progenitor cells, and/or inducible pluripotent stem cells.

Adult stem cells hold great promise for regenerative medicine. Stem cells isolated from adult organisms have significant advantages over embryonic and fetal stem cells as therapeutic modalities. First, adult stem cells by-pass the substantial regulatory burden that accompanies the use and study of cells isolated from perinatal organisms. Second, adult stem cells offer the possibility of autologous therapy. Using cells isolated from a patient to treat only that patient eliminates the risk of an immune rejection that could attenuate the therapeutic benefit or worse cause significant side effects. In addition, autologous approaches for cell-based therapies will accelerate the path to the clinic.

Adult stem cells have been isolated from the bone marrow, brain, muscle, fat, skin, and gut. However, MDSPCs offer several advantages over other adult stem cell populations for therapeutic applications. First, skeletal muscle is relatively easy to access, unlike, for example, brain and bone marrow. Second, a relatively small amount of tissue is necessary to isolate a sufficient number of stem cells for treatment purposes. Third, functional MDSPCs can be expanded substantially ex vivo, which minimizes the amount of muscle that must be excised from a patient, and also offers the possibility of treating a patient multiple times after a single procedure to isolate stem cells. Fourth, there is evidence that MDSPCs isolated from older organisms, which have lost their potency, can be rejuvenated to behave more like MDSPCs isolated from young adults. This means that even the elderly may be eligible for autologous therapy. Fifth, it is established that MDSPCs can be transduced with retroviral vectors expressing novel genes while maintaining their stem-like properties. MDSP-like cells isolated from humans show high regenerative potential in skeletal and cardiac muscle. Thus, MDSPCs may potentially be used to treat inherited diseases of muscle degeneration, for example muscular dystrophies. MDSPCs can differentiate into myogenic, osteogenic, chondrogenic, adipogenic, neural, endothelial, and hematopoietic cells. Therefore, MDSPCs may be useful for treating degenerative diseases of multiple organ systems. Finally, MDSPCs appear to elicit a therapeutic benefit, at least in part, by secreting factors that promote host rejuvenation. Thus, therapeutic benefits may be achieved with fewer cells.

MDSPCs have been used to improve bone healing, cartilage repair, cardiac ischemia, urinary incontinence, and muscular injury including muscular dystrophy. Although MDSPCs are not a well-defined, homogenous cell type, their tremendous potential for treating a wide spectrum of traumatic and degenerative changes, supports the continued development and analysis of MDSPCs.

The musculoskeletal system undergoes degenerative changes with aging. MDSPCs are isolated from skeletal muscle, a tissue that universally declines in mass and function with aging. Cells isolated from primary muscle tissue contain mixture of fibroblasts, myoblasts, adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al. (incorporated herein by reference). Cells that are slow to adhere tend to be morphologically round, express high levels of desmin, and have the ability to fuse and differentiate into multinucleated myotubes U.S. Pat. No. 6,866,842 of Chancellor et al.). A subpopulation of these cells was shown to respond to recombinant human bone morphogenic protein 2 (rhBMP-2) in vitro by expressing increased levels of alkaline phosphatase, parathyroid hormone dependent 3',5'-cAMP, and osteogenic lineage and myogenic lineages. (See U.S. Pat. No. 6,866,842 of Chancellor et al.; T. Katagiri et al., 1994, *J. Cell Biol.*, 127:1755 1766) (incorporated herein by reference).

MDSPCs have a capacity for long-term proliferation, are resistant to oxidative and inflammatory stress, display multilineage differentiation, self-renew, induce neovascularization, and stimulate regeneration of bone, skeletal and cardiac muscles. MDSPCs likely reside in the perivascular niche. These characteristics raise the possibility that the loss of MDSPCs or related perivascular progenitor cells could contribute to sarcopenia, osteoporosis and other degenerative diseases associated with aging.

For MDSPC-based treatments, a skeletal muscle explant is preferably obtained from an autologous or heterologous human or animal source. An autologous animal or human source is more preferred. MDSPC compositions are then prepared and isolated as described herein. To introduce or transplant the MDSPCs and/or compositions comprising the MDSPCs according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, as an alternative to fetal bovine serum suspensions, MDSPCs for administering to a subject can comprise $10^8$ to $10^9$ cells/ml in a sterile solution of complete medium, modified to contain the subject's serum. Alternatively, MDSPC suspensions can be in serum-free, sterile solutions, such as cryopreservation solutions (CELOX™ Laboratories, St. Paul, Minn.). The MDSPC suspensions can then be introduced e.g., via injection, into one or more sites of the donor tissue.

In another embodiment, the invention also provides methods and compositions for restoring or rejuvenating adult stem/progenitor cell function in a mammal for treating, delaying, preventing, or ameliorating one or more symptoms associated with aging, dystonia, kyphosis, ataxia, sarcopenia, incontinence, lethargy, and/or trembling.

Those skilled in the art will recognize that, in accordance with the instant invention, isolated stem/progenitor cells, or secreted or released factors isolated from such stem/progenitor cells, promote neovascularization of a tissue in a mammal. For example, the tissue for neovascularization may be selected from bone, skeletal muscles, cardiac muscles, brain, kidney, spinal cord, nervous system, pancreas, islets, liver, bladder, ureter, bone marrow, ligaments, tendons, cartilage, and/or any combination(s) thereof.

Additionally (or alternatively), administration of isolated stem/progenitor cells, or secreted or released factors isolated from such stem/progenitor cells promote tissue regeneration in the mammal. By way of not limiting example, the tissue being regenerated may include bone, skeletal muscles, cardiac muscles, brain, kidney, spinal cord, nervous system, pancreas, islets, liver, bladder, ureter, bone marrow, ligaments, tendons or cartilage, and/or any combination(s) thereof.

Accordingly, isolated stem/progenitor cells (e.g., adult stem/progenitor cells), or isolated secreted or released factors from such stem/progenitor cells can be administered to a mammal in order to stimulate regeneration of bone, skeletal muscles, cardiac muscles, brain, kidney, spinal cord, nervous system, pancreas, islets, liver, bladder, ureter, bone marrow, ligaments, tendons, cartilage, and/or any combinations thereof.

XFE progeroid syndrome is caused by mutations in XPF (xeroderma pigmentosum complementation group F) and characterized by dramatically accelerated aging of the epidermal, hematopoietic, endocrine, hepatobiliary, renal, nervous, musculoskeletal and cardiovascular systems. XPF encodes one subunit of an endonuclease that together with its essential binding partner ERCC1 (excision repair cross complementation group 1) participates in numerous DNA repair mechanisms. XFE progeroid syndrome was modeled in the mouse by mutation of the mErcc1 locus to titrate expression of ERCC1-XPF. $Ercc1^{-/-}$ mice with undetectable levels of ERCC1-XPF have a severely reduced lifespan of 1 month while $Ercc1^{-/\Delta}$ mice, expressing 10% of the normal level of ERCC1-XPF have a lifespan of 7 months. Both strains faithfully mimic the systemic accelerated aging of XFE progeroid syndrome and demonstrate a highly significant correlation with naturally aged mice at the level of histopathology, pathophysiology and genome-wide transcriptional reprogramming.

Isolated stem/progenitor cells or isolated secreted or released factors from such stem/progenitor cells can be administered to a mammal in order to treat, prevent, or reverse progeria or related syndromes in the mammal. Specifically, upon administration, the one or more secreted or released regulatory factors treat, prevent, or reverse one or more symptoms of progeria or related syndromes (e.g., a progeroid like syndrome) in the mammal. For example, the mammal may carry a Xeroderma pigmentosum complement group F mutation.

Functional stem/progenitor cells, such as MDSPCs, isolated from young or aged adult mammals can be administered to the tissues of the recipient organism of interest, including humans and non-human animals, as a pharmaceutically or physiologically acceptable preparation or composition containing a physiologically acceptable carrier, excipient, or diluents. By way of non-limiting example, MDSPC-containing composition can be prepared by re-suspending the cells in a suitable liquid or solution such as sterile physiological saline or other physiologically acceptable injectable aqueous liquids. The amounts of the components to be used in such compositions or preparations can be routinely determined by those of ordinary skill in the art.

The stem/progenitor cells or compositions thereof can also be administered by placement of the cell suspensions onto absorbent or adherent material, i.e., a collagen sponge matrix, and insertion of the cell-containing material into or onto the site of interest. Alternatively, the stem/progenitor cells can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the stem/progenitor cells can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e., blood) of the recipient. Non-limiting examples of excipients suitable for use include, water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art. (See D. J. Watt et al., 1984, Clin. Exp. Immunol. 55:419; D. Faustman et al., 1991, *Science* 252: 1701).

Consistent with the present invention, the stem/progenitor cells can be administered to body tissues, including bone, epithelial tissue (i.e., skin, lumen, etc.), connective tissue (i.e., adipose, cartilage, ligament, lymph, etc.), muscle tissue (i.e., skeletal/striated or smooth muscle), and/or various organ tissues such as those organs that are associated with the digestive system (i.e., mouth, tongue, esophagus, stomach, liver, pancreas, gall bladder, intestine, anus, etc.), cardiovascular system (i.e., heart, veins, arteries, capillaries, etc.), respiratory system (i.e., lungs, trachea, etc.), reproductive system (i.e., vas deferens, scrotum, testes, penis, fallopian tubes, vagina, clitoris, uterus, breasts, ovaries, vulva, etc.), urological system (i.e., bladder, urethra, ureter, kidneys, etc.), and nervous system (i.e., brain, spinal cord, nerves, etc.).

Any suitable dose of stem/progenitor cells can be administered. For example, between about $1$-$5\times10^5$ and about $1$-$1.5\times10^6$ stem/progenitor cells per gram of body weight of a mammal can be administered. In one embodiment, about $2\times10^5$ to about $5\times10^5$ stem/progenitor cells per gram of body weight of a mammal is administered for restoring adult stem/progenitor cell function. When administered via collagen sponge matrix, about $0.5$-$1.0\times10^6$ stem/progenitor cells can be administered. Consistent with the Examples disclosed herein, a skilled practitioner can modulate the amounts and methods of stem/progenitor cells-based treatments according to requirements, limitations, and/or optimizations determined for each case.

In any of the methods and/or compositions described herein, any stem/progenitor cell can be used. By way of non-limiting example these may include skeletal muscle-derived stem/progenitor cells (MDSPCs), hematopoietic stem/progenitor cells, neural stem/progenitor cells, heart-derived stem/progenitor cells, intestinal stem/progenitor cells, mesenchymal stem/progenitor cells, endothelial stem/progenitor cells, epithelial stem/progenitor cells, olfactory adult stem/progenitor cells, neural crest stem/progenitor cells, testicular stem/progenitor cells, embryonic stem cells, placental derived stem/progenitor cells, amniotic fluid-derived stem/progenitor cells, cord blood stem/progenitor cells, and/or inducible pluripotent stem cells. In a preferred embodiment, the isolated adult stem/progenitor cells are MDSPCs.

Surprisingly, the administration of isolated stem/progenitor cells into a mammal resulted in an increase in body weight in the mammal. For example, body weight of a mammal may be increased between 1-15, 2-16, 3-17, 4-18, 5-19, 6-20, 7-21, 8-22, 9-23, 10-24, 11-25, 12-26, 13-27, 14-28, 15-29, 16-30, 1-30, or 2-40 grams. The present invention provides that body-mass index (BMI) of a mammalian subject would increase from <18.5 in an adult to about 18.5-24.9. The percent increase in body mass may be between about 5% and 150% (e.g., 5, 10, 15, 20, 25, 30, 35, 40, 45, 50, 55, 60, 65, 70, 75, 85, 90, 95, 100, 105, 110, 115, 120, 125, 130, 135, 140, 145, or 150% (or more)).

The invention also provides compositions containing one or more secreted or released regulatory factors isolated from mammalian stem/progenitor cells (e.g., adult stem/progenitor cells). In some embodiments, these compositions can be administered as pharmaceutical compositions containing the one or more regulatory factors secreted or released from the isolated stem/progenitor cells and one or more pharmaceutically acceptable excipients. For example, the one or more secreted or released regulatory factors can be peptides, proteins, RNA, microRNAs, small non-coding RNAs, carbohydrates, lipids, hormones, and/or mixtures thereof.

In one embodiment of the current invention, one or more secreted or released regulatory factors isolated from mammalian adult stem/progenitor cells can include, for example: RBP-JK inhibitory factor, Stanniocalcin-1, Wnt3a, KLOTHO, CCL11, miRNA-489, VEGF, HGF, IGF, microvesicles or exosomes, and/or Her-2/neu (ERBB2/c-erbB-2).

Likewise, additional factors that may be secreted and/or released in mammalian adult stem/progenitor cells can include, but are not limited to, one or more of: curHer-2/neu (ERBB2/c-erbB-2), osteocalcin, stromelysin-1, prostate specific antigen, human sodium-iodide symporter, H19, IF-1, IGF-2, thymosin β15, T cell factor, cartilage-derived retinoic acid-sensitive protein, insulin, PEG-3, telomerase reverse transcriptase, melanoma differentiation associated gene-7, prostasin, telomerase catalytic subunit; cyclin-A, midkine; c-erbB-2, prostate-specific membrane antigen, p51, telomerase RNA, prostatic acid phosphatase, $PCA3_{dd3}$, DF3/MUC1, hex II, cyclooxygenase-2, super PSA, skp2, PRL-3, CA125/M17S2, IAI.3B, CRG-L2, TRPM4, RTVP, TARP, telomere reverse transcriptase, A4 amyloid protein, amyloid β-protein precursor, precursor of the Alzheimer's Disease A4 amyloid protein, neuropeptide FF, endoplasmic reticulum stress elements, urocortin II, tyrosine hydroxylase, complement factor 3; serum amyloid A3, tissue inhibitor of metalloproteinase-3 (TIMP-3), p75 tumor necrosis factor receptor, tumor necrosis factor-a, peroxisome proliferator activated receptor/IIA-1 nonpancreatic secreted phospholipase A2, SOCS-3, SR-BI, Ob, site-1 protease, TIGR, VL30, excitatory amino acid transporter-2, MDTS9, LIM, pyrroline 5-carboxylate reductase, SIM2, Bax, fas, bbc3, PINK-1, troponin T, myoD, actin, smooth muscle 22α, trophin, myostatin, smooth muscle myosin heavy chain, cardiac ankyrin repeat protein, MLP, smoothelin, MYBPC3, Tα1 α-tubulin, intercellular adhesion molecule-4 (ICAM-4), γ-aminobutyric acid type A receptor β1 subunit, neuronal nicotinic acetylcholine receptor β2-subunit, presenilin-1, calcium-calmodulin-dependent kinase IIα, CRF2α receptor, nerve growth factor, GLP-2 receptor, type I transglutaminase, K14, stearoyl-CoA desaturase, megsin, prolactin, GDF-9, PSP94, NRL, NGAL, long whey acidic protein, mammary associated amyloid A, endothelin-1, serglycin, platelet-endothelial cell adhesion molecule-1 (PECAM-1), Tie receptor tyrosine kinase, KDR/flk-1, endoglin, CCR5, CD11d, platelet glycoprotein IIb, preproendothelin-1, interleukin-18 binding protein, CD34, Tec tyrosine kinase, AC133, MLH1, MSH2, MSH6, PMS1, APC, LEF-1, F2 receptor, TGF-β type II receptor, EYA4, PCA3, K2, PROST 03, PCAM-1, PCADM-1, PCA3dd3, PCAV, PAcP, ATBO, CSA-1, SYG972, Urb-ctf, BCU399, TBX2, Cyr61, DIAPH3, Human aspartyl (asparaginyl) beta-hydroxylase, BEHAB, IL-8, BLSA, BP1, DAP-kinase, HOXA9, ARP, Nbk, CD43, β7-hcG, β6-hCG, β6e-hCG, β5-hCG, β8-hcG, β3-hCG, MTA1s, Old-35, Old-64, LAGE-1, CIF150/hTAFII150, P65 oncofetal protein, Telomerase, CYP1B1, 14-3-30, NES1, CAR-1, HMGI, MAG, ELL2, Ephrin B2, WAF1, CIF130, C35, BMP2, BUB3, Polymerase kappa, EAG1, EAG2, HMGI, HLTF, Barx2, Cables, Pp 32r1, BMP4, TS10q23.3, Nuclear spindle-associating protein, PFTAIRE, SEMA3B, MOGp, Fortilin, IGFBP-3, Polyhomeotic 2, PNQALRE, SCN5A, miR15, miR16, Headpin, PAOh1/SMO, Hippo, Mst2, PSMA-like, JAB 1, NF-AT, P28ING5, MTG16, ErbB-2, HDAC9, GPBP, MG20, KLF6, ARTS 1, Dock 3, Annexin 8, MH15, DELTA-N p73, RapR6, StarD10, Ciz1, HLJ1, RapR7, A34, Sef, Killin, SGA-IM, TGFβ Type II receptor, GCA-associated genes, PRV-1, Vezfl, MLP, VEGI, PRO256, AOP2, Remodelin, Phosphodiesterase 4D, Prostaglandin receptor subtype EP3, CARP, HOP, PLTP, UCP-2, FLJ11011, Codanin-1, Resistin, Archipelin, Neuronatin, Ncb5or, 7B2, PTHrP, PEX, KChIP1, SLIT-3, CX3CR1, SMAP-2, IC-RFX, E2IG4, UCP2, Ob receptor, Ob, Dp1, NRG-1, Synapsin III, NRG1AG1, AL-2, Proline dehydrogenase, MNR2, ATM, Ho-1, CON202, Ataxin-1, NR3B, NIPA-1, DEPP, adrenomedullin, csdA, Inf-20, EOPA, SERT, FRP-1, Serum amyloid A, BMP2, BMPRiA, ACLP, Resistin-like molecule β, Dlg5, TRANCE, Matrilin-3, Synoviolin, HIV LTR, SHIVA, EBI 1, EBI 2, EBI 3, NM23 family, Eps8, Beta-10, Hair follicle growth factor, Corneodesmosin, GCR9, Bg, FGF23, BBSR, MIC-1, MIA-2, IL-17B, Formylglycine generating enzyme, LPLA2, CXCL10, HFE2A, Notch-regulated secreted factor, Hes-1, TCF3, SLC11A1, CD14, TRL4, CSPG, and/or IL0.

Those skilled in the art will recognize that administration of an effective amount of the composition containing one or more regulatory factors secreted or released from one or more isolated mammalian stem/progenitor cells (e.g., adult stem/progenitor cells) to a mammal, wherein endogenous adult stem/progenitor cells in skeletal muscle of the mammal are depleted or dysfunctional (i.e., due to age), can be used to extend lifespan and/or improve health of said mammal.

Also provided are compositions and methods for restoring or rejuvenating adult stem/progenitor cell function by administering a bioactive composition containing one or more regulatory factors. Those skilled in the art will recognize that the bioactive compositions of the present invention consist of, consist essentially of, or comprise one or more regulatory factors. Exemplary bioactive compositions can include receptor, ligands, transcription factors, and/or regulatory molecules.

Receptor ligands include, but are not limited to, vascular endothelial growth factor (VEGF (A-F)), fibroblast growth factors (acidic and basic FGF 1-10), granulocyte-macrophage colony-stimulating factor (GM-CSF), insulin, insulin growth factor or insulin-like growth factor (IGF), insulin growth factor binding protein (IGFBP), placenta growth factor (PIGF), angiopoietin (Ang1 and Ang2), platelet-derived growth factor (PDGF), hepatocyte growth factor (HGF), transforming growth factor (TGF-α, TGF-β, isoforms 1-3), platelet-endothelial cell adhesion molecule-1 (PECAM-1), vascular endothelial cadherin (VE-cadherin), nitric oxide (NO), chemokine (C-X-C motif) ligand 10 (CXCL10) or IP-10, interleukin-8 (IL-8), hypoxia inducible factor (HIF), monocyte chemotactic protein-1 (MCP-1), vascular cell adhesion molecule (VCAM), ephrin ligands (including Ephrin-B2 and -B4).

Transcription factors include, but are not limited to, HIF-1α, HIF-1β and HIF-2α, Ets-1, Hex, Vezfl, Hox, GATA, LKLF, COUP-TFII, Hox, MEF2, Braf, Prx-1, Prx-2, CRP2/SmLIM and GATA family members, basic helix-loop-helix factors and their inhibitors of differentiation.

This invention also provides methods for identifying one or more candidate compounds that modulate expression of one or more secreted or released regulatory factors in a population of isolated mammalian stem/progenitor cells (e.g., adult stem/progenitor cells), where the method involves the steps of (but is not limited to) exposing the population of stem/progenitor cells to the one or more candidate compounds; determining the expression of the one or more regulatory factors in the population of stem/progenitor cells exposed to the candidate compounds and in a control population of stem cells that are not exposed to the candidate compound; and comparing the expression of the one or more regulatory factors in the exposed population of stem/progenitor cells with expression in the control population of stem/progenitor cells, thereby identifying one or more candidate compounds that modulate expression of the one or more secreted regulatory factors.

In any of these screening methods, when the expression of one or more secreted or released regulatory factors is greater in the exposed population compared to the control population, the one or more candidate compound increases expression of the one or more secreted or released regulatory factors.

Likewise, when the expression of one or more secreted or released regulatory factors is lower in the exposed population compared to the control population, the one or more candidate compound decreases expression of the one or more secreted or released regulatory factors.

Combination Therapy with One or More mTOR Inhibitors mTOR (also known as target of rapamycin or FK506 binding protein 12-rapamycin associated protein 1 (FRAP1)) is a serine/threonine protein kinase that helps to integrate cellular activities in response to nutrients, stress, and extracellular signals including hormones and locally produced growth factors (see Stanfel et al., 2009, *Biochim Biophys Acta*, 1790:1067-1074; Martin et al., 2005, *Curr Opin Cell Biol*, 17:158-166). The mTOR signaling pathways play different roles during development and adulthood in metazoans (see Wullschleger et al., 2006, *Cell*, 124:471-484). During development, mTOR primarily controls growth, whereas in adults, mTOR controls aging and other aspects of nutrient-related physiology (see Ramos et al., 2012, *Science Translational Medicine* 4). Abnormally increased activation of the mTOR pathway may lead to stem cell exhaustion and accelerating aging (see Chen et al., 2009, *Sci Signal* 2:75; Gan et al., 2009, *Cell Cycle*, 8:1003-1006; and Chen et al., 2008, *J Exp Med*, 205:2397-2408).

mTOR also regulates protein synthesis through the phosphorylation of 4E-BP1 and p70-S6 (see Ma et al., 2009, *Nat Rev Mol Cell Biol*, 10:307-318). p70-S6 is among the major downstream targets of the mTOR pathway and deletion of the p70-S6 gene increases lifespan in mice and retards the aging of bone, the immune system, and skeletal muscle. Inhibition of mTOR signaling may prevent or delay some aging processes due to depleted or dysfunctional MDPSCs through regulation of p70-S6.

Another important function of the mTOR signaling pathway is the regulation of autophagy, a process in which the cell degrades damaged or excess cellular components—from individual proteins and protein aggregates to whole organelles—through the lysosomal machinery of the cell. Recent studies provided evidence that insufficient autophagy is implicated in normal aging. Stem cells lose their capacity to self-renew and differentiate when autophagy is disrupted, hence the cells essentially lose their 'stemness' (see Salemi et al., 2012, *Cell Research* 22:432-435). Inhibition of mTOR signaling slows the progeric aging process. Thus, inhibition of mTOR signaling may prevent the loss of differentiation potential through increased autophagy.

In any of the methods described herein, isolated autologous or allogeneic stem/progenitor cells (e.g., adult stem/progenitor cells) may be administered in combination with one or more mTOR inhibitors to the mammal, wherein endogenous adult stem/progenitor cells of the mammal are depleted or dysfunctional, and wherein the one or more mTOR signaling inhibitors restore or rejuvenate the adult stem cell function. The one or more mTOR inhibitors may be administered prior to, simultaneously with, or following administration of the isolated stem/progenitor cells.

In any of the methods and/or compositions described herein, one or more mTOR inhibitor may be used for preventing or slowing aging and/or preventing stem cell exhaustion or loss of differentiation potential of MDSPCs.

The invention also provides compositions that additionally contain one or more regulatory factors secreted or released from isolated mammalian stem/progenitor cells, and/or one or more mTOR inhibitors. Methods are also provided for extending lifespan of a mammal, or improving health of a mammal, or both, by administering an effective amount of the composition containing one or more regulatory factors secreted or released from isolated mammalian stem/progenitor cells (e.g., adult stem/progenitor cells) and one or more mTOR inhibitor to a mammal, wherein endogenous adult stem/progenitor cells in the mammal (e.g., in the skeletal muscle of the mammal) are depleted or dysfunctional due to age, and wherein the composition extends lifespan and/or improves health of said animal.

As used herein, an mTOR inhibitor may be a peptide, RNA, microRNA, hormone, or small molecule that decreases mTOR activity. Decreases in mTOR activity can be readily measured by one skilled in the art, and may include decreased phosphorylation of downstream mTOR targets (e.g., 4EBP1 and p70-S6) and/or decreased assembly into mTOR Complex 1 (mTORC1) or mTOR Complex 2 (mTORC2).

MTOR inhibitors may include, but are not limited to, one or more of: sirolimus (rapamycin, rapamune), everolimus (ZORTRESS®, RAD001), temsirolimus (TORISEL®, CCI-779), deforolimus (AP23573, MK-8669, RIDAFOROLIMUS®), Torin1, Torin2, PP242, KU0063794, WYE-687 dihydrochloride, WYE-354, WYE-125132, WAY-600, AZD8055, AZD2014, OSI-027, PP242, PF04691502, PF05212384, INK128 (MLN0128), as well as derivatives, analogs, and/or combination(s) thereof.

Methods of Isolation of MDSPCs

The present invention provides MDSPCs comprised of early progenitor cells (also termed muscle-derived progenitor cells or muscle-derived stem cells herein) that show long-term survival rates following transplantation into body tissues, preferably soft tissues. To obtain the MDSPCs of this invention, a muscle explant, preferably skeletal muscle, is obtained from an animal donor, preferably from a mammal, including humans. This explant serves as a structural and functional syncytium including "rests" of muscle precursor cells. (See T. A. Partridge et al., 1978, Nature 73:306 8; B. H. Lipton et al., 1979, Science 205:12924).

In one embodiment, a preplating procedure may be used to differentiate rapidly adhering cells from slowly adhering cells (MDSPCs).

Populations of rapidly adhering cells (PP1-4) and slowly adhering, round MDSPCs (PP6), were isolated and enriched from skeletal muscle explants and tested for the expression of various markers using immunohistochemistry to determine the presence of pluripotent cells among the slowly adhering cells. (See Example 1 in U.S. Pat. No. 6,866,842 (filed Apr. 30, 1999)). The PP6 cells expressed myogenic markers, including desmin, MyoD, and Myogenin. The PP6 cells also expressed c-met and MNF, two genes which are expressed at an early stage of myogenesis. (See J. B. Miller et al., 1999, Curr. Top. Dev. Biol. 43:191 219). The PP6 showed a lower percentage of cells expressing M-cadherin, a satellite cell-specific marker (see A. Irintchev et al., 1994, Development Dynamics 199:326 337), but a higher percentage of cells expressing Bcl-2, a marker limited to cells in the early stages of myogenesis (see J. A. Dominov et al., 1998, J. Cell Biol. 142:537 544). The PP6 cells also expressed CD34, a marker identified with human hematopoietic progenitor cells, as well as stromal cell precursors in bone marrow. (See R. G. Andrews et al., 1986, Blood 67:842 845; C. I. Civin et al., 1984, J. Immunol. 133:157 165; L. Fina et al, 1990, Blood 75:2417 2426; P. J. Simmons et al., 1991, Blood 78:2848 2853). The PP6 cells also expressed Flk-1, a mouse homologue of human KDR gene which was recently identified as a marker of hematopoietic cells with stem cell-like characteristics. (See B. L. Ziegler et al., 1999, Science 285:1553 1558). Similarly, the PP6 cells expressed Sca-1, a marker present in hematopoietic cells with stem cell-like characteristics. (See M. van de Rijn et al., 1989, Proc. Natl. Acad. Sci. USA 86:4634 8; M. Osawa et al., 1996, J. Immunol. 156:3207 14). However, the PP6 cells did not express the CD45 or c-Kit hematopoietic stem cell markers. (See L K. Ashman, 1999, Int. J. Biochem. Cell. Biol. 31:1037 51; G. A. Koretzky, 1993, FASEB J. 7:420 426).

The PP6 population of muscle-derived progenitor cells expresses the desmin, CD34, and Bcl-2 cell markers. The PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers such as desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

In another embodiment, the rapidly adhering cells and slowly adhering cells (MDSPCs) are separated from each other using a single plating technique. First, cells are provided from a skeletal muscle biopsy. The biopsy need only contain about 100 mg of cells. Biopsies ranging in size from about 50 mg to about 500 mg are used according to both the pre-plating and single plating methods of the invention. Further biopsies of 50, 100, 110, 120, 130, 140, 150, 200, 250, 300, 400 and 500 mg are used according to both the pre-plating and single plating methods of the invention. In one embodiment, the tissue from biopsy is processed within 24 hours after it is procured.

The tissue from the biopsy is then stored for 1 to 30 days. This storage is at a temperature from about room temperature to about 4° C. This waiting period causes the biopsied skeletal muscle tissue to undergo stress. While this stress is not necessary for the isolation of MDSPCs using this single plate technique, using the wait period results in a greater yield of MDSPCs.

Tissue from the biopsies is minced and centrifuged. The pellet is resuspended and digested using a digestion enzyme. Enzymes that may be used include collagenase, dispase or combinations of these enzymes. After digestion, the enzyme is washed off of the cells. The cells are transferred to a flask in culture media for the isolation of the rapidly adhering cells. Many culture media may be used. Particularly preferred culture media include those that are designed for culture of endothelial cells including Cambrex Endothelial Growth Medium. This medium may be supplemented with other components including fetal bovine serum, IGF-1, bFGF, VEGF, EGF, hydrocortisone, heparin, and/or ascorbic acid. Other media that may be used in the single plating technique include InCell M310F medium. This medium may be supplemented as described above, or used unsupplemented.

The step for isolation of the rapidly adhering cells may require culture in flask for a period of time from about 30 to about 120 minutes. The rapidly adhering cells adhere to the flask in 30, 40, 50, 60, 70, 80, 90, 100, 110 or 120 minutes. After they adhere, the slowly adhering cells are separated from the rapidly adhering cells from removing the culture media from the flask to which the rapidly adhering cells are attached to.

The culture medium removed from this flask is then transferred to a second flask. The cells may be centrifuged and resuspended in culture medium before being transferred to the second flask. The cells are cultured in this second flask for between 1 and 3 days. Preferably, the cells are cultured for two days. During this period of time, the slowly adhering cells (MDSPCs) adhere to the flask. After the MDSPCs have adhered, the culture media is removed and new culture media is added so that the MDSPCs can be expanded in number. The MDSPCs may be expanded in number by culturing them for from about 10 to about 20 days. The MDSPCs may be expanded in number by culturing them for 10, 11, 12, 13, 14, 15, 16, 17, 18, 19 or 20 days. Preferably, the MDSPCs are subject to expansion culture for 17 days.

As an alternative to the pre-plating and single plating methods, the MDSPCs of the present invention can also be isolated by fluorescence-activated cell sorting (FACS) analysis using labeled antibodies against one or more of the cell surface markers expressed by the MDSPCs. (See C. Webster et al., 1988, Exp. Cell. Res. 174:252 65; J. R. Blanton et al., 1999, Muscle Nerve 22:43 50). For example, FACS analysis can be performed using labeled antibodies to directed to CD34, Flk-1, Sca-1, and/or the other cell-surface markers described herein to select a population of PP6-like cells that exhibit long-term survivability when introduced into the host tissue. Additionally, one or more fluorescence-detection labels, for example, fluorescein or rhodamine, can be used for antibody detection of different cell marker proteins.

Another embodiment of the invention provides an optimized method of the pre-plating method, defined herein as the "modified pre-plate method," to isolate stem/progenitor cells from skeletal muscle. The modified pre-plate method separates different populations of myogenic cells based on their propensity to adhere to collagen I-coated surface. Based on their surface markers and stem-like properties, including self-renewal, multi-lineage differentiation, and ability to promote tissue regeneration, the last cell fraction or slowest to adhere to the collagen-coated surface (pre-plate 6; pp6) appear to be early, quiescent progenitor cells termed muscle-derived stem/progenitor cells (MDSPCs). The cell fractions preceding pp6 (pp1-5) are likely populations of more committed (differentiated) cells, including fibroblast- and myoblast-like cells. This technique may be used to isolate MDSPCs from skeletal muscle of humans or mice regardless of age, sex or disease state. However, the yield of MDSPCs varies with age and health. MDSPCs can be used for regeneration of a variety of tissues including bone, articular cartilage, skeletal and cardiac muscle and nerve.

In accordance with the methods and compositions of the invention, MDSPCs from young mice have been demonstrated to extend lifespan and/or improve healthspan in mouse models of accelerated aging through an apparent paracrine/endocrine mechanism.

Using any of the MDSPCs isolation methods described above, MDSPCs that are to be transported, or are not going to be used for a period of time may be preserved using methods known in the art. More specifically, the isolated MDSPCs may be frozen to a temperature ranging from about −25 to about −90° C. Preferably, the MDSPCs are frozen at about −80° C., on dry ice for delayed use or transport. Freezing may be accomplished with any cryopreservation medium known in the art.

Figure 5A:
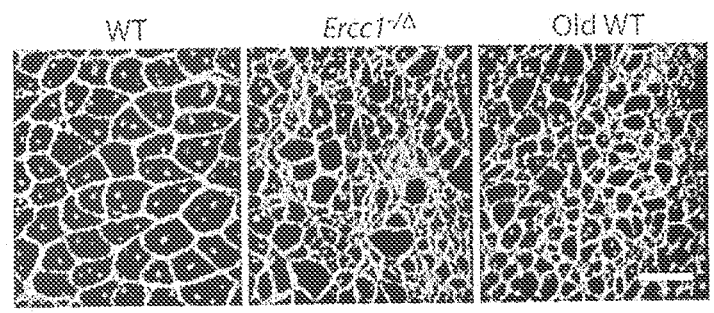
FIGS. 5A-5D depicts measurement of muscle regeneration after injury in old and progeroid mice. To measure muscle stem/progenitor cell function in vivo, cardiotoxin was injected directly into the gastrocnemius muscle of old WT (3 yr-old; n=3), adult WT (18-21 wk-old; n=5), and progeroid Ercc1$^{-/\Delta}$ (21 wk-old; n=2 plus 8 wk-old; n=3) mice to induce muscle injury. Two weeks later, tissues were harvested and stained for dystrophin and nuclei (DAPI).
Figure 5B:
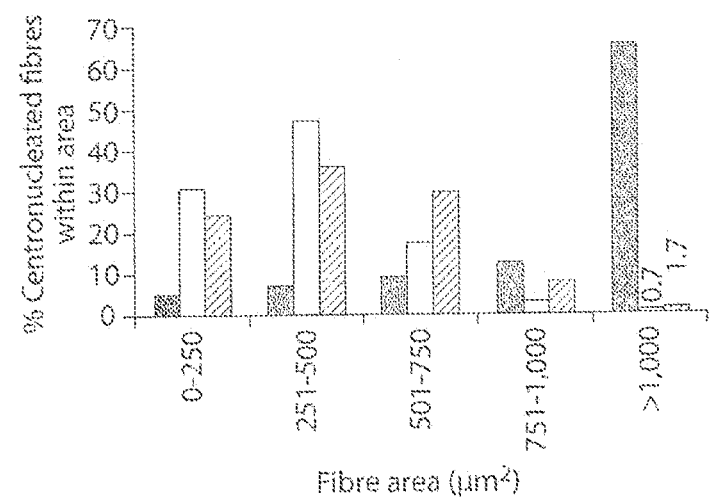

MDSPCs were isolated from old WT mice and mice with accelerated aging using the pre-plate technique. In both mice, cell proliferation and multilineage differentiation is significantly impaired relative to MDSPCs isolated from young WT mice (see FIG. 3D). Furthermore, fewer cells expressing stem/progenitor cell markers are isolated from skeletal muscles of aged and progeroid mice (see FIGS. 4D, 4E), and muscle from aged and progeroid mice has significantly reduced regenerative capacity following injury (see FIG. 5B).

TABLE 1

Comparison of the total area of skeletal muscle regeneration following cardiotoxin injection into the gastrocnemius muscle of mice of the various genotypes.

| Genotype | n | Median area of regeneration ($\mu m^2$) |
| --- | --- | --- |
| WT (8 wks) | 3 | 6708413 |
| Ercc1$^{-/\Delta}$ (8 wks) | 3 | 5250861 |
| WT (18-21 wks) | 5 | 2787460 |
| Ercc1$^{-/\Delta}$ (18 wks) | 2 | 4570307 |
| WT (3 yrs) | 3 | 2698447 |

P = 0.363 (Kruskal-Wallis One Way Analysis of Variance on Ranks difference).

These results establish that, as with neuronal, mesenchymal, hematopoietic, satellite, and adipose stem cells, function of MDSPCs is compromised with aging. The similarity of deficits in MDSPCs from old WT and progeroid mice extends the commonalities between accelerated aging caused by a defect in DNA repair and natural aging. Similar parallels have been found between Hutchinson Gilford progeria syndrome and aging in the MSC compartment.

Determination of the Effect of Increased Oxidative DNA Damage, ROS and/or NF-κB Activity on MDSPCs Function with Aging.

DNA Damage, ROS and NF-κB Activation all Contribute to Stem/Progenitor Cell Dysfunction with Aging.

It has been demonstrated that MDSPCs isolated from the skeletal muscle of naturally aged mice and progeroid ERCC1-deficient mice have a reduced ability to proliferate and differentiate compared to MDSPCs isolated from normal WT littermates. However, what drives stem/progenitor cell dysfunction associated with aging is unclear. Experiments have demonstrated that both accelerated and naturally aged mice have increased oxidative DNA damage in multiple tissues, but whether stem/progenitor cells in aged mice also have a similar increase in oxidative DNA damage is unknown.

Young MDSPCs have been observed to be more resistant to oxidative and inflammatory stress, likely due to their expression of high levels of antioxidants relative to more differentiated myoblasts. In contrast, aged MDSPCs have higher levels of ROS, which appears to contribute to their dysfunction since potent anti-oxidants improve their function. It has also been demonstrated that the transcription factor NF-κB, which is activated by genotoxic, oxidative and inflammatory stress, contributes to MDSPCs dysfunction since genetic and pharmacologic reduction of NF-κB activity improves proliferation and differentiation. The ability of the MDSPCs to proliferate and undergo myogenesis, osteogenesis (functional MDSPCs) and adipogenesis (dysfunctional MDSPCs) is determined for all the treatment regimes.

Finally, the effect of inflammatory stress on MDSPCs is determined by treatment with IL-1β and IL-1α. In addition to the analysis of the effects of inflammatory, genotoxic and oxidative stress on cell autonomous (proliferation and differentiation) and non-autonomous (rescue of function of aged MDSPCs with condition media) in culture, the extent of oxidative DNA damage in MDSPCs isolated from young, old and ERCC1-deficient mice is measured. To determine the role of NF-κB in driving MDSPC dysfunction, similar experiments are performed, but using MDSPCs derived from p65$^{+/-}$ mice or by treating the cells with an IKK inhibitor.

In addition, as controls, MDSPCs are also isolated from the different Ercc1$^{-/\Delta}$ and Ercc1$^{-/\Delta}$/p65$^{+/-}$ mouse strains in carrying mutations in NEMODK, TNF-R$^{-/-}$ and MyD88$^{-/-}$. Different strains of mice are treated with IL-1, menandione, XJB and MEC to examine the role of NF-κB in driving aging in response to oxidative, genotoxic and/or inflammatory stress in vivo. Thus, MDSPCs are isolated from these treated and untreated strains and measure the extent of oxidative DNA damage, apoptosis, senescence, ROS, and NF-κB activation and ability of conditioned media to rescue aged MDSPCs. It is important to note the number of MDSPCs also is examined to determine if specific treatments affect the number of MDSPCs in addition to their function.

MDSPCs isolated from ERCC1-deficient and naturally aged mice exhibit limited proliferation and myogenic differentiation potentials in vitro and in vivo. One of the inherent characteristics of stem cells is their ability to undergo long term self-renewal through cell division. The in vitro proliferation behaviors of the MDSPCs were examined using a robotic time-lapsed microscopic live-cell imaging (LCI) system (Automated Cell, Inc.). The results indicated that the proliferation of MDSPCs isolated from the old WT, Ercc1$^{-/-}$ and Ercc1$^{-/\Delta}$ mice, was significantly impaired relative to MDSPCs isolated from young WT mice. In order to determine the myogenic differentiation capacity of the MDSPCs isolated from ERCC1-deficient and naturally aged mice, MDSPCs were stained for fast myosin heavy chain (f-MyHC), 3 days after cultured in differentiation medium. The degree of myogenic differentiation was significantly reduced in old WT Ercc1$^{-/-}$ and Ercc1$^{-/\Delta}$ MDSPCs relative to young WT MDSPCs (*P<0.001, Kruskal-Wallis ANOVA on ranks). To investigate whether the defects in proliferation and myogenic differentiation observed in the ERCC1-deficient cells in vitro and limit their ability to undergo myogenic differentiation in vivo, MDSPCs from Ercc1$^{-/\Delta}$ and Ercc1+/Δ muscle were injected into the gastrocnemius muscle of 8 week old MDX/SCID mice, a mouse model of Duchenne Muscular Dystrophy (DMD), that lacks dystrophin at the sarcolemma of muscle fibers (MDX) and is also immuno-incompetent (SCID). Fourteen days post-transplantation, the diameter of the regenerated dystrophin-positive myofibers was measured.

The WT MDSPCs fused both together and with the host muscle fibers to form large dystrophin positive myofibers. Conversely, the Ercc1–/Δ MDSPCs appeared not to fuse well with the host muscle fibers since the dystrophin positive regenerated myofibers observed were significantly smaller in diameter as compared to the WT litter mate MDSPCs.

ERCC1-deficient MDSPCs displayed a lower resistance to stress when compared to WT MDSPCs. To test if ERCC1-deficient MDSPCs were hypersensitive to oxidative stress, WT and Ercc1$^{-/-}$ MDSPCs were exposed to 200 μM hydrogen peroxide (oxidative stress) and cell survival determined by counting the number of PI-positive cells in the fluorescent images at each 12 hr time point. WT MDSPCs were able to survive oxidative stress at higher rates than Ercc1$^{-/-}$ and Ercc1$^{-/\Delta}$, with significantly increased cell survival seen at 60 and 72 hours after treatment with hydrogen peroxide (*P<0.05).

MDSPCs Isolated from Naturally Old WT and Ercc1$^{-/\Delta}$ Show Increased Oxidative Stress.

Elevation of ROS, primarily generated by mitochondria in response to cellular damage including DNA damage is implicated in aging. Therefore, the levels of ROS produced by MDSPCs were measured using MitoSOX, a fluorescence dye taken up by mitochondria that react specifically with superoxide anion using LCI system. The preliminary results revealed significant increases in ROS production in MDSPCs isolated from Ercc1$^{-/\Delta}$ in comparison to young WT MDSPCs.

Reduction of NF-κB Improved the Proliferation Potential of MDSPCs and Increased Lifespan of Ercc1$^{-/-}$.

Reducing NF-κB activity by knocking out a single p65 allele (p65$^{+/-}$) improves proliferation and myogenic differentiation of MDSPCs. To examine the role of the NF-κB pathway in mediating age-related histopathology and disease, p65$^{+/-}$ mice were crossed with Ercc1$^{-/-}$ and Ercc1$^{-/\Delta}$ mice to generate Ercc1$^{-/\Delta}$ mice heterozygous for p65. Although these transgenic mice do not differ grossly at birth from Ercc1$^{-/\Delta}$ mice, the reduction of p65 increased lifespan in Ercc1$^{-/-}$ mice and healthspan in Ercc1$^{-/\Delta}$ mice. MDSPCs were isolated from Ercc1$^{-/\Delta}$ mice (16 days) and analyzed cell proliferation by LCI system and Ki67 immuno-staining. Ercc1$^{-/-}$/p65$^{+/-}$ MDSPCs displayed a significant increase in proliferation compared to Ercc1$^{-/-}$ MDSPCs (* P<0.001).

Reduction of NF-κB Enhances the Myogenic Differentiation Potential and Resistance to Stress in MDSPCs Isolated from Naturally Aged Mice.

To determine further whether the NF-κB signaling pathway plays a role in driving age-related stem cell dysfunction, whether pharmacologic inhibition of IKK-β would restore the myogenic potential of aged WT MDSPCs was examined. Strikingly, treatment with 3 mM of the IKKβ inhibitor IV (IKKi) under fusion conditions significantly increased the fusion index of aged MDSPCs. MDSPCs were isolated from 30 month old p65$^{+/-}$ and 24 month old WT mice and compared the myogenic potential of 30 month old p65$^{+/-}$ MDSPCs in vitro to naturally aged WT MDSPCs. The results confirmed that MDSPCs from p65$^{+/-}$ aged mice (30 month) were more myogenic than MDSPCs from 24 month old WT mice. These results support the hypothesis that, in the context of aging, NF-κB/p65 signaling may be dysregulated therefore contributing to the "aged phenotype" of stem/progenitor cells. Furthermore, the preliminary results demonstrated that reduction of NF-κB/p65 improved aged MDSPC survival under oxidative stress conditions as measured by LCI system over a 24 hr period.

Increased DNA Damage in Skeletal Muscle Through Tissue-Specific Inactivation of Ercc1 Will Lead to MDSPCs Dysfunction Through a Non Cell Autonomous Mechanism.

MDSPCs isolated from the skeletal muscle of ERCC1-deficient and aged WT mice are defective in their proliferation and differentiation capacities. Although this is consistent with the concept that the accumulation of damage directly to the stem/progenitor cells (cell autonomous) contributes to the loss of tissue regeneration and homeostasis associated with aging, a potential defect in the stem cell niche or circulating factors could also affect MDSPC function in a non-autonomous manner. Indeed, there is evidence that aging and disease affects the stem cell niche, impacting stem cell function via a non-autonomous mechanism. Similarly, the function of stem/progenitor cells can be adversely affected by factors circulating in the serum of aged mice. Therefore, it remains unclear if aging related loss of adult stem cell function is primarily driven by cell autonomous (increased DNA damage) and/or non-autonomous mechanisms (aged microenvironment or circulating factors).

Thus, the goal is to characterize the mechanism through which MDSPCs become dysfunctional with aging using mouse models of tissue and cell type-specific inactivation of Ercc1. Through tissue-specific knockout of ERCC1, it can be determined whether damage accumulation in one cell type or tissue (e.g. skeletal muscle, endothelial cells) will have a similar effect as observed with MDSPCs from aged and ERCC1-deficient mice. Initially, to determine if there is a systemic effect on driving MDSPC dysfunction with aging, heterochronic parabiosis will be performed.

Aged and Young WT Mice are Paired as Well WT and Ercc1-/Δ Mice.

At different time points, MDSPCs will be isolated from the skeletal muscle of both mice and analyzed for their number and function compared to age matched controls. For these experiments, young C57BL/10J mice that express that express CD45.2 on their leukocytes and aged SJL/J mice that express CD45.1 will be used. Alternatively, young mice expressing eGFP constitutively are paired with either aged or Ercc1-/Δ mice. The use of eGFP or different CD45 alleles will allow for the determination of the host origin of the MDSPCs as well as the extent of chimerism.

In order to determine whether aging of the MDSPCs microenvironment affects MDSPC function, strains of mice with a deletion of ERCC1-specifically in muscle fibers (Cre expressed from a muscle creatine kinase promoter) and in endothelial cells (Cre expressed from the ve-cadherin promoter) are generated. Initially, the extent of damage and angiogenesis in muscle are examined to determine the effect of the tissue specific ERCC1 deletion over time. Then, MDSPCs are isolated from these mice, starting at the time when pathology is typically observed in the skeletal muscle tissue Ercc1$^{-/-}$ in the mice with a tissue specific deletion of ERCC1. The isolated MDSPCs are analyzed for number, extent of proliferation and differentiation as well as for the ability of their conditioned media to rescue aged MDSPCs. In addition, the level of oxidative DNA damage, ROS, senescence and NF-κB activation is also measured. If the parabiosis experiments demonstrate the presence of circulating factors contributing to MDSPC dysfunction with aging, the effect that accelerated aging of a panel of specific tissue and cell types on MDSPC function will be examined. For these experiments, mice with ERCC1 deleted in hepatocytes, 13 cells, immune cells, macrophages, different kidney cell types (podocytes and tubular epithelia) and possibly other tissues are used. Again, MDSPCs are isolated from animals at different ages and analyzed as described above. In this manner it can be determined if MDSPCs with WT ERCC1 becomes dysfunctional through a non cell autonomous mechanism(s).

Preliminary Results Supporting the Dysfunction in Aged MDSPCs Observed in Culture Correlates with Limited Muscle Regeneration after Injury In Vivo.

To determine whether the dysfunction observed in aged/progeroid MDSPCs in culture, can also be observed in vivo, the extent of muscle regeneration between aged/progeroid and young mice utilizing a well-established cardiotoxin injury-induction model was examined. There was a dramatic difference in the average cross-sectional area of the regenerated myofibers in old and progeroid mice compared to young adult mice. In addition, Masson's Trichrome stain revealed increased fibrosis in the muscle of old and progeroid mice in comparison to young WT mice following injury. These results suggest that a loss of function and/or number of MDSPCs in aged/progeroid mice leads to a reduction in muscle regeneration and repair after injury.

Defective Muscle Regenerative Process Observed in Dystrophic Mice Also Correlated with a MDSPCs Defect.

The dystrophin/utrophin double knock out mouse (dKO) model is a far more severely affected and more reliable mouse model of Duchenne muscular dystrophy (DMD). In fact, muscle regeneration and the extent of muscle fibrosis are severe in the dKO skeletal muscle. Like ERCC1-deficient mice, dKO mice have a limited lifespan (6-10 weeks). The dKO mice has also been used as a model of muscle damage to determine if there is a cell non-autonomous effect of the damaged muscle microenvironment on 6 week old, dKO derived MDSPCs compared to aged matched controls. The proliferation kinetics of both populations in culture was examined using LCI system and a significant reduction in the proliferation capacity of the dKO MDSPCs when compared to WT MDSPCs (*P<0.01) was observed. The result of the myogenic differentiation assay showed that the degree of myogenic differentiation (fast MyHC-positive myotubes) was significantly reduced in the dKO MDSPCs relative to the MDSPCs isolated from the WT mice (*P<0.001).

These results demonstrated that a muscle disease associated with a defective muscle regeneration process also leads to a defect in MDSPCs similar to that observed with the aged/progeroid MDSPCs. Furthermore, these results suggest that muscle damage indeed can contribute to MDSPCs dysfunction through a non cell autonomous mechanism.

Tissue-Specific Knockout of ERCC1-XPF in the Mouse Brain Leads to a Reduction in Neuronal Progenitors.

Mice with deletion of ERCC1 specifically in neurons in the brain have been generated. Sections from the brain of these mice showed a loss of cells in the subgranular zone of the dentate gyrus, usually comprised of neuronal progenitors capable of neurogenesis in adult mice. These results suggest that the loss of ERCC1 in neurons has an adverse effect on neuronal progenitor cells, providing further support to the proposed experiments to examine the effect of targeted aging of the microenvironment or distant tissues on MDSPC number and function.

Functional MDSPCs Ameliorate Pathology Associated with Accelerated Aging by Reducing Endogenous NF-κB Activation, ROS and Oxidative DNA Damage Through Paracrine/Endocrine Mechanisms.

IP delivery of young WT MDSPCs into $Ercc1^{-/-}$ and $Ercc1^{-/\Delta}$ mice leads to a significant extension of lifespan and healthspan. Injection of WT MDSPCs increases neovascularization in different tissues. Since oxidative DNA damage increases with both natural and accelerated aging in multiple tissues, the ability of systemic treatment with young, not aged, MDSPCs to reduce oxidative DNA damage and ROS following injection into aged and $Ercc1^{-/\Delta}$ mice are examined. Similarly, the ability of the injected young MDSPCs to reduce cellular senescence as well as rejuvenate endogenous aged/progeroid MDSPCs will be determined.

$10^6$ young MDSPCs are injected into either Ercc1-/-; NF-κBeGFP mice at day 14, Ercc1-/Δ NF-κB-eGFP mice at week 5 or naturally aged, 30 month old NF-κBeGFP reporter mice. As a control, a similar number of Ercc1-/- MDSPCs or PBS is used. The treated mice are sacrificed at 2 and 4 weeks post injection and analyzed for the extent of oxidative DNA damage, NF-κB activation, ROS levels and cellular senescence. If necessary, mouse models carrying either the p16INK4-Luciferase or p16INK4-Tomato can be used to assess effects on senescence in vivo.

For analysis of angiogenesis, a Tie2eGFP reporter mouse is used along with analysis of blood vessels by staining with a CD31 antibody. The extent of engraftment of the MDSPCs in different tissues is analyzed by transducing the MDSPCs prior to injection with a retroviral vector expressing a nuclear localizing LacZ gene. Finally, whether the injection of young MDSPCs can rejuvenate endogenous aged/progeroid MDSPCs, as suggested by transwell experiments, will be examined.

The injection of $Ercc1^{-/-}$ mice with $10^6$ young MDSPCs results in a pronounced weight gain (greater than 50% of initial weight) and more than a doubling of their normal life expectancy compared to PBS and fibroblast treated $Ercc1^{-/-}$ mice. In addition, some of the typical symptoms of accelerated aging such as kyphosis, dystonia, muscle wasting, growth retardation, cachexia and loss of vision were greatly attenuated in the MDSPC IP injected $Ercc1^{-/-}$ mice. IP injection of WT MDSPCs into 6-7 week old $Ercc1^{-/\Delta}$ mice also showed the trend of extending lifespan in 80% of the MDSPC-injected mice in comparison to PBS-injected littermates (28 versus 22 weeks respectively). More importantly, MDSPC transplantation delayed the onset of the majority of the age-related pathologies in these mice (n=5 pairs, P=0.0006).

Transplantation of WT MDSPCs (IM and IP) Induces Angiogenesis in Skeletal Muscle.

Given that only a very few donor, LacZ positive MDSPCs were detected in host tissues, the anti-aging effects of the young WT MDSPCs is potentially mediated through a paracrine or endocrine mechanism. Since the beneficial effect of MDSPCs in various tissues, like skeletal muscle, heart and bone, is related, at least in part, through neoangiogenesis, it was investigated whether the degree of angiogenesis in the skeletal muscle of these injected progeroid mice was increased. Vascularity of the host muscle tissue was analyzed by co-staining dystrophin to highlight muscle fibers and CD31 to identify capillary endothelial cells. Muscles of 15 day-old Ercc1-/- mice (non-injected) had significantly reduced numbers of CD31+ cells at the periphery of muscle fibers compared to their WT littermates (0.56 CD31+ cells/fiber vs. 1.25 for WT mice, *P<0.001, Students t-test). IM administration of young WT MDSPCs into $Ercc1^{-/-}$ mice ($Ercc1^{-/-}$ 17d IM) led to a significant increase in the number of CD31+ cells (1.06 CD31+ vessels/fiber; § P<0.05, Tukey's test) compared to the non-injected $Ercc1^{-/-}$ mice (0.56 CD31+ vessels/fiber). Notably, the IP injection of young WT MDSPCs into $Ercc1^{-/-}$ mice ($Ercc1^{-/-}$ 9 wks IP) also led to a significant increase in the number of CD31+ cells 9 weeks post-injection compared to the untreated $Ercc1^{-/-}$ mice that only live 3-4 wks (1.05 CD31+ vessels/fiber; § P<0.05, Tukey's test).

Microvasculature in the Brain of ERCC1-Deficient Mice is Reduced in Comparison to WT Mice but the IP Transplantation of WT MDSPCs Induces Angiogenesis in the Brain.

IP treatment of $Ercc1^{-/-}$ mice with MDSPCs resulted in dramatically improved neovascularization in the cerebral cortex compared to untreated mutant animals. Tissue sections of the cerebral cortex were immunostained for the endothelial marker CD31 to identify microvasculature. Untreated Ercc1-/- mice showed a significantly decreased vascular area (1.2%) in their brains compared to WT littermates (2.5%) at 21 days of age. Progeroid mice IP injected with young WT MDSPCs showed significantly improved neovascularization in the brain at 21 days (2.2%) indistinguishable from age-matched WT mice (*P<0.05, Dunn's test).

Co-culture of WT MDSPCs with Ercc1$^{-/-}$ MDSPCs rescued the proliferation defect of Ercc1$^{-/-}$ MDSPCs.

To examine a possible mechanism behind the beneficial effect of implanted WT MDSPCs on the ERCC-deficient mice, MDSPCs isolated from Ercc1$^{-/-}$ deficient mice at 14 days and WT MDSPCs were co-cultured. Using the LCI system, the proliferation behavior of the Ercc1$^{-/-}$ MDSPCs was examined for a period of 70 hrs. Consistent with previous results, the Ercc1$^{-/-}$ MDSPCs, like the Ercc1$^{-/\Delta}$ MDSPCs, showed a slower proliferation rate than WT MDSPCs, indicating a possible defect in the MDSPC compartment in both accelerated aging mouse models in the co-culture assay. In contrast, the Ercc1$^{-/-}$-MDSPCs not only did not undergo senescence, but their proliferation ability increased significantly when co-cultured with WT MDSPCs (P<0.001, Mann-Whitney Rank sum Test). Notably, the ability of the cells to undergo myogenic differentiation was also rescued after co-culturing Ercc1$^{-/-}$ MDSPCs with WT MDSPCs. Ercc1$^{-/-}$ MDSPCs tend to fuse and form spheres (f-MyHC-positive) containing many nuclei (DAPI). In contrast, after co-culturing with WT MDSPCs, normal myotube formation (f-MyHC-positive) was restored, indicated by numerous and large multinucleated myotubes generated by Ercc1$^{-/-}$ MDSPCs. Thus, WT MDSPC co-culture rescued the proliferation and differentiation defects associated with the ERCC1-deficient MDSPC. These results support the hypothesis that WT MDSPCs increase Ercc1$^{-/-}$ MDSPC proliferation and inhibited senescence potentially through a secretory paracrine effect. These results may also explain the underlying mechanism for delaying the age-related pathologies and extension of the life span of the ERCC1-deficient mice after WT MDSPCs transplantation.

Conditioned Media from Young WT MDSPCs Restored the Function of Aged MDSPCs.

The results of recent studies have shown that culturing Ercc1$^{-/-}$ MDSPCs with WT MDSPCs culture conditioned medium can also rescue, at least in part, the differentiation defects observed in the Ercc1$^{-/-}$ MDSPCs, suggesting the paracrine effect that the Ercc1$^{-/-}$ MDSPCs impart on the Ercc$^{1-/-}$ MDSPCs. (See Lavasani et al. *Nature Comm'n.*, 3:608, DOI: 10.1038/ncomms 1611 (2012) (incorporated by reference all references cited, herein)). After culturing the Ercc1$^{-/-}$ MDSPCs with WT MDSPCs conditioned medium the ability of the cells to undergo myogenic differentiation was improved. Likewise, impaired differentiation of old WT MDSPCs was also rescued by conditioned media from young WT MDSPCs. These results support the hypothesis that the WT MDSPCs could increase proliferation and inhibit the senescence of the progeroid (Ercc1$^{-/-}$) and old WT MDSPCs, probably through the release of secreted or released factors. These results may also explain the underlying mechanism(s) that the WT MDSPCs impart to improve the histopathology of the Ercc1–/– mice after being implanted IP.

The factors secreted specifically by functional stem cells able to improve age-dependent tissue homeostasis and neoangiogenesis can be identified by unbiased proteomic approaches. Young, but not aged, MDSPCs can extend lifespan and healthspan through a paracrine/endocrine mechanism. Factors secreted by functional MDSPCs can rescue dysfunctional MDSPCs.

Modern protein mass spectrometry methods are used to measure and identify factors secreted by functional, but not dysfunctional MDSPC. Differential Mass Spectrometry (dMS) is an efficient MS-based strategy for comparing complex biological samples, including plasma and cellular extract. This un-biased analysis of all ions detected by high resolution Fourier transform mass spectrometry is a powerful approach for discovering biologically relevant peptides and proteins. This technique has been used successfully to identify candidate plasma and cerebral spinal fluid markers that track with disease progression and/or respond to treatment with specific classes of drugs. An important advantage of the dMS approach is that it is not limited to the analysis of tryptic peptides and has been successfully applied to the identification of intact plasma peptides and proteins. To enable the detection of molecules present at low abundance, a variety of classical biochemical sample preparation methods (e.g. ultrafiltration, strong cation exchange chromatography, immuno-depletion, etc.) is used to fractionate the conditioned media with function assessed by their ability to rescue dysfunctional MDSPCs. The factors identified as secreted by young MDSPCs are validated using either lentiviral gene transfer of shRNA, to reduce expression, or cDNAs, to increase expression, and the effects on and MDSPCs determined. In particular, the ability of the conditioned media from the genetically modified MDSPCs to rescue dysfunctional MDSPCs is examined. Similarly, the ability of genetically modified MDSPCs to extend healthspan and lifespan of ERCC1-deficient mice following IP administration is also determined.

MDSPCs are isolated using the established preplate technique from the gastrocnemius muscle from Ercc1$^{-/\Delta}$, Ercc1$^{-/-}$, and age-matched WT mice at different time points.

Cell proliferation (cell numbers at increasing time points) and the cell population doubling time (number of hours required for the cell number to double) is collected and quantitated using the LCI system following a previously published methodology.

Cell differentiation is assessed by switching the proliferation medium into fusion medium (DMEM containing 2% horse serum and 1% penicillin/streptomycin) for 3-4 days. Cells are then immunostained for fast myosin heavy chain (f-MyHC) and the degree of myogenic differentiation (the percent f-MyHC expressing cells per total nuclei) is measured as previously described. For adipogenic, osteogenic, and chondrogenic differentiation, MDSPCs are seeded onto 6-well plates and lineage-specific differentiation media (Lonza) added for 7 days.

Young WT MDSPCs are cultured for 2 days in 25 cm$^2$ collagen coated flasks and then treated with differentiation media (DMEM medium supplemented with 2% FBS) for 3 days. The supernatant is collected and used as conditioned media. MDSPCs from 21 day-old Ercc1$^{-/-}$ mice and 2 yr old WT mice are grown in the presence of this conditioned media or unconditioned differentiation media to determine its impact on myogenic differentiation.

All statistical tests will use a nominal type I error rate of p<0.05 and use two-tailed tests where applicable. A paired Student's t-test is used when two groups of data are being compared. One-way ANOVA is performed between test and control groups when multiple groups are being compared.

Genetically Engineered Stem/Progenitor Cells

In another aspect of the present invention, the stem/progenitor cells (e.g., MDSPCs) of this invention may be genetically engineered to contain a nucleic acid sequence(s) encoding one or more active biomolecules, and to express these biomolecules, including proteins, polypeptides, peptides, hormones, metabolites, drugs, enzymes, and the like. Such stem/progenitor cells may be histocompatible (autologous) or nonhistocompatible (allogeneic) to the recipient, including humans. These cells can serve as long-term local delivery systems for a variety of treatments, for example, for the treatment of such diseases and pathologies as cancer, transplant rejection, and the regeneration of muscle and nerve tissues, diabetes, liver failure, renal failure, neural defects and diseases such as Parkinson's disease, and to deliver a gene product to a site of tissue augmentation, or void filling, such as a therapeutic agent, as described herein.

Preferred for use in the present invention are autologous stem/progenitor cells, which will not be recognized as foreign to the recipient. In this regard, the stem/progenitor cells used for cell-mediated gene transfer or delivery will desirably be matched vis-a-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722.

The stem/progenitor cells may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. Stem/progenitor cells can be transfected or transduced by different vectors and thus can serve as gene delivery vehicles to transfer the expressed products into surrounding tissues.

Although viral vectors are preferred, those having skill in the art will appreciate that the genetic engineering of cells to contain nucleic acid sequences encoding desired proteins or polypeptides, cytokines, and the like, may be carried out by any methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

Vectors for introducing heterologous (i.e., foreign) nucleic acid (DNA or RNA) into stem/progenitor cells for the expression of bioactive products are well known in the art. Such vectors possess a promoter sequence, preferably, a promoter that is cell-specific and placed upstream of the sequence to be expressed. The vectors may also contain, optionally, one or more expressible marker genes for expression as an indication of successful transfection and expression of the nucleic acid sequences contained in the vector.

Illustrative examples of vehicles or vector constructs for transfection or infection of stem/progenitor cells of the present invention include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. Examples of such functional sequences include polynucleotide, e.g., DNA or RNA, sequences comprising transcriptional and translational initiation and termination regulatory sequences, including promoters (e.g., strong promoters, inducible promoters, and the like) and enhancers which are active in cells.

Also included as part of the functional sequences is an open reading frame (polynucleotide sequence) encoding a protein of interest; flanking sequences may also be included for site-directed integration. In some situations, the 5'-flanking sequence will allow homologous recombination, thus changing the nature of the transcriptional initiation region, so as to provide for inducible or non-inducible transcription to increase or decrease the level of transcription, as an example.

In general, the nucleic acid sequence desired to be expressed by the stem/progenitor cell is that of a structural gene, or a functional fragment, segment or portion of the gene, that is heterologous to the stem/progenitor cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, cell differentiation factors, cell signaling factors and programmed cell death factors. Specific examples include, but are not limited to, genes encoding BMP-2 (rhBMP-2), IL-1Ra, Factor IX, and connexin 43.

As mentioned above, a marker may be present for selection of cells containing the vector construct. The marker may be an inducible or non-inducible gene and will generally allow for positive selection under induction, or without induction, respectively. Examples of commonly-used marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the stem/progenitor cells. Such replication systems are represented by replication-defective adenovirus constructed as described, for example, by G. Acsadi et al., 1994, Hum. Mol. Genet 3:579 584, and by Epstein-Barr virus. Examples of replication defective vectors, particularly, retroviral vectors that are replication defective, are BAG, described by Price et al., 1987, Proc. Natl. Acad. Sci. USA, 84:156; and Sanes et al., 1986, EMBO J., 5:3133. It is understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to in vivo injection of the cells. In this regard, the vectors may be introduced into retroviral producer cells for amphotrophic packaging. The natural expansion of stem/progenitor cells into adjacent regions obviates a large number of injections into or at the site(s) of interest.

In another aspect, the present invention provides ex vivo gene delivery to cells and tissues of a recipient mammalian host, including humans, through the use of stem/progenitor cells, e.g., MDSPCs or early progenitor muscle cells, which have been virally transduced using an adenoviral vector engineered to contain a heterologous gene encoding a desired gene product. Such an ex vivo approach provides the advantage of efficient viral gene transfer, which is superior to direct gene transfer approaches. The ex vivo procedure involves the use of stem/progenitor cells from isolated cells of muscle tissue. For example, a muscle biopsy that will serve as the source of MDSPCs can be obtained from an injury site or from another area that may be more easily obtainable from the clinical surgeon.

It is appreciated that in accordance with one embodiment of the present invention, clonal isolates can be derived from the population of muscle-derived progenitor cells (i.e., PP6 cells) using various procedures known in the art, for example, limiting dilution plating in tissue culture medium. Clonal isolates comprise genetically identical cells that originate from a single, solitary cell. In addition, clonal isolates can be derived using FACS analysis as described above, followed by limiting dilution to achieve a single cell per well to establish a clonally isolated cell line. An example of a clonal isolate derived from the PP6 cell population is mc13, which is described in Example 9. Preferably, MDSPCs clonal isolates are utilized in the present methods, as well as for genetic engineering for the expression of one or more bioactive molecules, or in gene replacement therapies.

The MDSPCs are first infected with engineered viral vectors containing at least one heterologous gene encoding a desired gene product, suspended in a physiologically acceptable carrier or excipient, such as saline or phosphate buffered saline, and then administered to an appropriate site in the host. Consistent with the present invention, the MDSPCs can be administered to body tissues, including bone, epithelial tissue, connective tissue, muscle tissue, and various organ tissues such as those organs that are associated with the digestive system, cardiovascular system, respiratory system, reproductive system, urological system, and nervous system, as described above. The desired gene product is expressed by the injected cells, which, thus, introduce the gene product into the host. The introduced and expressed gene products can thereby be utilized to treat, repair, or ameliorate the injury, dysfunction, or disease, due to their being expressed over long time periods by the MDSPCs of the invention, having long-term survival in the host.

In animal model studies of myoblast-mediated gene therapy, implantation of $10^6$ myoblasts per 100 mg muscle was required for partial correction of muscle enzyme defects (see J. E. Morgan et al., 1988, J. Neural. Sci. 86:137; T. A. Partridge et al., 1989, Nature 337:176). Extrapolating from this data, approximately $10^{12}$ MDSPCs suspended in a physiologically compatible medium can be implanted into muscle tissue for gene therapy for a 70 kg human. This number of MDSPCs of the invention can be produced from a single 100 mg skeletal muscle biopsy from a human source. For the treatment of a specific injury site, an injection of genetically engineered MDSPCs into a given tissue or site of injury comprises a therapeutically effective amount of cells in solution or suspension, preferably, about $10^5$ to $10^6$ cells per cm$^3$ of tissue to be treated, in a physiologically acceptable medium.

Screening Methods

The invention also provides methods of screening for one or more candidate compounds that modulate expression of one or more secreted or released regulatory factors, or factors that regulate the expression of such secreted or released regulatory factors from a population of isolated mammalian stem/progenitor cells (e.g., adult stem/progenitor cells). In such methods, the population of stem/progenitor cells is exposed to one or more candidate compounds and the expression of one or more regulatory factors, or factors that regulate expression of regulatory factors is determined in a population of stem/progenitor stem cells that are not exposed to the candidate compound. Then, the expression of the one or more secreted or released regulatory factors, or factors that may regulate expression of such regulatory factors in the exposed population of stem/progenitor cells is compared with the control population, thereby identifying one or more candidate compounds that modulate (i.e., increase or decrease) expression of one or more secreted or released regulatory factors, or factors that regulate expression of such factors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention are apparent from the following detailed description and claims.

For the purposes of promoting an understanding of the embodiments described herein, reference is made to preferred embodiments and specific language are used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

Body mass index (BMI) is a measure of body fat based on height and weight that applies to both men and women. BMI is considered in to fall into the so called "normal" range when BMI is between about 18.5-24.9. According to this invention, an underweight subject has a BMI <18.5; an overweight subject in the range about 25-29.9 and an obese subject has a BMI of about 30-39.9, and BMI of 40 or greater is considered extremely obese.

The term "isolated" as used herein with respect to nucleic acids, such as DNA or RNA, refers to molecules separated from other DNAs, or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of RNA or DNA made from nucleotide analogs (e.g., peptide nucleic acids) and as applicable to the embodiment being described, single (sense or antisense) and double-stranded polynucleotides.

The following examples are illustrative, but not limiting, of the methods and compositions of the present invention. Other suitable modifications and adaptations of the variety of conditions and parameters normally encountered in therapy and that are obvious to those skilled in the art are within the spirit and scope of the embodiments.

EXAMPLES

Example 1

"Modified Pre-Plate Method," to Isolate Stem/Progenitor Cells from Skeletal Muscle Reagents: a) Hank's Buffered Salt Solution plus Calcium Chloride and Magnesium Chloride (HBSS; INVITROGEN™, Cat. #24020-117); b) Collagenase type XI (SIGMA-ALDRICH®, Cat. #C7657); c). Dispase (INVITROGEN™, Cat. #17105-041); d) Trypsin-EDTA (INVITROGEN™, Cat. #15400-054); e) Dulbecco's Modified Eagle Medium (DMEM, high glucose; INVITROGEN™, Cat. #11995-073); f) Fetal Bovine Serum (FBS; INVITROGEN™, Cat. #10437-028); g) Horse Serum (HS; INVITROGEN™, Cat. #26050-088); h) Chick Embryo Extract (CEE; Accurate Chemical Co. Cat. # CE650T-10); h) Penicillin/Streptomycin (P/S, INVITROGEN™, Cat. #15140-122); i) Collagen, type I (SIGMA-ALDRICH®, Cat. #C9791); and j) Dimethyl sulfoxide (DMSO, SIGMA®, Cat. #D-2650).

Laboratory supplies: a) Tubes: 15 mL and 50 mL polypropylene (e.g. BD, Cat. #352097 and #352098); b) Filters: disposable sterile 0.22 m pore size and 500 mL sterile filter system (e.g. CORNING®, Cat. #430769); c) Petri dishes: 35 mm and 65 mm (e.g. BD, Cat. #351008); d) Cell strainer: disposable 70 m pore size (e.g. BD, Cat. #352350); e) Flasks: 25 cm$^2$ (T-25) and 75 cm$^2$ (T-75) (e.g. BD, Cat. #353109 and #353136); f) Cryovials (1.5 mL, e.g. NALGENE®, Cat. #5000-1020); and g) "MR. FROSTY®" freezing container (NALGENE®, Cat. #5100-0001) or empty 15 mL STYROFOAM™ boxes.

Required equipment: a) Sterile surgical equipments (e.g. forceps, scissors); b) Laminar flow tissue culture hood (e.g. The Baker Company, Model #SG 403): c) Incubator to maintain 37° C., >95% humidity and an atmosphere of 5% $CO_2$ (e.g. HERACELL 150®, THERMO FISHER™, Cat. #51022393); d) Refrigerated bench-top centrifuge (e.g. LEGEND™ RT, THERMO FISHER™, Cat. #75004377); e) Laboratory balance (e.g. Mettler Toledo, Model #PM4000); f) Pipet-aid (e.g. Drummond Scientific, Cat. #4-000-101); g) Adjustable micropipettes: 10 μL, 200 μL and 1000 μL (e.g. GILSON®, Model #P200N) with sterile disposable plastic pipette tips (e.g. Denville Scientific, Cat. #P1326-CPS; h) Hemocytometer (e.g. Hausser 1475) or automatic cell counter (e.g. INVITROGEN™, Cat. #C10281); and i) Inverted light microscope with phase contrast capabilities and objectives of 5×, 10×, 20× magnification (e.g. NIKON®, Model #TMS 215798).

Methods Solution preparation: Tissue digestion solution: The working concentrations are 0.2% (wt/vol) collagenase Type-XI, 2.4 U/mL dispase, and 0.1% (wt/vol) Trypsin-EDTA. Both solutions are prepared in HBSS and filtered using a 0.22-μm sterile filter, aliquoted into 10 mL volume aliquots, and stored at −20° C. Solutions should be pre-warmed to 37° C. before use. Proliferation Medium (PM): Except for DMEM, all components of the PM should be pre-prepared and stored at −20° C. Pre-warm all the components to 37° C. before use. To prepare 500 mL of PM, combine 392.5 mL DMEM, 50 mL FBS (10%), 50 mL HS (10%), and 5 mL P/S (1%) in a 500 sterile filter attached to the filter receiver. Add 2.5 mL CEE (0.5%) as the last 10 mL of solution is drawn through the sterile filter system, as it clogs the filter and retards the process. PM should be prepared fresh for each new culture of MDSPCs. Unused PM can be stored at 4° C. PM for a maximum of 4 weeks. Freezing medium: 1:10 dilution of DMSO: FBS or PM.

Collagen coating solution: Day 1: Under a laminar flow hood using sterile technique, add 0.1 g of collagen type I to a sterile 1-liter glass bottle with screw cap. In a sterile graduated cylinder, add 5.7 mL glacial acetic acid to 1 liter of double-distilled water. Add the mixture to the collagen by filtering the acid/water through a 500 mL bottle top sterilization filter. Stir with a magnetic stir bar overnight. Day 2: Under a laminar flow hood using sterile technique, pour collagen type I into 50 ml sterile polystyrene centrifuge bottles and spin at 2,630×g for 20 min at 4° C. Transfer the supernatant to sterile (autoclaved) bottles while. Under a laminar flow hood, slowly add 50 mL of chloroform (caution: volatile) per 500 mL solution using a sterile glass funnel. The chloroform will form a layer under the collagen solution. Do not shake or stir. Allow to sit overnight (can be extended to two days) at 2-8° C. Day 3: Under a laminar flow hood using sterile technique, transfer the top aqueous layer (containing the collagen) to a new sterile 1-liter bottle and store at 2-8° C. Discard the bottom layer containing the chloroform according to your institution's hazardous waste guidelines.

Collagen coating flasks and plates: To coat the flasks or plates with Collagen Type-I, warm the solution in 37° C. water bath. Add the recommended volume of collagen to the flasks/plates. Make sure the solution is evenly distributed by gently rocking them until the surface is covered. Repeat frequently over the next 2 hrs. Keep the flasks/plates open in culture hood with blower on for a minimum of 3-4 hrs, but ideally for 7 hrs. After this, pipette off the excess collagen solution to a flask label as "used collagen type-I". This can be reused for future coating. Leave the flasks/plates partially open in a running laminar flow hood overnight to promote drying. Keep the flasks/plates in a laminar flow hood with the germicidal UV lamp on for 2 hrs. The next day, cap the flasks/plates, label, bag in the original wrapping and store at room temperature.

Isolating and digesting skeletal muscle from mice: (1) Sterilize surgical tools; (2) Euthanize the animal by $CO_2$ asphyxiation; (3) Dissect out the skeletal muscle. For adult mice, use the hind limb muscles including gastrocnemius, soleus and quadriceps muscle (350-450 mg). For young mice (1-7 days), the entire limb muscles should be used. Place the tissue from a single animal into a 15 mL tube containing sufficient HBSS to cover the tissue and store on ice; (4) Transfer one skeletal muscle at a time to a sterile 65 mm Petri dish and wash it three times with sterile HBSS to remove any debris that may have adhered to the tissue during the dissection; (5) Using forceps and scissors, dissect the muscle from other tissues including the bone, tendon, nerve, major blood vessels, fat, and connective tissue in a sterile 35 mm Petri dish; (6) Add 10 mL of sterile HBSS to a fresh Petri dish and begin the mechanical digestion of the trimmed muscle by mincing it into a coarse slurry using very sharp spring scissors; (7) Transfer the minced tissue slurry into a 15 mL conical tube using a 10 ml transfer pipette and centrifuge at 930×g at 2-8° C. for 5 min; (8) Aspirate off the supernatant, resuspend the pellet with HBSS, and centrifuge again as described in step 4; (9) Aspirate off the supernatant and weigh the pellet (slurry) using a precise scale. Zero the scale using an empty 15 mL conical tube; (10) Begin the enzymatic digestion by adding 10 ml of pre-warmed 0.2% collagenase type XI digestion solution (approximately 1 mL per 0.1 g muscle pellet) in a 15 mL tube. Incubate at 37° C. Gently rock the tube by hand every 15 min. After 1 hr, centrifuge at 2,630×g for 5 min; (11) Aspirate off the supernatant and resuspend the pellet/slurry in 10 mL pre-warmed dispase (2.4 units/mL); (12) Incubate at 37° C. for 45 minutes. Gently rock the tube by hand every 15 min. Centrifuge at 2,630×g for 5 min; (13) Aspirate off the supernatant and resuspend the viscous slurry in 0.1% Trypsin-EDTA solution diluted in HBSS. Incubate at 37° C. for 30 min. Gently rock the tube by hand every 15 min. Centrifuge at 2,630×g for 5 min; (14) Aspirate out the supernatant and resuspend the cell pellet in 10 mL of PM; (15) Pipette the re-suspended pellet through a 70 m cell strainer placed on top of a 50 mL sterile conical tube. Rinse the strainer with PM to collect all of the cells.

Example 2

Figure 2:
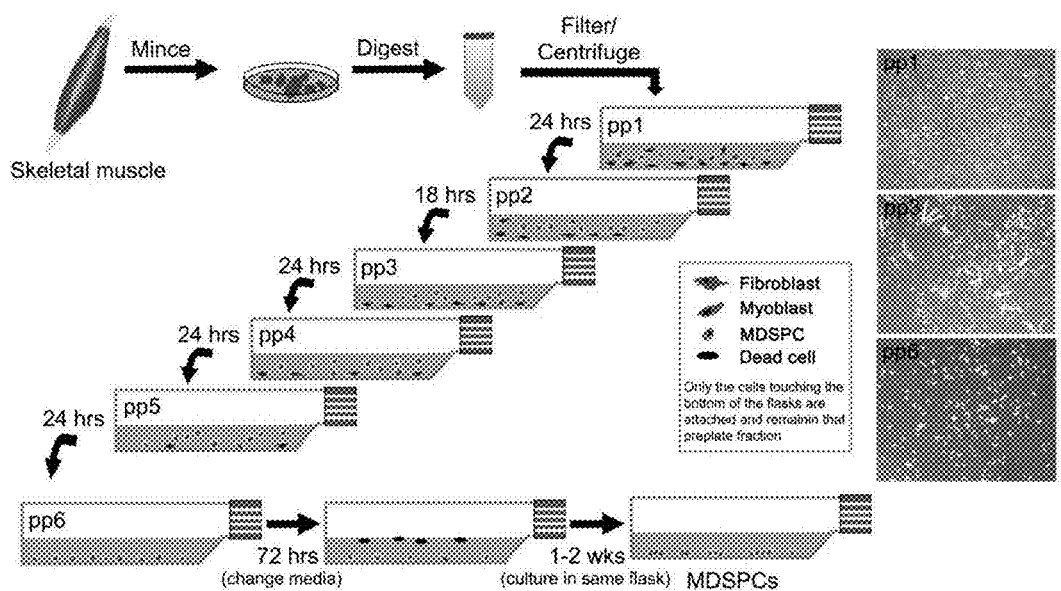
FIG. 2 depicts the isolation of muscle-derived stem/progenitor cells (MDSPCs). Skeletal muscle is mechanically and enzymatically dissociated to a single cell suspension. The muscle cells are resuspended in proliferation medium and plated on collagen type I-coated flasks. Different populations of muscle-derived cells are isolated based on their adhesion characteristics. Pre-plate 1 (pp1) cells adhere in the first 2 hrs after isolation and consist predominantly of primary fibroblasts. Subsequent pre-plates obtained at 18-24 hrs intervals (pp2-5), contain a mixture of fibroblast and myoblast-like cells. Cells in pp6 take an additional 72 hrs to attach. Most of the cells from pp6 die during the first 1-2 wks of culturing. The few adherent cells that survive proliferate to form colonies. These viable, proliferating pp6 cells are MDSPCs.

Pre-Plating Steps (See FIG. 2):

Plate the cells from one animal/tube on one collagen type I-coated T-25 flask and incubate at 37° C. in a humidified, 5% $CO_2$ incubator for 2 hrs.

Two hours after plating, early adhering cells (mainly fibroblasts) will attach to the surface of the flask; label this cell population as pre-plate 1 (pp1).

Transfer the media containing the non-adherent cells into a second collagen type I-coated T-25 flask, label pp2. Return flasks to the incubator.

After 18 hrs, transfer the media from pp2 into a sterile 15 mL conical tube and centrifuge at 930×g at 4° C. for 5 min. Aspirate out the supernatant and resuspend the cell pellet in 5 mL of PM and transfer the media containing the nonadherent cells into a third T-25 flask labeled pp3. Add 5 mL fresh PM to the pp2 flask. Return the flasks to the incubator.

Repeat Step 4 three times to obtain pp6. This last cell suspension can be maintained for up to 72 hrs to maximize adherence of the slowest adhering cells. Change the media on pp2-5 cells every other day and freeze as soon as a sufficient number is reached. Most of the cells in pp6 die, but the surviving cells will slowly begin to proliferate, creating small adherent colonies. These viable cells are small, round and refractive. The surviving cells at pp6 are termed muscle derived stem/progenitor cells (MDSPCs).

Expanding MDSPCs (See FIGS. 12A-12D):

Remove the culture medium (PM) and wash the cells with HBSS. Apply pre-warmed 0.25% Trypsin-EDTA in HBSS and gently tap the corners or bottom of the flasks stimulate cell detaching. After ~1 min, check the flask under the microscope to ensure that all of the cells are detached. Inhibit the Trypsin-EDTA by adding PM (~3 mL for T-25 flasks). Transfer the cell suspension to a 15 mL tube and centrifuge at 930×g for 5 min at 4° C.

Aspirate off the supernatant and resuspend the pellet in PM. Count the cells and plate at a density of 500-1000 cells/$cm^2$ (e.g. ~12,000-25,000 cell in T-25 flask) in a fresh collagen type I-coated flask. Incubate the cells at 37° C. in a humidified, 5% $CO_2$ incubator. Maintain the cells at a low cell density (30% confluence), to minimize cell myogenic differentiation. MDSPCs need to be trypsinized when small colonies are visible regardless of the overall cell density. MDSPCs usually remain quiescent after isolation; therefore, 3-4 weeks are needed to obtain sufficient cells for cryopreservation or experimentation.

Re-Plating MDSPCs (See FIG. 2):

If pp6 cells contain a high percentage of large, flat, fibroblast-like cells, it is necessary to re-plate the cells as described below. Aspirate out the supernatant and resuspend the pellet in PM, then plate the cells in a fresh collagen type I-coated T-25 flask. Allow the cells to adhere to the flask for 20-30 min in the incubator. Collect the media containing the non-adherent cells and "re-plate" them onto a new collagen type I-coated T-25 flask. Incubate the cells at 37° C. in a humidified, 5% $CO_2$ incubator. Re-plating steps can be repeated several times if necessary.

Freezing MDSPCs:

Freeze each preplate population (pp1-pp5) when the cells are 80% confluency. The pp6 can be frozen once a sufficient number of cells has been reached, while keeping the cells at low confluence (<30%) at all times. Cell pellets containing ~$1 \times 10^5$-$3 \times 10^5$ cells should be mixed with freezing media (1:10 dilution of DMSO: FBS) and placed in −20° C. for 2 hrs. The vials are then placed in the middle of two 15 mL STYROFOAM™ boxes or a MR. FROSTY® freezing container then transferred to a −80° C. freezer. For long term preservation, the cells should be transferred to liquid nitrogen after 3 months.

Thawing MDSPCs:

Transfer frozen vials of cells from the −80° C. freezer or liquid nitrogen to the laboratory on dry ice. Thaw the content of the vials using a 37° C. water bath. Thawing needs to be done quickly (<1 min) because DMSO is toxic to the cells. Transfer the content of the vial into a 15 mL conical tube containing 5 mL of PM and centrifuge at 930×g for 5 min at 4° C. Aspirate off the supernatant. Resuspend the cell pellet in a small volume of PM media. The contents of one cryovial (~$1 \times 10^5$/T-75) should be plated. The day after thawing, change the media to remove the dead cells.

Measuring the Quality/Function of Isolated MDSPCs (See Table 2):

After isolation, the quality of MDSPC is assessed by measuring stem-like properties including expression of stem/progenitor markers profile, self-renewal, and multi-lineage differentiation (summarized in Table 2). Using HBSS with $Ca^{2+}$ and $Mg^{2+}$ reduces the enzymatic activity of trypsin. But it is effective for gently releasing stem/progenitor cells from plates. Based on experience, CEE is critical for the isolation and maintenance of MDSPCs. CEE from different manufactures and even different lots produced by the same manufacturer has a profound effect on the quality of MDSPCs, including their capacity for proliferation and differentiation. The best results are obtained if the CEE is not pre-cleared by centrifugation or ultrafiltration.

The division time of individual MDSPCs were measured while growing in the cell population or as isolated clones. To confirm that the population doubling time (PDT) accurately represented the proliferation rate of MDSPCs and was not simply the average of the heterogeneous population, we measured the cellular division time (DT) of individual cells. The DT of single cells in the population and single clones isolated from the population (n=3-7 per genotype) were compared. Individual cells from preplate 6 were seeded in 96-well plates using FACSARIA® cytometer. Five days after plating, the DT of individual cells in each well was monitored for 72 hrs using the Live Cell Imaging. Using the images acquired, the time between the cytokinesis events was calculated. Reported is the average±s.d. for each genotype. There was no significant difference between the population and clonal DT.

plate (1 mL/well), 12-well plate (0.5 mL/well). 24-well plate (0.25 mL/well, 96-well plate (50 µL/well). For newborn animals, both the hindlimb and forelimb muscles were collected. Collagenase type XI and dispase digestion can be extended when a larger amount of muscle must to be digested. But the cells are sensitive to prolonged exposure to Trypsin-EDTA. If contamination is observed, discard all

TABLE 2

|  | Assay used | Unit | Young murine WT-MDSPCs | Aged murine MDSPCs |
|---|---|---|---|---|
| Marker profile Sca1+ CD34+ CD45− | Immuno; RT-PCR | % cells of total population | 18% of cells at pp3 (host 3 wks old); 9% at pp3 (host 4-5 mths old) | 3% of cells at pp3 (host 3 yrs old) |
| Proliferation | Live-cell imaging (LCI) system | DT (hrs) PDT (hrs) | DT = 13 ± 2 hrs PDT = 15 hrs (host 3 wks old) | DT = 16 ± 6 hrs PDT = 18 hrs (host 2 yrs old) |
| Differentiation | myogenic osteogenic chondrogenic adipogenic | +/− differentiation capacity | + for all four lineages | adipocyte > myocytes > chondrocyte > osteocyte |
| Engraftment potential and regeneration | IM injection into mdx/SCID mice or WT mice after cardiotoxin injury | # or % of regenerating myofibers and their cross-sectional area | 70% of regenerating, centronucleated fibers have an area >1,000 µm$^2$ | 70% of regenerating, centronucleated fibers have an area <750 µm$^2$ |

DT: division time;
FACS: Flow cytometry;
IM: intramuscular injection;
Immuno: immunocytochemisty;
LCI: live cell imaging;
PDT: population-doubling time;
f-MyHC: fast myosin heavy chain;
WT: wild-type.

MDSPCs were double positive for Sca1 and CD34 and negative for CD45. Although, variability and alteration in the expression levels had been observed as a consequence of in vitro culturing. Growth kinetics (proliferation and/or self-renewal) was measured using a live-cell imaging (LCI) system. This system allowed for time-lapsed imaging of single cells or colonies over long periods of time, so that growth and differentiation kinetics could be accurately measured. To evaluate the differentiation potential of MDSPCs, the cells were switched to specific differentiation media for myogenic, osteogenic, chondrogenic, and adipogenic lineages. Subsequently the cultures were analyzed for lineage-specific morphology and differentiation markers. The function (regenerative capacity) of MDSPCs was evaluated in vivo by injecting the cells into the gastrocnemius muscle of mdx/SCID mice, a mouse model of Duchenne muscular dystrophy with profound muscle degeneration due to lack of dystrophin expression that are also immunocompromised (SCID). Two weeks after injecting MDSPCs, the muscle was harvested and stained for dystrophin to detect donor-derived myofibers. Alternatively, muscle regeneration was tested in wild-type mice following cardiotoxin injury. In this case, regenerating fibers were identified by centronucleation.

Ideally, MDSPCs were stored submerged in liquid nitrogen. This requires special cryovials that can withstand the pressure changes that occur when cells are thawed. It is also important not to overfill the cryovials to prevent the tubes from exploding during the thawing process.

Viability of MDSPCs after thawing was dramatically improved if a 1:10 (v/v) ratio of DMSO:FBS is used rather than DMSO:media.

Amount of collagen type I needed for coating of flasks/plates: T25 (2 ml), T75 (3.5-4 ml), T175 (7.5-8 ml), 6-well cultures and clean the hood and incubators thoroughly with topical application of disinfectant (Coflikt, Decon Laboratories #4101). All removable parts of the hood and incubator were autoclaved before starting a new isolation. It is not recommended to increase the dose of antibiotics or to use antimycotics since this may affect the stemness properties of MDSPCs.

The seeding density is critical and varies depending on the cell proliferation kinetics. Low cell density impedes cell proliferation and high density causes the cells to fuse (differentiate). The optimal density must be determined empirically. Cell proliferation rates vary depending on the sex, age and health of the donor as well as the amount muscle tissue available for cell isolation. Consistency in cell isolation and culturing of MDSPCs is the key to maintaining pluripotency.

Because MDSPCs are quiescent cells, it takes a minimum of 1-2 weeks for cells to show any sign of proliferation. This time varies depending upon the number of cells isolated at pp6. Trypsinization should be avoided until visible colonies are evident.

Cardiotoxin Injection:

For cardiotoxin experiments, 20 µl of 2 µM cardiotoxin (SIGMA-ALDRICH®) dissolved in PBS was injected into the gastrocnemius muscle of mice: 3 old WT (3 yr-old), 5 WT (18 wk-old), and 3 Ercc1$^{-/\Delta}$ (18 wk-old) mice. Two weeks later, the gastrocnemius muscles were harvested, frozen in 2-methylbutane pre-cooled in liquid nitrogen, and cryostat-sectioned (8 µm). Sections were immunostained for dystrophin and fluorescent images were captured using a Nikon Eclipse E800 microscope equipped with a Q imaging Retiga Exi digital camera using Northern Eclipse software (v. 6.0; Empix Imaging, Inc.).

To perform dimensional analysis of dystrophin-positive myofibers, the images were thresholded using this computer software to distinguish the immunofluorescence signal from the back-ground noise signal, and then to determine the number and area of fibers and to provide quantitative measurements of the number of pixels occupied by each individual fiber. The fiber area distribution of >1000 centronucleated individual myofibers per group was measured by determining the total number of pixels occupied by each fiber and converted to square micrometers with the software. Finally, the cross sectional area of, and the distribution of the fiber areas was plotted.

To reveal areas of fibrosis in regenerating muscles, sections were stained with Masson's Trichrome (Kit, K7228; IMEB Inc.), which stains collagen blue, muscle fibers red, and nuclei black. Quantitation of the fibrotic area was done on n=13 images per mouse using the Northern Eclipse software (v. 6.0; Empix Imaging, Inc.).

Transplantation:

To test the myogenic potential of MDSPCs in vivo (see FIG. 3F-3G), $3\times10^5$ WT-MDSPCs (pp6) isolated from two 19 week-old male $Ercc1^{-/\Delta}$ mice and two of their WT littermates were injected into the gastrocnemius muscle of 9 week-old female mdx/SCID mice (n=8 mice, 4 mice/cell population). Mdx is a mouse model of Duchenne Muscular Dystrophy, with profound muscle degeneration due to lack of dystrophin expression. The mice were also immunocompromised (SCID). Two weeks after transplantation, the mice were euthanized and the injected gastrocnemius muscles were isolated and cryopreserved for sectioning. Muscle sections were immunostained with dystrophin to identify regenerated myofibers by donor cells.

To test the ability of MDSPCs to rescue aging phenotypes in progeroid mice after IP administration (see Table 3), $2\text{-}4\times10^5$ MDSPCs per gram body-weight were injected into the peritoneal cavity of 17 day-old $Ercc1^{-/-}$ mice.

healthspan, 6-7 wk-old $Ercc1^{-/\Delta}$ mice were injected IP with about $2\times10^5$ to about $4\times10^5$ MDSPCs per gram body-weight. The injection was repeated 6 wks later. The weight and the age-at-onset of spontaneous progeroid symptoms were assessed bi-weekly by an investigator blinded to the treatment. The age at onset of each symptom was averaged within a treatment group.

Dystonia, a sign of neurodegeneration, is measured as an abnormal response to tail suspension (a clasping rather than splaying reflex). Kyphosis, a sign of osteoporosis, was measured by observing the curvature of the spine compared to wild-type littermates. Ataxia, a sign of cerebellar neurodegeneration, was measured by evaluating the animal's gait and ability to maintain their posture when reared on hind limbs to groom. Priapism and incontinence are only observed in male mice. Lethargy was scored as positive when the mice were slow to rise when startled by moving their cage or attempting to pick them up. Sarcopenia was scored as positive when the mice showed proximal hind-limb wasting. The Aging Score is an overall measurement of the quality of life or healthspan and reflects the fraction of symptoms that occurred later in mice treated with MDSPCs relative to littermate mutant animals that received vehicle only. The aging score was determined as follows. Mice were studied as littermate pairs, where one mutant mouse was treated with the test cells and the other was treated with vehicle only (PBS). For each symptom, the mouse in which the symptom was delayed received a score of +1 and the littermate got a score of 0. If the symptoms occurred simultaneously in both mice, both mice received a score of 0. The sum of the scores for each animal was divided by the number of symptoms measured in that pair of mice (8 for males; 6 for females) to determine the fraction of symptoms delayed. This number was plotted for both animals in each littermate pair then the average for each treatment group was determined to give the aging score. The symptoms evaluated

TABLE 3

| Donor cell line name | Genotype | Age | Cell Sex | Strain | Source of mice | Passage number | # of mice injected | Median lifespan (days) | Average Lifespan (days) | s.e.m. |
|---|---|---|---|---|---|---|---|---|---|---|
| ft* | WT | 3 wks | F | C57BL/6J | Jackson | 20-25 | 6 | 66 | 66 | 2.7 |
| A | WT | 14 d | M | f1 C57BL/6; FVB/n | bred | 15-20 | 4 | 66 | 67 | 2.0 |
| C | $Ercc1^{-/-}$ | 3 wks | F | f1 C57BL/6; FVB/n | bred | 20-22 | 6 | 26 | 37 | 7.2 |
| D | WT | 2 yrs | M | f1 C57BL/6; FVB/n | bred | 20-22 | 6 | 25 | 26 | 1.1 |
| MEF | WT | E13.5 | u | f1 C57BL/6; FVB/n | bred | 5 | 6 | 25 | 38 | 9.6 |
| PBS | n.a. | n.a. | n.a. | n.a. | n.a. | n.a. | 10 | 21 | 36 | 7.5 | n.a.: not applicable,
u: unknown,
MEF: Primary mouse embryonic fibroblast
*This cell line was used to inject $Ercc1^{-/\Delta}$ mice.

Transplantations were performed in a sex-mismatched manner such that the donor cells were of the opposite sex from the host. A littermate mutant animal was injected with vehicle only (PBS). $Ercc1^{-/-}$ mice were allowed to live until "natural" death to determine the effect of MDSPCs on lifespan. In an identical experiment, littermate mutant animals were injected with the same quantity of early passage WT primary mouse embryonic fibroblasts (MEFs) or vehicle only. For the evaluation of the impact of MDSPCs on include kyphosis, dystonia, trembling, ataxia, priapism, urinary incontinence, muscle wasting (sarcopenia), and reduced spontaneous activity (lethargy) due to frailty.

To determine the site of MDSPC cell engraftment after IP administration, $Ercc1^{-/-}$ mice were injected IP at 12 days of age with MDSPCs expressing LacZ and euthanized 8-9 days later (n=4) or injected at 17-19 days of age and tissues harvested at the end of their lifespan (4-9 wks of age; n=4). The reporter MDSPCs were created by transducing them with a retroviral vector containing LacZ with a nuclear localization sequence. Fourteen organs/tissues were isolated from each of the transplanted mice (see Table 4), frozen in 2-methylbutane pre-cooled in liquid nitrogen, cryostat-sectioned (7 µm), and stained with X-gal to identify donor cells as well as hematoxylin and eosin to reveal tissue architecture. To isolate hematopoietic cells from the bone marrow, the femurs of each animal were dissected, muscle removed and the bone marrow was flushed from the long bones using PBS. Red blood cells were removed using Red Blood Cell Lysing Buffer (SIGMA-ALDRICH®). The cell suspension was centrifuged, counted and $2\text{-}3 \times 10^5$ cells in PBS (5 µl) were smeared over Precleaned Superfrost Plus (VWR) slides, air dried overnight, and stained for LacZ expression using X-gal (see the Histology section of Material and Methods). The sections were then stained with CD45 conjugated to FITC (1:300, BD Pahrminogen) for 20 min and evaluated by brightfield and fluorescence microscopy to detect CD45+ hematopoietic cells expressing nLacZ.

TABLE 4

| Organ/Tissue/Cell | Approximate number of sections analyzed per mouse | Number of mice from which tissues were analyzed | Number of mice in which LacZ+ cells were detected |
|---|---|---|---|
| Pancreas | 16 | 8 | 8 |
| Liver | 11 | 8 | 8 |
| Kidney | 27 | 8 | 8 |
| Spleen | 20 | 8 | 8 |
| Lung | 12 | 8 | 1 |
| Heart | 39 | 3 | 0 |
| Thymus | 14 | 8 | 2 |
| Bladder/ureter | 31 | 1 | 1 |
| Brain | 49 | 6 | 0 |
| Skeletal muscle | 25 | 4 | 0 |
| Spinal cord | 79 | 2 | 1 |
| Lymph nodes | 38 | 6 | 0 |
| Esophagus | 18 | 1 | 1 |
| Bone marrow | $3.4 \times 10^7$ cells | 8 | 4 |

For the data in Table 4, the tissues from Ercc1$^{-/-}$ mice administered labeled MDSPCs IP, were analyzed for the presence of LacZ$^+$ donor cells. Listed are the organs/tissues collected, the number of mice analyzed, the average number of sections analyzed per tissue, and the frequency with which donor cells were detected.

To determine if MDSPCs injected IM contribute to host muscle and vasculature, $3 \times 10^5$ LacZ$^+$ donor WT-MDSPCs were transplanted into the gastrocnemius muscles of 12-17 day-old Ercc1$^{-/-}$ mice. Mice were sacrificed 4-5 days post-transplantation, and the gastrocnemius muscles (n=10) were harvested, frozen in 2-methylbutane pre-cooled in liquid nitrogen, and cryostat-sectioned (8 µm). For co-localizing blood vessels and nLacZ, sections were fixed with 4% PFA (paraformaldehyde) stained for rat anti-CD31 (1:300, BD Pharmingen) using Vectastain® Elite ABC kit (Vector Laboratories). Slides were developed using the peroxidase 3,3'-diaminobenzidine (DAB) substrate kit (Vector Laboratories). For brain, endogenous avidin/biotin was inhibited using a Vector Blocking kit (Vector Laboratories). Primary antibody was incubated overnight at 4° C. in 10% rabbit serum containing 0.1% Triton in 1% BSA, and washing buffer used throughout the staining procedure was 0.1% Tween 20 in PBS.

Loss of Stemness Properties with Aging:

In an earlier work the inventors reported isolating these multipotent cells from young [3 week (wk)-old] mice. (See Gharaibeh, B. et al. *Nat. Protoc.* 3, 1501-1509 (2008), Deasy, B. M. et al. *Mol. Ther.* 17, 1788-1798 (2009)). To determine if MDSPCs could also be isolated from adult and old mice, the same preplate technique was followed and the resulting cells were analysed for expression of stem/progenitor cell markers (CD34, Sca-1). Cells isolated from skeletal muscle of young (3 wks), adult (19 wks), and wild-type (WT) [2 years (yrs)] mice via this technique expressed CD34 and Sca-1 (see FIG. 3A), establishing that MDSPCs could be isolated from mice of all ages. Although expression of CD34 appeared mildly attenuated in the older cell populations, Sca-1, which is a more stable marker of MDSPCs, was similarly expressed in all three populations. Furthermore, MDSPCs isolated from adult WT mice showed multilineage differentiation (see FIG. 3B).

To determine if there was a loss of stem cell function associated with aging and progeria, MDSPCs were isolated from old WT mice (2 yrs) as well as progeroid Ercc1$^{-/-}$ (2-3 wks) and Ercc1$^{-/\Delta}$ (5 months) mice and their proliferation and differentiation kinetics were measured in vitro. As controls, MDSPCs were isolated from age-matched WT littermates of the progeroid mice and Xpa$^{-/-}$ (xeroderma pigmentosum complementation group A) mice (3 wks), which are defective in nucleotide excision repair of DNA like ERCC1-deficient mice, but do not age rapidly. To measure proliferation of MDSPCs, an equivalent number of cells from each population were plated and Live-Cell Imaging (LCI) used to measure growth kinetics (see FIG. 3C). Analysis of images captured from the different cell populations revealed that proliferation of MDSPCs isolated from the old WT, Ercc1$^{-/-}$ and Ercc1$^{-/\Delta}$ mice, but not Xpa$^{-/-}$ mice, was significantly reduced relative to MDSPCs isolated from young WT mice (*P<0.05, Tukey's test). The average population doubling time (PDT) was prolonged in MDSPCs isolated from old mice [18 hours (hrs)] and progeroid mice (20-27 hrs) compared to young WT mice (15 hrs) (see FIG. 3C). In support of this, the division time (DT) of single cells tracked within the population or analyzed as isolated clones was also prolonged for old WT-MDSPCs and ERCC1-deficient MDSPCs compared to young WT-MDSPCs. These data demonstrated that the proliferation capacity of MDSPCs diminishes with age.

Example 3

Figure 9:
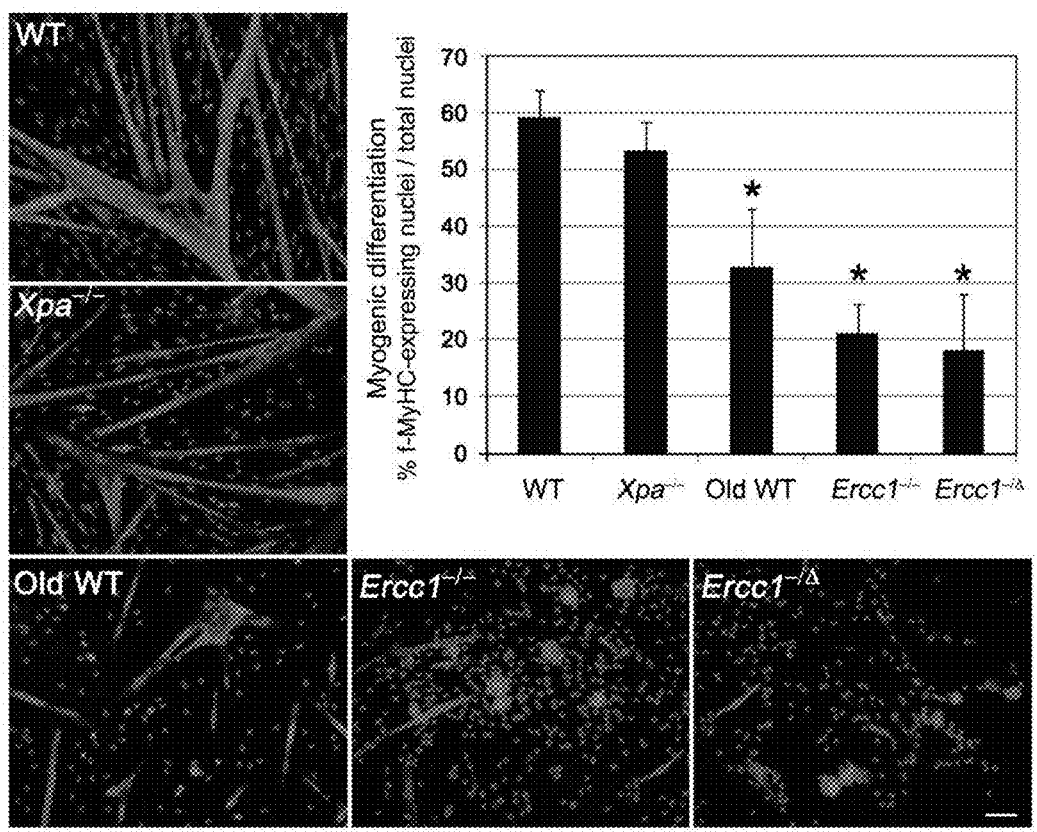
FIG. 9 depicts the in vitro myogenic differentiation of individual MDSPCs (clones). Shown are representative images of clonal myogenic differentiation of MDSPCs isolated from young and old WT mice as well as XPA- and ERCC1-deficient mice. After measuring division time, outgrowth from individual clones were switched to differentiation media (n=3-7 per genotype). After 2-3 days, cells were immunostained for the terminal myogenic marker, f-MyHC. Scale bar=100 μm. Also shown is the quantification of 50 images. Plotted are the average±s.d. Myogenic differentiation [% of cells (DAPI) expressing f-MyHC] was significantly reduced in old WT, Ercc1$^{-/-}$ and Ercc1$^{-/Δ}$ MDSPCs clones relative to young WT and Xpa$^{-/-}$ (*P<0.001, Kruskal-Wallis ANOVA on ranks). These data demonstrate a myogenic differentiation defect in clonal MDSPCs isolated from old WT and progeroid mice, consistent with the cell population studies in FIGS. 3D-3E.
Figure 10:
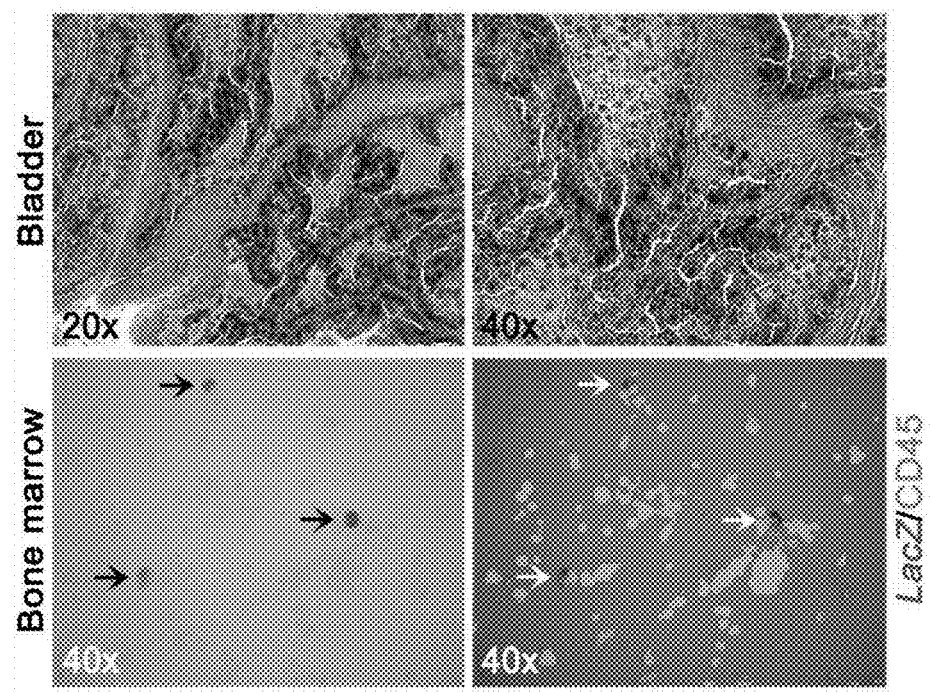
FIG. 10 shows data regarding the effect on bladder and bone marrow in Ercc1$^{-/Δ}$ mice. Mice were injected with 2-4×10$^5$ LacZ+ MDSCs per gram of body weight and euthanized 2-9 weeks later to determine sites of engraftment. Shown are representative images at multiple levels of magnification of stem/progenitor cell engraftment in the bladder/ureter and bone marrow. Bone marrow cells were immunostained with CD45 to identify immune cells, suggesting that some of the MDSPCs can contribute to hematopoietic lineages.
Figure 11:
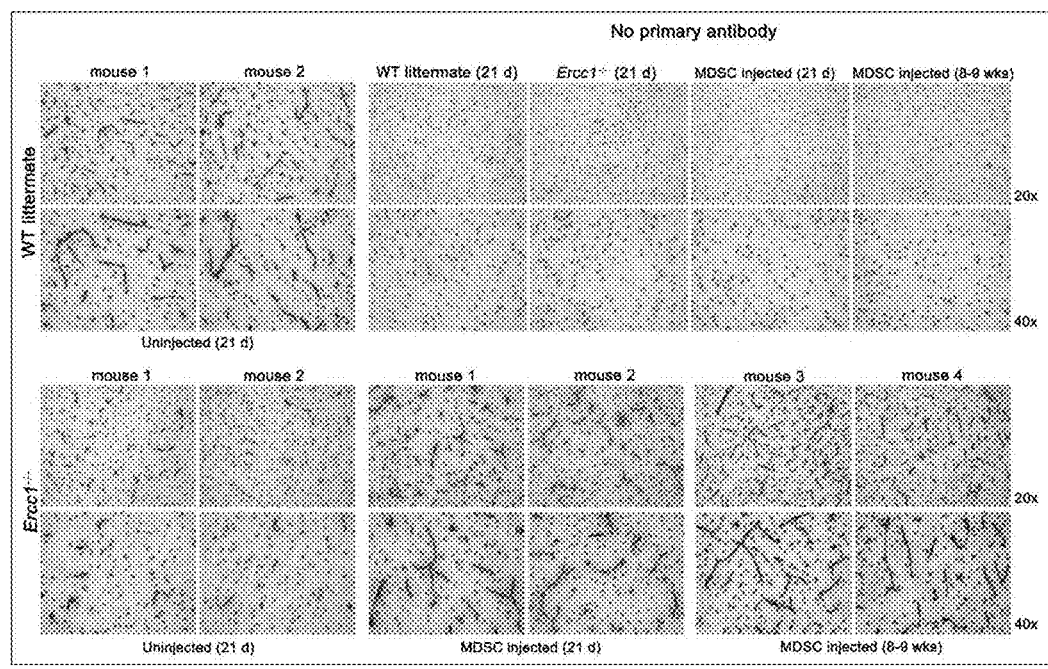
FIG. 11 shows the effect of the treatment of progeroid Ercc1$^{-/-}$ mice with MDSPCs. The treatment showed dramatically improved neovascularization in the cerebral cortex compared to untreated mutant animals. Ercc1$^{-/-}$ mice were administered intraperitoneally with 2-4×10$^5$ MDSPCs per gram of body weight at 17 days of age and tissues harvested 1-9 wks later (same animals as in FIGS. 13A-13B, infra). Tissue sections of the cerebral cortex were immunostained for the endothelial marker CD31 to identify microvasculature. Shown are representative images from two mice per group. Untreated Ercc1$^{-/-}$ mice (lower left panel) showed a significantly decreased vascular area (1.2%) in brain compared to WT littermates (2.5%, upper left panel) at 21 days of age. Progeroid mice injected with young WT-MDSPCs showed significantly improved neovascularization in the brain at 21 days (2.2%) and 8-9 wks (3.2%, lower right panel) post-injection with vascular areas indistinguishable from age-matched WT mice (3.1%, P<0.05, Dunn's test).
Figure 12A:
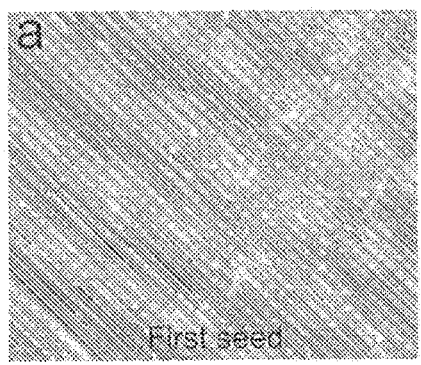
FIGS. 12A-12D depicts MDSPC morphology and maintenance. Representative images indicating (a) (FIG. 12A) the initial density of MDSPCs yielded at pp6 (~200 cells/cm$^2$). (b) (FIG. 12B) MDSPCs maintained at an optimal confluence of <30%. (c) (FIG. 12C) MDSPCs in need of trypsinization and splitting 1:2. (d) (FIG. 12D) MDSPCs ready to be re-plated to eliminate the fibroblast-like cells (arrows). Images are at 5× magnification.
Figure 12B:
Figure 12C:
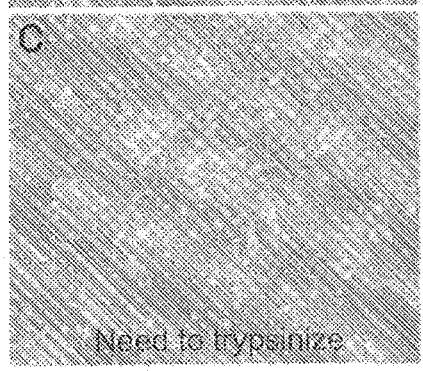
Figure 12D:
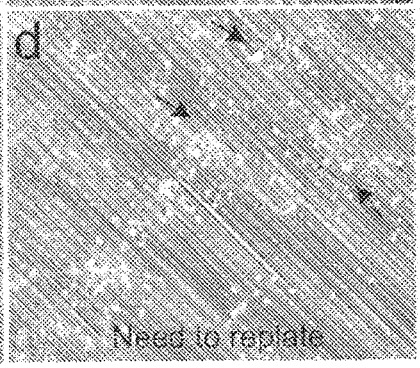
Figure 16:
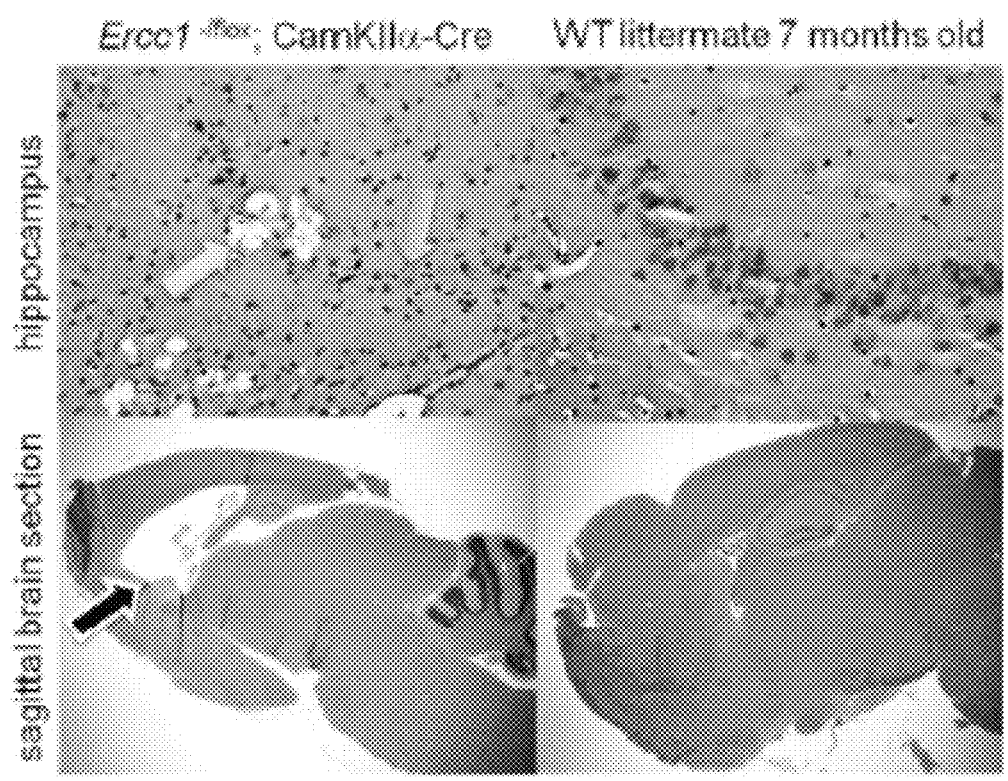
FIG. 16 depicts that deletion of Ercc1 only in the neurons of the forebrain using Cre-lox technology leads to neuronal cell death and profound hydrocephalus. Top panels are 60λ image of the hippocampus showing decreased neurons and spongiform changes in the mutant mouse. Bottom panels are 10× images of whole brain showing profound hydrocephalus in the mutant mice (black arrow).
Figure 17:
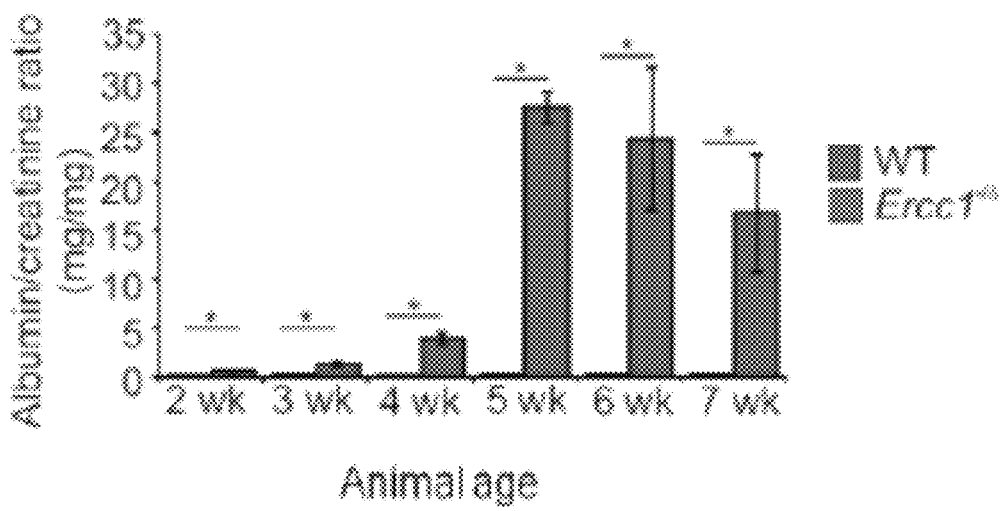
FIG. 17 shows that Ercc1$^{-/\Delta}$ mice has abnormal albumin/creatinine ratio to compensate for urine concentration. This demonstrates renal dysfunction beginning at 4-5 weeks of age.
Figure 18:
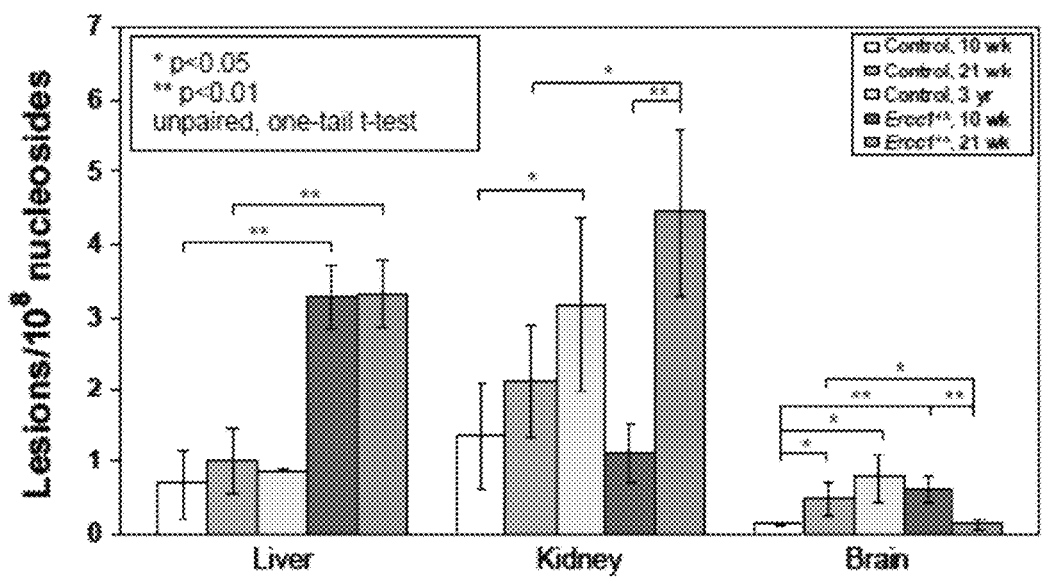
FIG. 18 shows the levels of d(G[8-5m]T) in genomic DNA isolated from the liver, kidney, and brain of Ercc1$^{-/\Delta}$ mice WT littermates or old WT mice (n=3 per/group).
Figure 19:
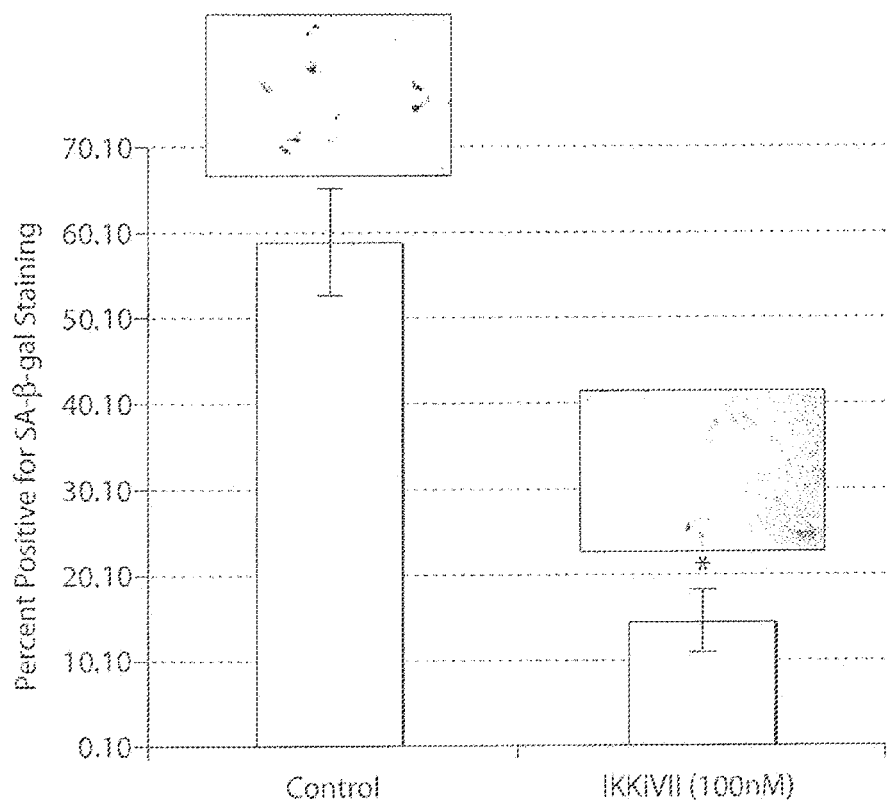
FIG. 19 depicts analysis of the ability of an IKK inhibitor (IKKiVII) to rescue senescence (SA-3-gal+) passage −/− MEFs after 24 hours of treatment.

To determine whether the capacity for myogenic differentiation is affected in old and progeroid MDSPCs, the cells were cultured to confluence and switched to differentiation medium (low serum). The young WT- and Xpa$^{-/-}$ MDSPCs fused to form multi-nucleated myotubes expressing fast myosin heavy chain (f-MyHC), a marker of terminal myogenic differentiation (see FIG. 3D). In contrast, MDSPCs isolated from old WT and progeroid ERCC1-deficient mice formed significantly fewer and smaller myotubes indicating impaired differentiation (see FIG. 3D; *P<0.001; Kruskal-Wallis ANOVA on ranks). The differentiation defect was confirmed by measuring the expression of myogenic differentiation markers, MyHC, desmin, and myogenin (see FIG. 3E). Myogenic differentiation of individual MDSPC clones from old and progeroid mice was also significantly reduced compared to young WT mice (see FIG. 9; *P<0.001, Kruskal-Wallis ANOVA on ranks). Similarly, osteogenic and chondrogenic differentiation of progeroid and old MDSPCs was attenuated compared to cells isolated from young WT mice (see FIG. 3B). In contrast, the capacity for adipogenic differentiation was retained in aged MDSPCs. To determine if this differentiation defect translated in vivo, MDSPCs isolated from progeroid mice were injected intramuscularly (IM) into mdx mice, a model of Duchenne muscular dystrophy. Indeed, cells derived from Ercc1$^{-/\Delta}$ mice had an impaired ability to regenerate muscle fibers in dystrophic muscle compared to young WT-MDSPCs (see FIG. 3F-3G, P<0.001, Mann-Whitney Rank sum test). Cumulatively, these data provide evidence of a significant loss of stemness properties, including proliferation under clonogenic conditions, multipotential differentiation and tissue regeneration, in MDSPC populations isolated from old and progeroid mice.

Example 4

To rule out the possibility that the stem/progenitor cell dysfunction was an artifact caused by extensive passaging of MDSPCs ex vivo, the number of cells with stem/progenitor surface markers and capacity for myogenic differentiation was measured at the earliest possible time point following isolation from skeletal muscle. Preplate 1 and 2 (pp1-2; see FIG. 4A), which constitute all cells directly isolated from skeletal muscle, were induced to differentiate within 24 hrs of isolation. f-MyHC positive myotube formation was impaired in cells isolated from the skeletal muscle of progeroid ERCC1-deficient mice compared to WT littermates (see FIG. 4B). Similarly, expression of a second terminal myogenic differentiation marker, myogenin, was reduced in the ERCC1-deficient cells compared to WT controls (see FIG. 4C). Twenty-four hours post-isolation from skeletal muscle, those cells that remained non-adherent were stained for surface markers Sca-1, CD34 and CD45 and analyzed by FACS to quantify the mixed population of non-hematopoietic stem/progenitor cells in the muscle (see FIG. 4D). Sca-1 is expressed on adult stem cells, a sub-population of myoblasts, muscle-derived fibrogenic/adipogenic progenitors, and a non-myogenic population of cells that emerge in muscle with aging.

Example 5

In young WT mice, ~20% of the cells were Sca-1$^+$/CD34$^+$/CD45$^-$. In contrast, <10% of the cells isolated from old or progeroid skeletal muscle were Sca-1$^+$/CD34$^+$/CD45$^-$. Averaging data from 3-5 populations of each genotype revealed a significant depletion of this population of cells as animals age (see FIG. 4E, *P<0.05; Tukey's test). Next we plated an equivalent number of these sorted cells to directly compare the myogenic differentiation capacity between Sca-1$^+$/CD34$^+$/CD45$^-$ cells from the different genotypes and ages of mice. Myogenic differentiation was significantly impaired in cells isolated from old or progeroid mice compare to young WT mice (see FIGS. 4F-4G, *P<0.001; Kruskal-Wallis ANOVA on ranks). These data demonstrated that there is a loss of MDSPC cell number as well as capacity for myogenic differentiation with aging.

Example 6

Figure 5C:
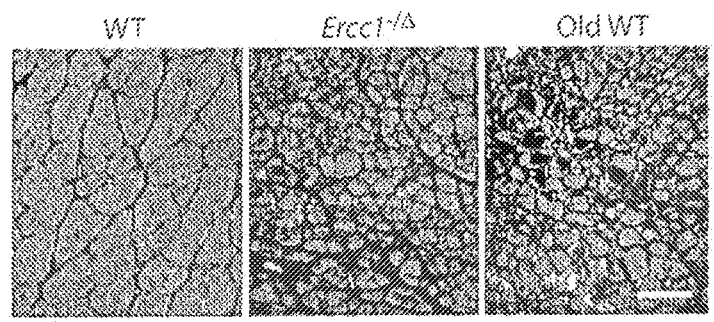
Figure 5D:
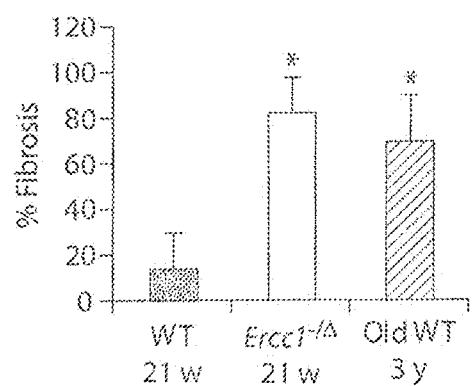

To determine whether there is a difference in the function of muscle stem/progenitor cells between aged and young organisms in vivo, muscle regeneration was examined utilizing a well-established cardiotoxin injury-induced model. The total area of muscle regeneration, as defined by centronucleated fibers, did not significantly differ between young WT-, old WT-, and progeroid mice (see Table 1, supra). However, there was a dramatic difference in the average cross-sectional area of the regenerated myofibers in old and progeroid mice compared to young adult mice (see FIG. 5A). More than 50% of the centronucleated, dystrophin-positive myofibers in old and progeroid mice had an area of ≤500 µm$^2$ (see FIG. 5B). In contrast, >60% of the myofibers in young WT mice had an area of >1000 µm$^2$, indicative of significantly more mature regenerated myofibers (P<0.001; Kruskal-Wallis ANOVA on ranks). In addition, Masson's Trichrome stain revealed increased fibrosis in muscle of old and progeroid mice in comparison to young WT mice following injury (see FIG. 5C and FIG. 5D; *P<0.05; Tukey test). These data demonstrated that muscle regeneration is delayed and impaired in aged organisms.

Collectively, the data presented in FIGS. 4A-4G and 5A-5D supported the conclusion that aged organisms have a muscle stem/progenitor cell defect.

Example 7

To determine if the loss of functional MDSPCs contributes to aging-related degenerative changes, it was examined whether transplantation of young WT-MDSPCs affects either the healthspan or lifespan of progeroid mice. Littermate pairs of Ercc1$^{-/-}$ mice were injected intraperitoneally (IP) with 2-4×10$^5$ young WT-, progeroid-, or old WT-MDSPCs per gram body weight or phosphate buffered saline (PBS) at 17 days of age and lifespan was measured. Ercc1$^{-/-}$ mice injected with young WT-MDSPCs showed pronounced weight gain and a significantly extended lifespan compared to sibling mutant animals injected with vehicle only (see FIG. 1A; *P<0.05, Dunn's test). In an identical experiment, early passage primary mouse embryonic fibroblasts (MEFs) did not affect the growth or lifespan of Ercc1$^{-/-}$ mice (see FIG. 1A). Similarly, MDSPCs isolated from old WT or progeroid Ercc1$^{-/-}$ mice did not have a significant impact on lifespan.

Figure 1B:
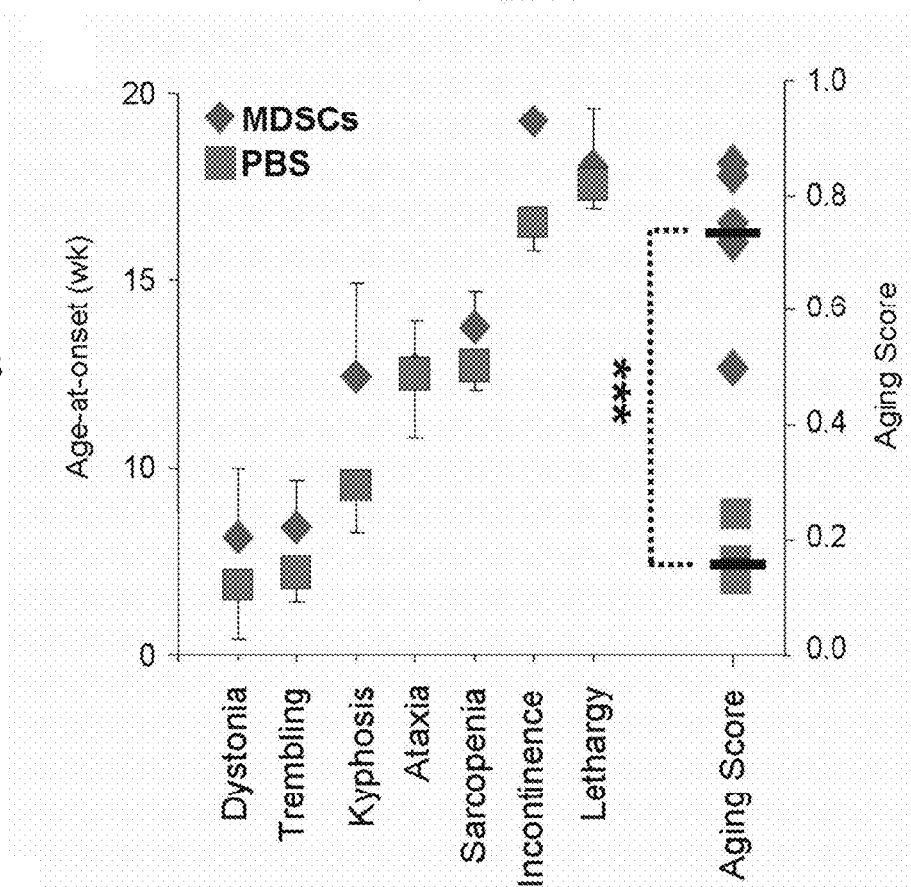

The young WT-MDSPCs were also injected IP into Ercc1$^{-/-}$ mice at 6-7 wks of age and again 6 wks later. The age at onset of characteristic progeroid symptoms, including dystonia, trembling, kyphosis, ataxia, muscle wasting, loss of vision, urinary incontinence and decreased spontaneous activity, was measured biweekly. The results were compared to littermate Ercc1$^{-/\Delta}$ mice treated with vehicle only in a pairwise fashion. The investigators were blinded to the treatment arm. The aging score, representing the fraction of symptoms that were delayed in mutant mice treated with MDSPCs compared to a mutant littermate treated with PBS, revealed a highly significant difference between treatment groups (see FIG. 1B; ***P<0.0008; Student's t-test).

These data provided strong evidence that loss of stem/progenitor cell function plays a direct causal role in aging-related degeneration and that treatment with young WT-MDSPCs extends life and healthspan.

Example 8

To address the question of how MDSPCs could extend healthspan and lifespan, it was examined whether if the donor cells engrafted in host tissues. Young WT-MDSPCs, transduced with a retroviral vector containing LacZ with a nuclear localization sequence (nLacZ), were injected IP into Ercc1$^{-/-}$ mice (n=8). Fourteen tissues were analyzed for the presence of donor cells. LacZ+ cells were detected in the parenchyma of the liver and kidney, as well as connective tissues associated with pancreas and spleen of all mice analyzed (see FIGS. 13A-13B). Similar results were obtained in animals euthanized from 1 to 9 wks post-injection. LacZ+ cells were also detected in lung, esophagus, thymus, bladder/ureter, spinal cord, and bone marrow of at least a single mouse. Importantly, donor cells were not detected in the heart, brain, skeletal muscles, and lymph nodes of any mice. The extent of donor cell engraftment and expansion is limited, indicating that the beneficial effects of MDSPCs is not due to tissue reconstitution by donor cells, as is seen with hematopoietic stem/progenitor cells in bone marrow transplant.

Example 9

Figure 6A:
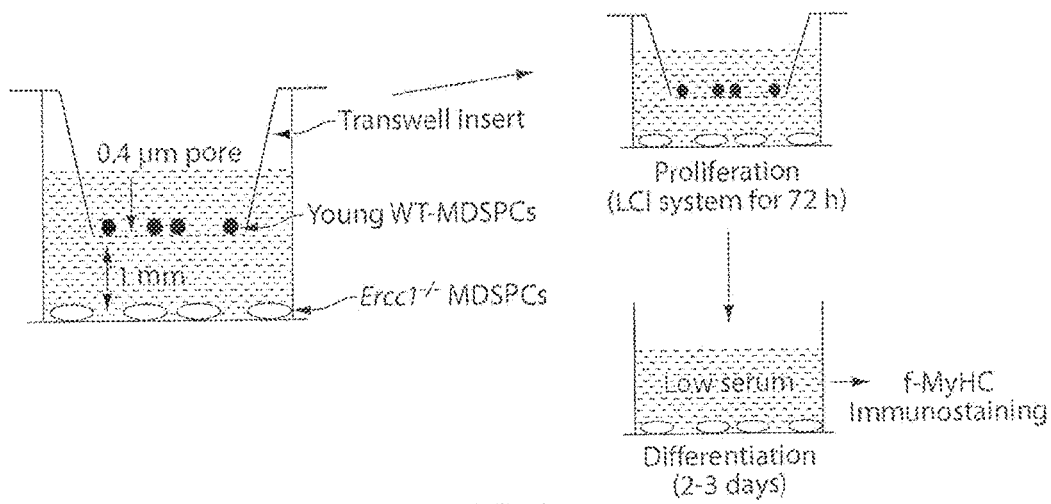
FIGS. 6A-6D depicts measurement of proliferation and myogenic differentiation of MDSPCs isolated from old and progeroid mice after co-culturing the cells with young WT-MDSPCs.
Figure 6B:
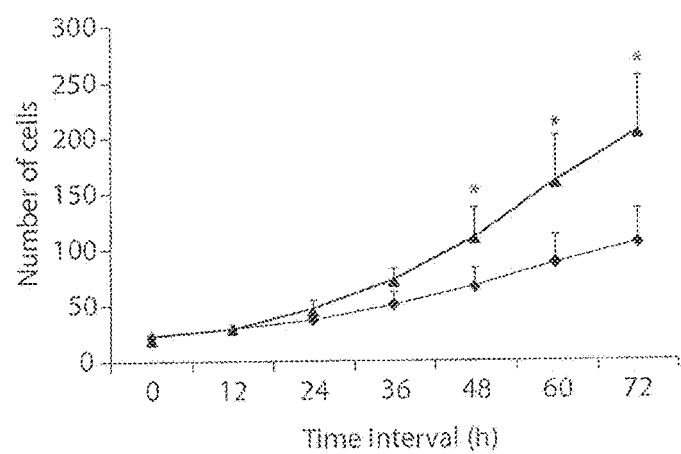

In a progeria model (Ercc1$^{-/-}$ mice), young WT-MDSPCs had a therapeutic effect. However, the duration of the experiment (<3 wks) and the limited extent of engraftment of IP injected MDSPCs made it highly unlikely that this positive effect was a result of substantial MDSPC engraftment, proliferation, differentiation and tissue regeneration. Thus, it was next examined whether young WT-MDSPCs confer their therapeutic effects via a paracrine mechanism, requiring secreted factors. MDSPCs isolated from 14 day-old progeroid Ercc1$^{-/-}$ deficient mice were co-cultured with the young WT-MDSPCs using a transwell system (see FIG. 6A). The proliferation of Ercc1$^{-/-}$ MDSPCs was measured for 72 hrs while the cells were exposed to proliferation media from young WT-MDSPCs. Subsequently, the Ercc1$^{-/-}$ MDSPCs were switched to low serum media to measure myogenic differentiation. The proliferation defect of Ercc1$^{-/-}$ MDSPCs was significantly improved by co-culture of the cells with young WT-MDSPCs (see FIG. 6B, *P<0.001, Mann-Whitney Rank sum test). In addition, myogenic differentiation of Ercc1$^{-/-}$ MDSPCs was improved after co-culture with young WT-MDSPCs (see FIG. 6C). Likewise, impaired differentiation of old WT-MDSPCs was rescued by conditioned media from young WT-MDSPCs.

Figure 7A:
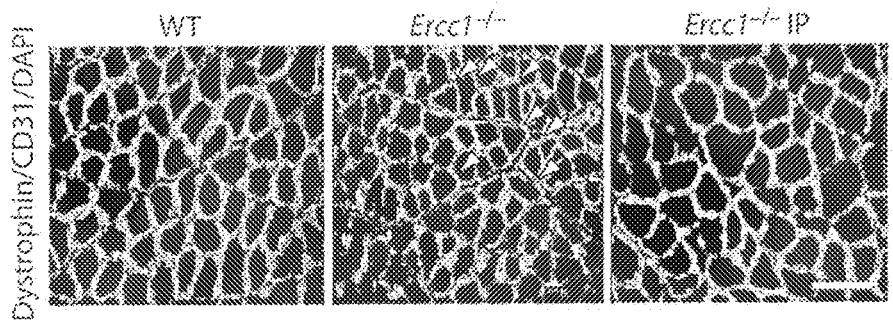
FIGS. 7A-7C depicts a comparison of host skeletal muscle fiber size and tissue vascularization between normal mice, progeroid mice, and progeroid mice treated with intraperitoneal transplantation of young WT-MDSPCs.

To quantify the improvement, MDSPCs from progeroid Ercc1$^{-/-}$ or old WT mice were grown in the presence of conditioned media from young WT-MDSPCs, then harvested for immunodetection of the terminal myogenic differentiation marker MyHC (see FIG. 7D). MyHC expression was dramatically increased (2.5-9×) if the cells were grown in the presence of media from young WT-MDSPCs compared to differentiation media alone.

Thus, young WT-MDSPCs were able to rescue, at least in part, the function (i.e., proliferation and differentiation) of MDSPCs isolated from progeroid and old mice via secreted or released factors.

Example 10

To determine if secreted factors were indeed important for the therapeutic effect of MDSPCs, whether there was evidence of improved histopathology in tissues of treated ERCC1-deficient mice in which transplanted MDSPCs were not detected, in particular, skeletal muscle and brain was examined. Previously, it had been demonstrated that the regenerative potential of MDSPCs transplanted into skeletal muscle, heart and bone correlates with their ability to induce angiogenesis. (See, e.g., Qu-Petersen, Z. et al. *J. Cell. Biol.* 157, 851-864 (2002)). Thus, whether IP injection of young WT-MDSPCs had effects on the vasculature of the brain, as well as muscle fiber size was examined. Muscle sections were stained for dystrophin to highlight muscle fiber perimeter and CD31 to identify endothelial cells within microvessels (see FIG. 7A). For each image, the total number of muscle fibers and CD31+ cells were quantified, and the ratio (# of CD31+ cells/# of muscle fibers) determined. Muscles of 15 day-old Ercc1$^{-/-}$ mice had significantly reduced numbers of CD31+ cells at the periphery of muscle fibers compared to WT littermates (see FIG. 7B, 0.56 CD31+ cells/fiber vs. 1.25 for WT mice, *P<0.001, Students t-test). The average muscle fiber size was also significantly reduced in the Ercc1$^{-/-}$ mice (324 μm$^2$) compared to WT littermates (see FIG. 7B; 734 μm$^2$, *P=0.002, Mann-Whitney Rank sum test).

Figure 7B:
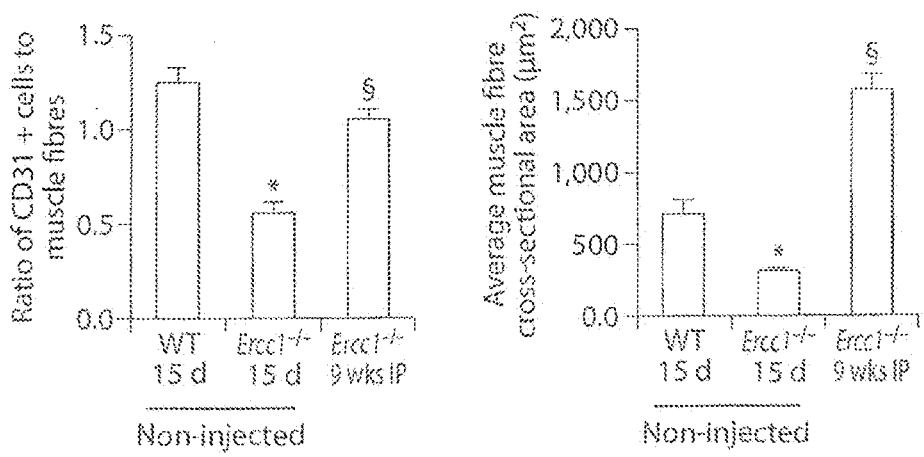

IP injection of young WT-MDSPCs into Ercc1$^{-/-}$ mice led to a significant increase in the number of CD31+ cells 9 wks post-injection compared to untreated Ercc1$^{-/-}$ mice that only live 3-4 wks (see FIG. 7B; 1.05 CD31+ vessels/fiber; § P<0.05, Tukey test). Similarly, muscle fiber size significantly increased (see FIG. 7B; 1580 μm$^2$ cross-sectional area; § P<0.05, Dunn's test). It is impossible to directly compare the fiber size between Ercc1$^{-/-}$ mice transplanted with young WT-MDSPCs to untreated mutant animals of the same age since the latter don't live to 9 wks of age (see FIG. 1A). Nevertheless, unprecedented muscle regeneration and growth was evident in Ercc1$^{-/-}$ mice treated with MDSPCs.

Figure 7C:
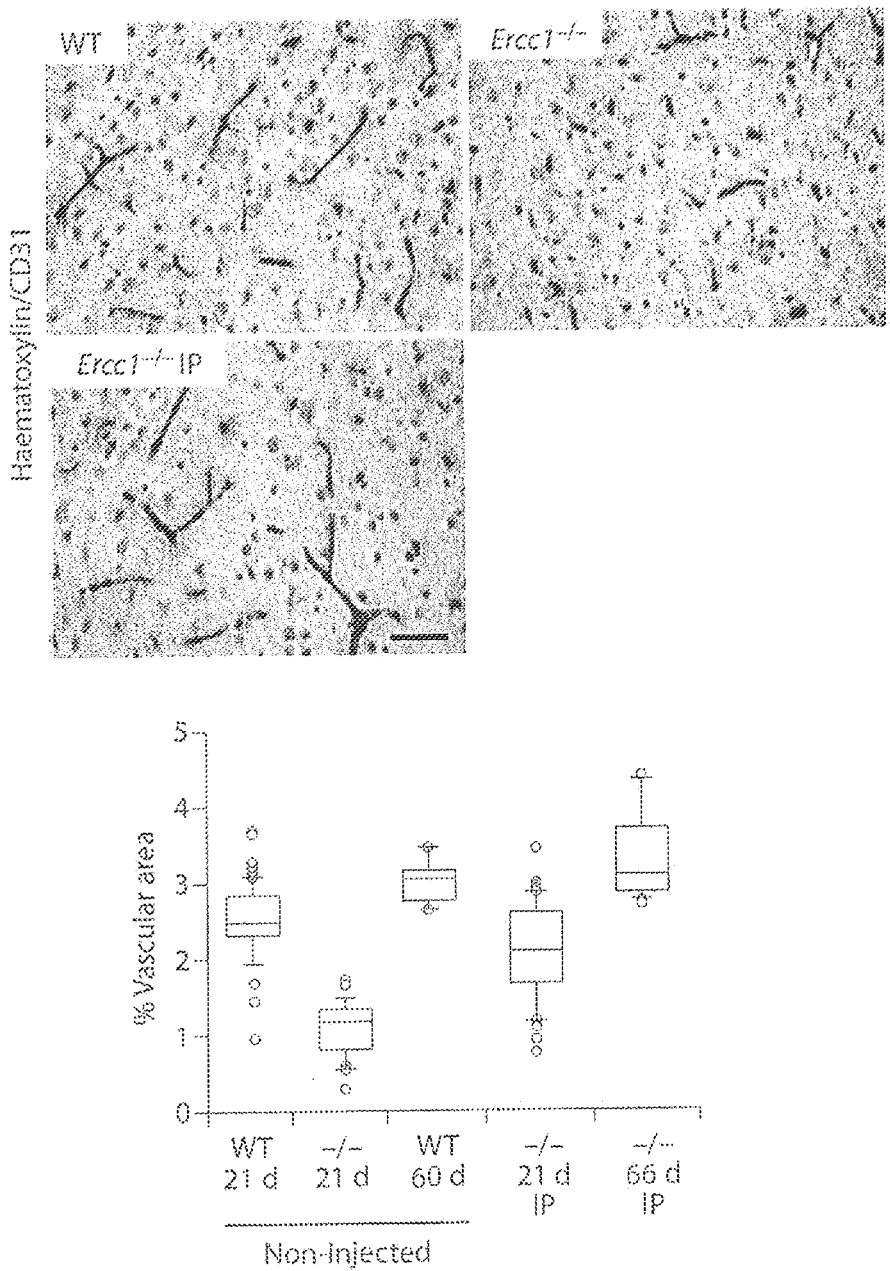

Progeroid Ercc1$^{-/-}$ mice show reduced vascularization in the brain compared to WT littermates at 3 wks of age (see FIG. 7C).

Table 5 lists the primers used to measure expression of stem/progenitor surface markers and markers of differentiation.

TABLE 5

| Target gene | Marker of | Forward | Reverse | Amplicon length (bp) |
|---|---|---|---|---|
| Sca-1 | Stem/ progenitor cell | CCTAGTGTGTGCTGCAGA AAGAGC (SEQ ID NO.: 1) | GAGGAAGTCTTCACG TTGACG (SEQ ID NO.: 2) | 243 |
| CD34 | Stem/ progenitor cell | GCAGCTTTGAGATGACAT CACC (SEQ ID NO.: 3) | CTCAGCCTCCTCCTT TTCACA (SEQ ID NO.: 4) | 280 |
| Desmin | Myogenic | AACCTGATAGACGACCTG CAG (SEQ ID NO.: 5) | GCTTGGACATGTCCA TCTCCA (SEQ ID NO.: 6) | 258 |
| Myogenin | Myogenic | CTACAGGCCTTGCTCAGCT C (SEQ ID NO.: 7) | AGATTGTGGGCGTCT GTAGG (SEQ ID NO.: 8) | 200 |
| MyHC | Myogenic | GAATGACGGACGCCCAGA TG (SEQ ID NO.: 9) | ACTGGCAGCCACTTG TAGGG (SEQ ID NO.: 10) | 400 |

TABLE 5-continued

| Target gene | Marker of | Forward | Reverse | Amplicon length (bp) |
|---|---|---|---|---|
| Col-I | Osteogenic | CCTGAGTCAGCAGATTGA GAACA (SEQ ID NO.: 11) | CCAGTACTCTCCGCT CTTCCA (SEQ ID NO.: 12) | 115 |
| Col-II | Chondrogenic | TCTGGTAAAGAAGGCCCT GTG (SEQ ID NO.: 13) | GTCCAGGGAATCCGA TGTTG (SEQ ID NO.: 14) | 106 |
| PPARγ | Adipogenic | Qiagen Inc. Nm_011146 (QT00100296) | | 144 |
| β-actin | Loading Control | AAGAGCTATGAGCTGCCT GA (SEQ ID NO.: 15) | TGGCATAGAGGTCTT TACGG (SEQ ID NO.: 16) | 111 |

Although donor cells were not detected in the brain of Ercc1$^{-/-}$, cell transplantation significantly improved neovascularization in the brain of these progeroid mice. In 3 wk-old Ercc1$^{-/-}$ mice, the median area of cerebral cortex occupied by vasculature was 1.2%. In Ercc1$^{-/-}$ mice injected with MDSCPs, vascularization increased approximately to the levels in 3 wk-old WT mice (2.2% vs. 2.5%, respectively) and the improvement was sustained. Ercc1$^{-/-}$ mice treated with MDSPCs that survived out to 9 wks of age, had a vascular area indistinguishable from age-matched WT mice (3.2% vs. 3.1%, P<0.05, Dunn's test).

These data demonstrated that there is improvement in the histopathology of several tissues in which donor cell engraftment was not detected, suggesting that MDSPCs exert their therapeutic effect via secreted or released factors.

Figure 8A:
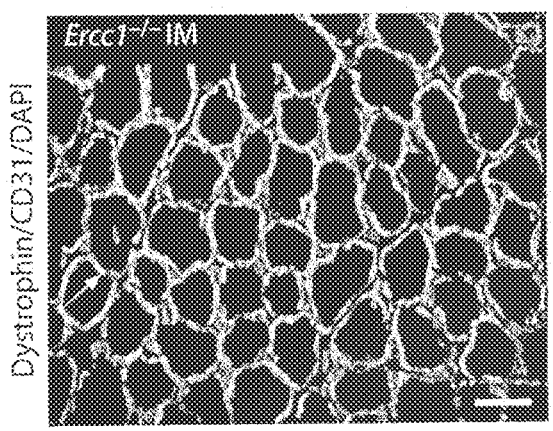
FIGS. 8A-8E depicts the measurement of host muscle fiber size and tissue vascularization after intramuscular transplantation with young WT-MDSPCs.
Figure 8B:
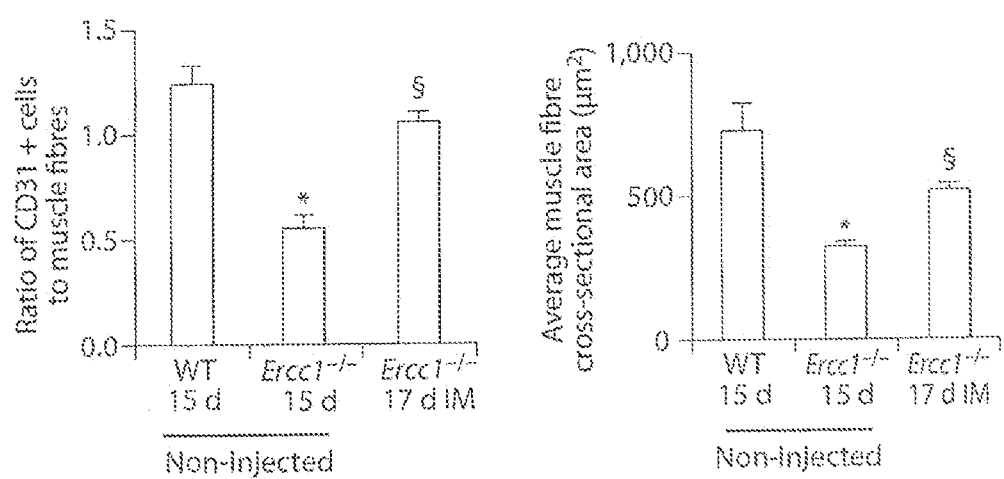
Figure 8C:
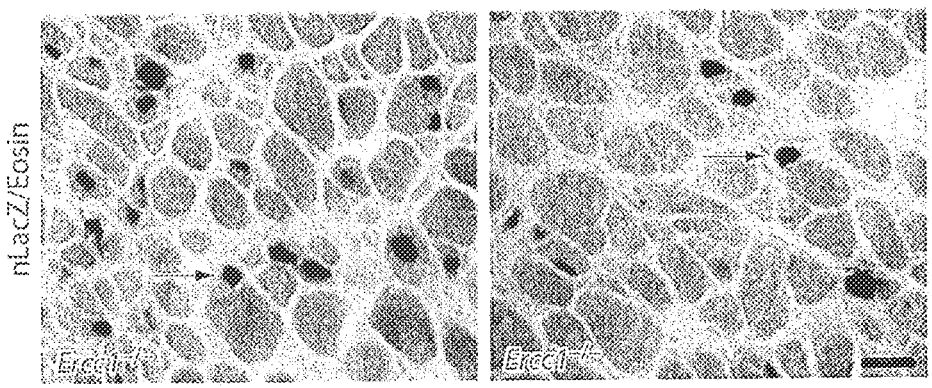
Figure 8D:
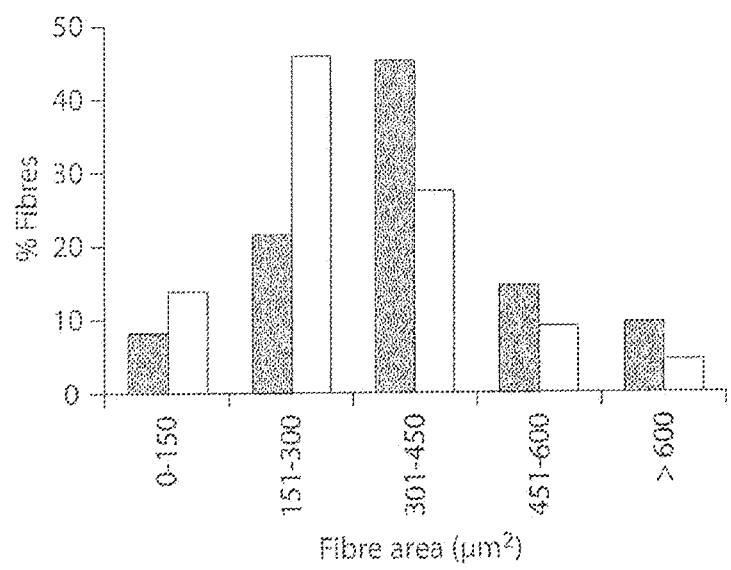
Figure 8E:
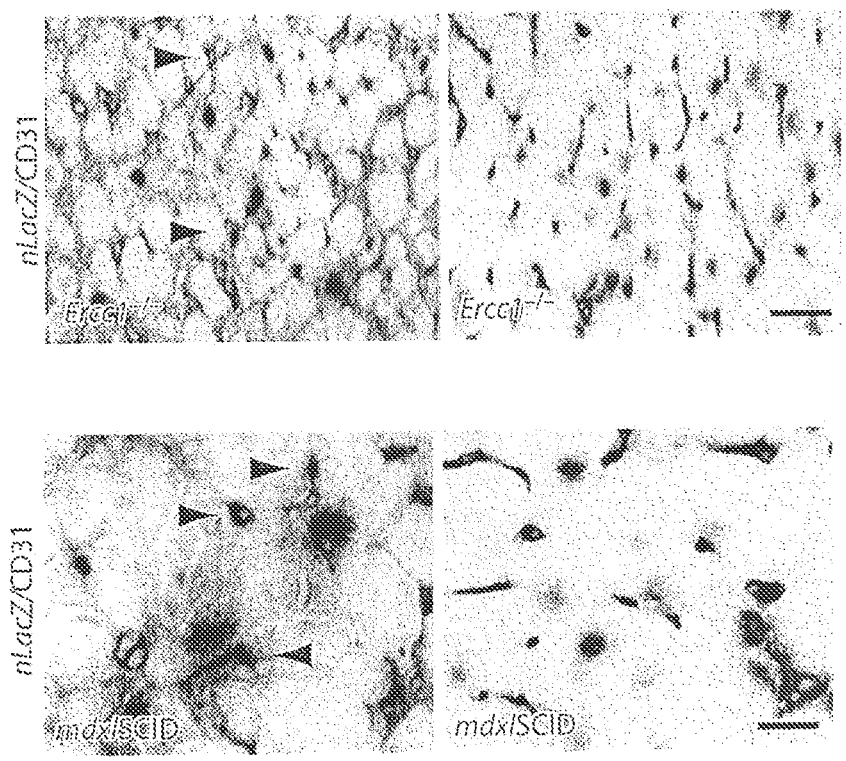

Using IM injection of nLacZ-labeled MDSPCs to localize donor cell engraftment, host muscle were analyzed for presence of LacZ+ myofibers and endothelial cells). Like IP, IM administration of young WT-MDSPCs into Ercc1$^{-/-}$ mice (see FIG. 8A, n=3 mice per group) led to a significant increase in the number of CD31+ cells (see FIG. 8B; 1.06 CD31+ vessels/fiber; $^§$ P<0.05, Tukey test) compared to the non-injected Ercc1$^{-/-}$ mice (0.56 CD31+ vessels/fiber). The muscle fiber cross-sectional area was also significantly increased (see FIG. 8B; 522 μm$^2$ vs. 324 μm$^2$, $^§$ P<0.05, Dunn's test). At the site of injection, numerous myofibers with central or peripheral LacZ+ nuclei were identified, demonstrating that transplanted MDSPCs have the capacity to integrate into regenerated muscle fibers (see FIG. 8C). In addition, analysis of sections of the gastrocnemius distant from the injection site revealed a shift in the distribution of myofiber size towards larger regenerating fibers compared to contralateral non-injected muscle (see FIG. 8D, P<0.001, Mann-Whitney Rank sum test at 151-300 and 301-450). This suggests that IM injection of MDSPCs also affected host myofibers via a paracrine mechanism, requiring secreted factors. Sections were also stained with X-gal and for CD31 to determine if donor cells co-localize with CD31+ cells (see FIG. 8E). Background staining in Ercc1$^{-/-}$ mice was extensive, compared to mdx/SCID mice, likely due to interstitial fibrosis. In both cases, there was a lack of co-localization of LacZ and CD31 staining. These data are consistent with previous findings and the conclusion that transplanted MDSPCs do not directly contribute to blood vessels and thus likely drive host angiogenesis through secreted factors.

Figure 6C:
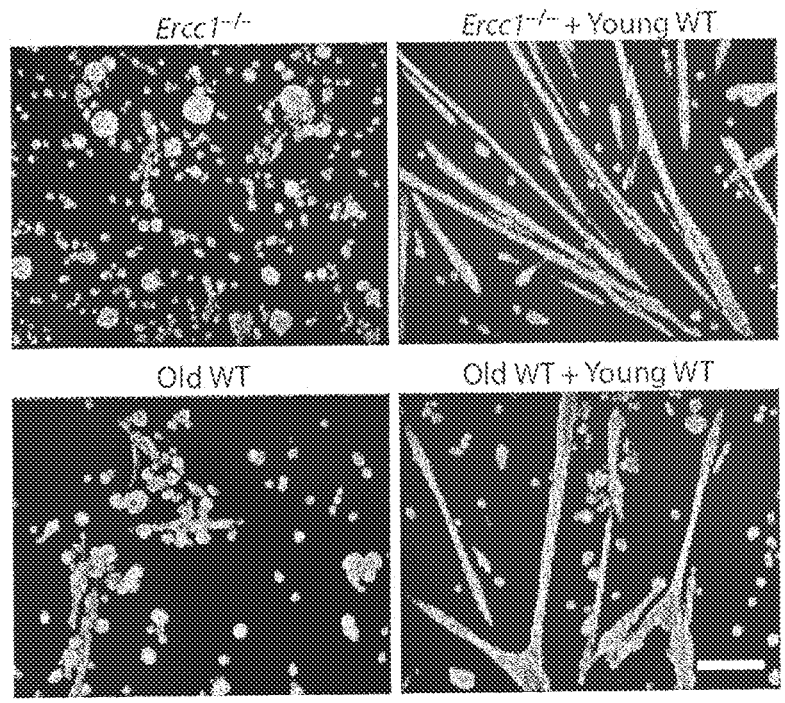
Figure 6D:
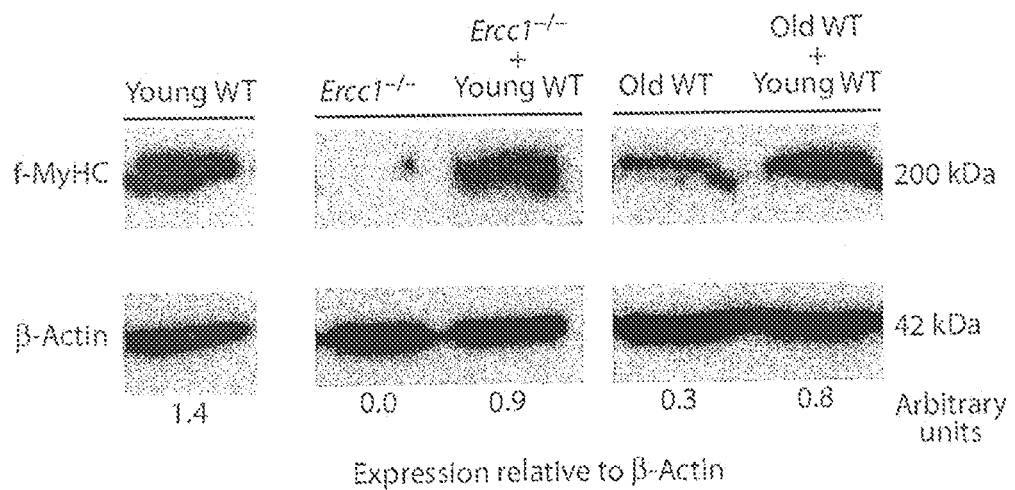

Interestingly, the function of MDSPCs from aged mice could be restored if they were co-cultured with young WT-MDSPCs (see FIG. 6C). Similar results were seen in vivo using parabiosis. These observations demonstrate that old, dysfunctional MDSPCs can be rescued by exogenous factors, rather than the cells being inherently defective. This is in contrast to aged hematopoietic stem cells, which appear to have an intrinsic defect. (See Brunet, A. et al., Nature 449, 288-291 (2007)).

IP administration of young WT-MDSPCs to progeroid mice promoted growth of the animals, decreased muscle atrophy, and stimulated neovascularization in the brain and muscle, despite the fact that donor cells were not detected in these tissues. In addition, transplantation of young WT-MDSPCs directly into progeroid muscle led to muscle regeneration as well as host neovascularization, demonstrating a paracrine mechanism requiring secreted factors. These observations suggested that the mechanism by which MDSPCs promote healthspan and lifespan extension is likely via the secretion or release of stimulatory factor(s) that promote regeneration and also suggest that cells from old hosts lose this secretory phenotype. This stimulatory factor may be necessary to overcome systemic or local negative regulators of tissue regeneration in aged hosts. Identification of these secreted factors and methods to rejuvenate adult stem cells ex vivo will be critical for regenerative medicine.

The data demonstrated that transplanted MDSPCs can have systemic effects, leading to tissue regeneration in multiple organ systems. Therefore, MDSPCs may have therapeutic value for delaying aging-related functional decline and treating human progerias (and related disorders).

Example 11

Example 11 describes experiments from NIH submitted Grant Nos. AR051456, AG032816, and Program Project Grant, entitled "Cell Autonomous and Non-autonomous Mechanisms of Aging," filed with the NIH under Assurance Number A3187-01, each of which is herein incorporated by reference in its entirety.

DNA damage is believed to promote aging through a predominantly cell-autonomous mechanism by triggering programmed cell death or senescence. It is possible that cellular response to DNA damage may be more important in driving the aging process than the DNA damage itself. Moreover, it is also well-established, that in response to high doses of genotoxic stress, cells can secrete senescence-associated factors, which exert a paracrine effect on neighboring cells.

To date, no one has established that non-cell autonomous events occur in response to physiological levels of endogenous DNA damage. However, by using a unique amalgam of tools/expertise it may be possible to determine the mechanism by which DNA damage drives aging. Specifically, such experiments will employ: 1) Mice that spontaneously age rapidly as a consequence of a DNA repair defect (depletion of ERCC1-XPF DNA repair endonuclease), and LC and MS methodology or combinations thereof to accurately measure levels of oxidative DNA lesions that arise spontaneously in the tissues of these mice; 2) Tissue-specific knock-out of ERCC1-XPF to determine if damage accumulation in one tissue affects others; 3) Parabiosis to determine if circulating factors in young healthy mice can rescue the consequences of DNA damage in ERCC1-deficient mice; and 4) Differential mass spectrometry to identify factors in the circulation of progeroid ERCC1 mice that promote aging-related degenerative changes.

1) Measurement of DNA Damage by LC and MS Methodology or Combinations Thereof:

Genomic DNA is isolated from mouse tissues or cell pellets using a high-salt method and digested with a four enzyme cocktail including nuclease P1, phosphodiesterase 1 & 2, and alkaline phosphatase. 15N-labeled standard lesions are subsequently added, including 200 fmol of R-cdG, 150 fmol of S-cdG, 100 fmol of R-cdA, 60 fmol of S-cdA and 10 fmol of d(G[8-5m]T). The enzymes in the digestion mixture are removed by chloroform extraction. The aqueous layer is subjected to off-line HPLC separation for the enrichment of the lesions followed by analysis by LC and MS methodology or combinations thereof using an LTQ linear ion trap mass spectrometer using recently described conditions. This analytical strategy is essential for the reliable quantitation of the endogenous lesions in as little as 10-50 µg of DNA.

The HPLC enrichment step facilitates removal of unmodified nucleosides and buffer used for the enzymatic digestion, which allows for the analysis of the fraction on a capillary HPLC column (0.5×150 mm) and improves the ionization efficiency, providing superb sensitivity (~1 fmol of lesions can be detected).

Compared to the more traditional MS/MS method, the use of LC and MS methodology or combinations thereof provides enhanced specificity. As a result, a single peak is always observed in the selected-ion chromatogram for monitoring the specific transitions of the cyclopurines and d(G[8-5m]T) lesions, which provides accurate quantification of these lesions even at very low levels [e.g., several lesions per $10^8$ nucleosides for d(G[8-5m]T)]. Moreover, the fullscan spectra acquired in LC and MS methodology or combinations thereof mode enable unambiguous identification of the DNA lesions. This is believed to be the first time all four diastereomers of cdA and cdG lesions are measured in genomic DNA isolated from tissues of healthy animals.

Samples.

These assays are applied to tissues from $Ercc1-/\Delta$ mice and the results compared to WT littermates. The tissues to be analyzed are those for which it has previously established that there is aging-related pathology and for which an adequate sample size can be obtained from a single mouse (10-50 µg of DNA). This includes the liver, kidney, bone marrow, brain, and skeletal muscle. Samples are collected from mice at two ages before pathology is detected in that tissue, the age at which pathology is first detected, and when pathology is most prominent. For example, by 7 wks of age liver function tests are already modestly but significantly elevated in $Ercc1^{-/\Delta}$ mice. By 21 weeks of age, LFTs have exceeded that of 34-36 month old WT mice. Hence, DNA damage levels will be measured in liver from 4, 6, 8 and 21 week-old $Ercc1-/\Delta$ mice. The goal is to catch the peak level of DNA damage, which may occur before, during or after the onset of pathology, depending on the cellular response to damage (death or senescence). Three to five mice per group is adequate to detect significant differences in levels of oxidative lesions between WT and DNA repair-deficient mice.

The same tissues from multiple ages of WT mice are analyzed (pre-puberty 6 wks, adult 21 weeks; middle age 18 months; old age >30 months), which will reveal whether endogenous DNA lesions accumulate with aging and whether this correlates with tissue-specific degenerative changes observed with normal aging. In addition, the levels of DNA lesions in tissues from $Ercc1^{-/\Delta}$ mice in which the levels of mitochondrial ROS are altered genetically or pharmacologically will be measured. These experiments are critical for determining whether there is a significant correlation between levels of endogenous DNA damage and aging-related pathology.

Additionally, DNA damage is quantitated in tissues and cells from ERCC1-deficient mice in which NF-κB stress signaling is inhibited. Preliminary data indicate that NF-κB activation in response to genotoxic or inflammatory stress promotes ROS production, supporting a model in which aging-related degeneration is driven, at least in part, by signaling mechanisms that promote more damage in a feed-forward mechanism.

2) Genetic Approaches:

Tissue-specific knock-out of Ercc1 offers a unique opportunity to determine whether DNA damage drives aging through a cell autonomous or non-autonomous mechanism. If it is the former, then one expects cellular abnormalities, pathology and loss of organ function only in the tissue in which Ercc1 is deleted. If it is the latter, one expects increased cell death and/or senescence and aging-related degenerative changes characteristic of the $Ercc1-/\Delta$ mice in more than one tissue. This approach will also enable identification of the tissue that is most vulnerable to endogenous DNA damage and is life-limiting for $Ercc1-/\Delta$ mice.

Methods. Mice.

Tissue-specific deletion of Ercc1 is accomplished by crossing Ercc1-/flox mice with transgenic mice expressing Cre from a tissue-specific promoter. Preliminary data demonstrate the feasibility of this approach. The focus is on deletion of Ercc1 in liver and kidney based on the fact that both tissues demonstrate profound, progressive aging-related pathology in $Ercc-1^{-/\Delta}$ mice. Furthermore, there is an accumulation of endogenous DNA damage in these tissues as $Ercc1^{-\Delta}$ a mice age. Therefore, if DNA damage drives aging via a cell non-autonomous mechanism, liver and kidney may drive it.

To knock-out Ercc1 in hepatocytes, transgenic mice expressing Cre from the albumin and/or alpha-fetal protein promoters are used. To knock-out Ercc1 in the kidney, Nphs2-Cre and γGT-Cre are used. Nphs2/podocin is expressed in glomerular podocytes, while γGT/gamma-glutamyltransferase 1 is expressed in the proximal tubular epithelia. Preliminary data indicate that the podocytes are adversely affected in $Ercc1^{-/\Delta}$ mice before the renal tubular epithelia. Comparing and contrasting pathology in these two kidney-specific knock-outs will reveal if damage to podocytes is sufficient to drive pathology in renal tubular epithelium (i.e., a paracrine mechanism of aging).

Ercc1 is knocked-out in endothelial cells, differentiated muscle and differentiated hematopoietic cells. Characterization of all of these tissue specific knock-outs will be similar. The goal is to determine whether increased DNA damage in one tissue is sufficient to drive senescence, ROS production, mitochondrial dysfunction, NF-κB activation, stem cell dysfunction in that tissue only—or in neighboring cell types and other tissues as well.

Analyzing Tissue Specificity.

To confirm that Ercc1 (and therefore DNA repair) has been genetically depleted in one tissue only, ERCC1 expression is measured in the liver, kidney, brain, bone marrow and spleen of the animals and compared to WT controls and Ercc1$^{-/\Delta}$ mice, using immunoblot or immunofluorescence. Likewise, the levels of cyclopurines are measured in the liver, kidney and bone marrow of these mice. In the targeted tissue, cyclopurines adduct levels should be similar to the levels in Ercc1$^{-/\Delta}$ mice. But, the adduct levels in other tissues should be closer to WT levels.

Measuring the Impact on Organ Function and Tissue Pathology.

The phenotype of tissue-specific Ercc1 knock-outs are evaluated at 2 and 5 months of age and compared to Ercc1$^{-/\Delta}$ mice. A third cohort of tissue specific knock-outs is developed to measure lifespan and end-of-life pathology. Serum chemistries and urinalysis are used to measure organ function (liver, kidney, pancreas, muscle). The mice are necropsied and tissue sections from multiple organs examined for pathology and compared to Ercc1-A mice by the veterinary pathologist. In addition, the following staining techniques are used to measure cell death, cell senescence, ROS production and mitochondrial function.

Measuring Cell Senescence.

Senescence is measured by staining for senescence-associated beta-galactosidase (SA β-gal) activity. Frozen tissue sections are fixed with 0.25% glutaraldehyde and 2% paraformaldehyde for ten minutes at room temperature. The samples are rinsed 3× with PBS then stained with X-gal solution (1 mg 5-bromo-4-chloro-3-indoyl β-D-galactoside and 20 mg dimethylfomamide per ml in 40 mM citric acid/sodium phosphate buffer pH 5.8, with 5 mM potassium ferrocyanide, 5 mM potassium ferricyanide, 150 mM NaCl and 2 mM MgCl2). Additional measures of senescence are loss of proliferation (Ki67 or PCNA immunostaining), increased expression of p16 (immunoblot or IVIS imaging of mice/tissues harboring a p16-luciferase transgenic reporter) and γH2AX foci.

Measuring Cell Death.

Tissues are fixed in 10% formalin for 2 hours, cryoprotected in 30% sucrose overnight, frozen using chilled 2-methylbutane, and sectioned using a cryostat by standard procedures. Cleaved caspase-3 (Cell Signaling Technology) is used at a dilution of 1:250 with a 4° C. overnight incubation. Alternatively, TUNEL staining can be used to measure apoptotic cells in tissue (INVITROGEN®).

Measuring ROS and Mitochondrial Morphology.

ROS levels are measure in vivo using immuno-spin trapping of protein-centered radicals. Mice receive DMPO (5,5-dimethyl-1-pyrroline-N-oxide, Alexis Biochemicals), (2 g/kg total) in 3 doses 24, 12 and 6 hr prior to sacrifice. DMPO is dissolved in pyrogen-free saline and delivered i.p. At sacrifice, tissue and organs are collected, immediately frozen in liquid N2 and stored at −80° C. until analysis. Detection of DMPO-protein adducts is determined by immunoblot. Briefly, tissues are homogenized in Chelex-treated PBS, pH 7.4, containing 100 μM DTPA and centrifuged at 3,000 RPM at 4° C. for 20 min. After SDS PAGE and transfer to PVDF membranes. DMPO-adducted proteins are measured using a 1° rabbit polyclonal anti-DMPO antibody (1:1000, Oxford Biochemicals) followed by a goat anti-rabbit 2° antibody (1:5000, Upstate Biotechnologies). Blots are developed using ECL-plus chemiluminescence (GE/Amersham). Protein concentrations are determined using the BCA assay (Pierce). Alternatively, confocal analysis of tissue protein oxidation is used to semi-quantitatively identify in which tissues there is increased ROS production. Tissues from DMPO-injected mice are gently flushed with saline to remove blood followed by fixation in 3.5% PFA in PBS (pH 7.4) for fixation. Tissues are placed in 30% sucrose for 24 hr, then sectioned (70 μm). Tissue sections are permeabilized with 0.1% Surfact-Amps-X-100 for 1 hr. After blocking with 0.1% BSA in PBS, staining for DMPO-protein radicals is accomplished using a 1° polyclonal anti-DMPO antibody (Oxford Biochemical) and ALEX-AFLUOR® 568 anti-rabbit 2° antibody. Background fluorescence is assessed by applying only the 2° antibody. Tissue sections are mounted on microscope cover glasses and analyzed under a confocal laser microscope (Zeiss). Semi-quantitation of the fluorescence signal (mean fluorescence intensity) is accomplished by converting all images to grayscale followed analysis with Scion Image software. Mitochondrial morphology is examined by electron microscopy.

3) Parabiosis:

Heterochronic parabiosis (i.e., surgical pairing of young and old mice leading to anastomosis of their circulatory systems) revealed that old mice have systemic factors that suppress muscle stem cell proliferation and myogenic differentiation, hepatocyte proliferation and neurogenesis. In contrast, blood of young mice contains factors that can reactivate myelination and muscle stem cell function in old mice.

These data strongly support the notion that aging is driven, at least in part, by endocrine (systemic) factors. However, parabiosis has never been attempted in mice in which the primary cause of aging is chronic stochastic damage. Pairing of DNA repair-deficient Ercc1$^{-/\Delta}$ mice with WT littermates is a critical experiment for determining the mechanism by which stochastic DNA damage promotes aging-related degeneration. Parabiosis is done between Ercc1$^{-/\Delta}$; p16-luciferase and young WT mice. Endpoints measured include all of those used for quantifying aging-related pathology, cellular senescence, mitochondrial function and DNA damage. Preliminary data indicates parabiosis between WT and Ercc1$^{-/\Delta}$ mice is feasible. Conjoined mice have survived >2 months post-surgery and gained weight. Additionally, preliminary data indicate that a p16-luciferase transgene can be used to detect increased senescence in tissues of progeroid Ercc1$^{-/\Delta}$ mice relative to WT littermates. Heterochronic parabiosis between young WT and old p16-luciferase mice is also done to determine if blood-borne factors from young mice affects the amount of senescent cells that accumulate in tissues with normal aging.

Ercc1$^{-/\Delta}$; NF-κB-eGFP or old NF-κB-eGFP mice are anastomosed with young WT mice to determine if circulating factors in young mice suppress the activation of NF-κB, which occurs with accelerated and normal aging. If parabiosis of an Ercc1−/Δ mouse with a young healthy mouse delays or attenuates aging symptoms and degenerative diseases in the mutant mouse, it will extend the results of the heterochronic experiments and demonstrate that aging-related changes, definitively initiated by stochastic cellular damage, are driven, at least in part, by circulating factors.

If it is discovered that parabiosis of an Ercc1$^{-/\Delta}$ mouse with a young healthy mouse reduces the amount of oxidative DNA damage in the mutant animal, this cannot have occurred because DNA repair was restored in ERCC1-deficient mice. Instead, it must be the consequence of something in the circulation of young mice that suppresses ROS in the "aged" mouse, which would be consistent with a model in which increased ROS production, likely as a consequence of mitochondrial dysfunction, is a critical contributor to aging, and would be consistent with preliminary data indicating that ROS levels are greater in ERCC1-deficient cells and mice. However, this outcome would be quite unanticipated in a system where nuclear DNA damage is driving aging and would strongly support a cell nonautonomous mechanism of aging as a consequence endogenous damage.

Parabiosis.

Mice are anesthetized with xylazine and ketamine HCl (10 mg/kg & 100 mg/10 kg body weight, respectively) by i.p. injection and joined by a modification of the technique of Bunster and Meyer. The corresponding lateral aspects of each mouse is shaved and sterilized with betadine. Matching skin incisions are made from the olecranon to the knee joint and the subcutaneous fascia is dissected to create ½ cm of free skin. The olecranon and knee joints are attached by a single 2-0 silk suture and tie, and the dorsal and ventral skins are approximated by staples. Cross-circulation is confirmed by tracking flow of Evans blue dye from one mouse to the other following i.v. injection.

In Vivo Imaging for Senescence.

Mice harboring the p16 luciferase reporter are injected 10 min prior to imaging with 300 mg/kg luciferin (Gold Bio-Technology) reconstituted in PBS, intraperitoneally. The mice are anesthetized using isoflurane and then imaged on black paper using IVIS200® (Caliper Life Sciences) for 2 min on medium binning. For terminal experiments, the mice are euthanized by CO2 inhalation, the organs dissected and imaged in the same manner to view organ-specific luminescence.

4) Proteomics:

Proteomics can be used to compare the profile of circulatory proteins in Ercc1$^{-/\Delta}$ mice or mice in which Ercc1 is tissue-specifically deleted to that of young WT mice to identify systemic signals activated in response to DNA damage and with old age.

Heterochronic parabiosis experiments revealed that "old" mice have circulating factors that negatively impact tissue regeneration in "young" mice. This experiment is designed to reveal if the same holds true in mice in which accelerated aging is driven by stochastic damage and the goal of this experiment is to identify those factors. Modern protein mass spectrometry methods are focused on the measurement and identification of secreted factors that change with age and are driven by DNA damage. This problem is studied using a combination of 1) unbiased and 2) targeted proteomic experiments.

Differential Mass Spectrometry (dMS) is an efficient MS-based strategy for comparing complex biological samples, including plasma and cellular extracts. This unbiased analysis of all ions detected by high resolution Fourier transform mass spectrometry, not just ions that have corresponding MS/MS spectra and peptide sequences, is a powerful approach for discovering biologically relevant peptides and proteins, and this technique was used successfully to identify candidate plasma and cerebral spinal fluid markers that track with disease progression and/or respond to treatment with specific classes of drugs. An important advantage of the dMS approach is that it is not limited to the analysis of tryptic peptides and has been successfully applied to the identification of intact plasma peptides and proteins. To enable the detection of molecules present at low abundance, a variety of classical biochemical sample preparation methods (e.g. ultrafiltration, strong cation exchange chromatography, immuno-depletion, etc.) are used to fractionate the proteome.

Targeted proteomics is a method that allows specific peptide and protein candidates to be measured with high sensitivity, selectivity, precision, and speed. Peptides discovered with dMS or culled from the literature are measured with targeted proteomic assays across multiple model systems with similar symptoms (e.g., old mice, progeroid mice and senescent cells). In this fashion, novel peptide markers that share similar amino acid sequences can be readily converted to targeted assays that translate between in-vitro systems, pre-clinical animal models, and human samples.

The ultimate goal is to identify proteins that are found in the circulation of old WT mice but not young mice. This is facilitated by also comparing the serum of progeroid mice to their WT littermates and senescent cells to non-senescent cells. These latter experiments are much more rapid and support longitudinal study designs that are powerful for observing important differences that occur with time and treatment. Several interventions have been demonstrated to delay the onset of aging-related degenerative changes in the Ercc1$^{-/\Delta}$ mice (chronic treatment with the mitochondrial radical scavenger XJB-5-131; chronic inhibition of NF-κB activation; transplantation with young adult stem cells).

The transcription factor NF-κB is activated in response to different types of cellular stress including chronic inflammatory, genotoxic and oxidative stress and is upregulated in multiple tissues with aging. However, it is not known what cell types NF-κB is activated in during aging and what is driving activation. It also is not known whether NF-κB activation drives age-associated degenerative changes through cell autonomous or non-autonomous pathways or is a just a consequence of aging. In particular, these experiments challenge the paradigm that NF-κB is activated with aging primarily in response to inflammation and subsequently drives aging through solely cell autonomous mechanisms. Instead, the hypothesis that NF-κB activation is initially cell autonomous, initially occurring only in cells that are experiencing genotoxic and/or oxidative stress will be explored. NF-κB then regulates cell proliferation and function through both cell autonomous and, in particular, non-autonomous mechanisms. This hypothesis is based on extensive preliminary data demonstrating increased NF-κB activity in a mouse model of accelerated aging (Ercc1$^{-/\Delta}$) due to a defect in nuclear DNA repair, and in naturally aged mice that have accumulated oxidative DNA damage.

DNA Damage.

Based on preliminary results, a novel model is proposed where stochastic accumulation of cellular damage, in particular DNA damage, induces NF-κB in a cell autonomous manner, which then regulates ROS and senescence to drive aging through non-cell autonomous pathways. Moreover, the increase in ROS and/or senescence feeds back through cell autonomous (e.g. intracellular ROS) and nonautonomous (e.g. SASP) pathways to increase DNA damage, NF-κB activation and ROS to accelerate aging further. This model also predicts that an increase in NF-κB activity or ROS through other pathways (e.g. cellular damage, inflammation) will result in increased DNA damage and subsequent further activation of the pathway.

This model is supported by preliminary data in ERCC1-deficient MEFs and in Ercc1$^{-/\Delta}$; NF-κBeGFP reporter mice and in Ercc1$^{-/\Delta}$ mice with reduced NF-κB activity as well as by recent studies showing ablation of senescent cells improves healthspan. To test the model, the cell autonomous and non-autonomous pathways through which NF-κB is activated with natural and accelerated aging are dissected using novel mouse models of aging containing the NF-κBeGFP reporter and mutations that prevent NF-κB activation by genotoxic and oxidative stress (NEMODK; cell autonomous) or by inflammatory stress (TNFR−/− and Myd88−/−; non-cell autonomous).

In addition, treatment of the novel NF-κBeGFP reporter mouse models with agents to increase ROS, DNA damage and inflammation is used to dissect the different types of stress in driving NF-κB activation, senescence, DNA damage, stem cell dysfunction and aging. Parabiosis experiments are performed to determine the cell autonomous and non-autonomous activation of NF-κB by genotoxic and oxidative stress and its subsequent contribution to age-related pathology. Primary MEFs from these novel mouse models also are used to dissect the upstream molecular mechanisms of NF-κB activation and downstream effectors that drive senescence, ROS, further DNA damage and aging. Subsequently, the role of NF-κB activation in driving aging through both cell autonomous and non-autonomous mechanisms is examined using the different mouse models, either heterozygous for p65 or, if necessary, treated with the NF-κB inhibitory peptide, and in heterochronic parabiosis experiments. Finally, the NF-κB regulated factors secreted by ERCC1-deficient MEFs and in MDSPCs are identified, which modulate aging both positively and negatively, as well as the factors circulating in $Ercc1^{-/\Delta}$ mice regulated by NF-κB.

These experiments will identify the cell autonomous and non-autonomous pathways important for NF-κB activation and for mediating NF-κB-dependent regulation of senescence, ROS and oxidative DNA damage to drive aging.

p65/NF-κB is Upregulated in ERCC1-Deficient MEFs and Drives Senescence.

To determine whether NF-κB is activated by endogenous genotoxic stress, which arises as a consequence of normal metabolism, $Ercc1^{-/-}$ primary cells and mice were used, which are defective in DNA repair were used. Phosphorylated p65 (p-p65) and IκB were measured in nuclear and cytoplasmic extracts from early passage, congenic $Ercc1^{-/-}$ and WT primary MEFs by immunoblot, and there was a >2-fold increase in nuclear p-p65 in $Ercc1^{-/-}$ MEFs compared to WT, which correlated with an increase in the level of phosphorylated IκB (p-IκB) in the cytoplasm. EMSA was used to confirm increased NF-κB binding in nuclear extracts of $Ercc1^{-/-}$ MEFs, which was abrogated by pretreatment of the samples with an anti-p65 antibody. To determine whether premature senescence of Ercc1 MEFs is NF-κB dependent, the growth of $Ercc1^{-/-}$; $p65^{-/-}$ MEFs was compared to congenic Ercc1−/− MEFs. $Ercc1^{-/-}$ MEFs have reduced proliferation and increased replicative senescence as measured by SA-β-Gal staining, γ-H2AX foci and p16 expression. Genetic depletion of p65 (Ercc1−/−; p65−/−) delayed the onset of senescence, suggesting that p65 is important in mediating senescence in response to genotoxic stress. Furthermore, the $Ercc1^{-/-}$; $p65^{-/-}$ MEFs had reduced ROS compared to $Ercc1^{-/-}$ cells as determined by staining mitochondria with DiOC6 and superoxide anion with Mito-SOX. Finally, the senescence of $Ercc1^{-/-}$ MEFs (>60% of cells SA-β gal+) could be reversed within 24 hours by treating them with the IKKβ inhibitor IKKiVII.

Taken together, these data suggested that endogenous DNA damage, when not repaired, drives cellular senescence via an NF-κB-dependent mechanism. Inhibition of IKK/NF-κB was as or more efficient in reversing senescence of $Ercc1^{-/-}$ MEFs than rapamycin, potent anti-oxidants (XJB, NDGA) and a Nrf2 agonist, bardoxolone methyl. SIRT1 agonists showed no activity in this assay. Interestingly, consistent with previously published reports, senescence of $Ercc1^{-/-}$ MEFs resulted in secretion of factors able to drive senescence of WT MEFs following addition of conditioned media, demonstrating that a paracrine effect contributes to increasing senescence.

Naturally Aged, $Ercc1^{-/-}$ and $Ercc1^{-/\Delta}$ Mice have Increased NF-κB Transcriptional Activity.

To determine whether NF-κB is activated in $Ercc1^{-/-}$ and Ercc1−/Δ mice relative to wild type littermate controls, $Ercc1^{-/-}$ and $Ercc1^{-/\Delta}$ mice were generated carrying an NF-κB-dependent promoter, containing 5 copies of the HIV LTR NF-κB binding site upstream from a minimal promoter, driving eGFP expression transgene 60. The $Ercc1^{-/-}$; NF-κBeGFP were sacrificed at 3 wks of age when they showed extensive age-related pathologies and the tissues were analyzed for eGFP expression by fluorescence microscopy. All tissues from the progeroid mice had a quantitative, significant increase in the number of eGFP+ cells (p<0.05 for liver, kidney, muscle, pancreas; n=6 mice) compared to littermate controls. For example, whereas young animals show NF-κB expression (eGFP+ green cells) only in the Bowman's capsule in the kidney, the $Ercc1^{-/-}$; NF-κBeGFP, $Ercc1^{-/\Delta}$; NF-κBeGFP and naturally aged NF-κBeGFP reporter mice contain more cells with highly active NF-κB within the glomerulus. Analysis of skeletal muscle also showed a dramatic increase in the number of eGFP-expressing muscle fibers in the $Ercc1^{-/-}$; NF-κBeGFP and naturally aged reporter mice compared to controls. An increase in eGFP+ cells with aging was also observed in different cell types, for example, cells from the nucleus pulposus of the intervertebral disc of 24 month old mice, confirmed by RT-PCR for NF-κB regulated genes61, as well as approximately 50% of Gr1+CD11b+ cells in the bone marrow. In addition, NF-κB activation increases substantially between 4-8 weeks in podocytes in the kidney. Overall, these results are consistent with the stochastic model of aging, which predicts that certain susceptible cells randomly acquire damage including DNA damage, resulting in activation of NF-κB.

However, it remains unclear whether a non-cell autonomous mechanism is involved in increasing NF-κB activation in neighboring or distant cells and tissues.

Genetic Depletion of NF-κB Extends Lifespan and Delays Onset of Age-Related Pathology.

To examine the role of NF-κB/p65 in the aging process, $Ercc1^{-/\Delta}$ mice heterozygous for the p65 subunit ($Ercc1^{-/\Delta}$; $p65^{+/-}$) were generated, which have significantly reduced NF-κB activity, and the $Ercc1^{-/\Delta}$ and $Ercc1^{-/\Delta}$ $p65^{+/-}$ littermates were monitored biweekly for the onset of age-related symptoms. The onset of the majority of symptoms characteristic of aging was delayed in $Ercc1^{-/\Delta}$ $p65^{+/-}$ mice, including trembling, frailty, sarcopenia, ataxia, ocular impairment, kyphosis, priapism, and urinary incontinence, all signs of neurodegeneration, as well as kyphosis.

Additionally, the overall physical appearance of the $Ercc1^{-/\Delta}$ p65+/− mice was dramatically improved. In addition to assessing outward signs of aging, histologic analysis was performed. Compared to $Ercc1^{-/\Delta}$ mice, $Ercc1^{-/\Delta}$ $p65^{+/-}$ mice exhibited reduced steatosis, a marker of aged liver. Kidneys from $Ercc1^{-/\Delta}$ mice had increased hyaline casts and glomerulosclerosis, typical of aged kidney, which were reduced in $Ercc1^{-/\Delta}$ $p65^{+/-}$ mice. There also was a marked reduction in glial fibrillary acidic protein (GFAP) staining, a marker of neurodegeneration, in the cerebella of $Ercc1^{-/\Delta}$ $p65^{+/-}$ mice. Finally, osteoporosis was significantly reduced in Ercc1$^{-/\Delta}$ p65$^{+/-}$ mice, due to effects of p65 heterozygosity on both osteoblasts and osteoclasts as was intervertebral disc pathology.

Treatment with the 8K-NBD Peptide Delays Onset of Aging-Like Symptoms and Pathology in Ercc1$^{-/\Delta}$ Mice.

To determine whether pharmacological inhibition of the IKK/NF-κB pathway also delays aging, Ercc1$^{-/\Delta}$ mice were chronically treated with the 8K-NBD peptide (10 mg/kg intraperitoneal, 3× per week) beginning at 5 weeks of age, prior to the onset of aging symptoms. This peptide, derived from an 11 amino acid sequence of IKKβ, specifically blocks the interaction between IKKβ and NEMO, inhibiting IKK activity. Mice treated with 8K-NBD showed a delay in the onset of all symptoms compared to siblings treated with the mutant peptide, with the exception of trembling. There also was a visible difference in the appearance of the mice treated with 8K-NBD compared to their siblings treated with the mutant peptide at 15 and 19 weeks of age. Histologic analysis was performed on tissues of 19 week-old mice to determine whether treatment with 8K-NBD reduced age-related pathology. Similar to the Ercc1$^{-/\Delta}$ p65$^{+/-}$ mice, 8K-NBD treatment resulted in reduced liver steatosis and renal hyaline casts, GFAP staining, bone porosity and loss of islets in mice while restoring proteoglycan synthesis in intervertebral discs back to WT levels.

Collectively, these data demonstrated that pharmacological inhibition of IKK/NF-κB activation, like heterozygosity in p65, leads to attenuation of age-related pathologies.

Chronic i.p. Administration of 8K-NBD Leads to Suppression of NF-κB Activity and Age-Related Transcriptional Changes.

Genome-wide expression profiling of livers from Ercc1$^{-/\Delta}$ mice treated with 8K-NBD vs. mutant sibling mice treated with the control peptide were analyzed using Affymetrix arrays (n=3 pairs). Numerous pathways previously implicated in the aging process were affected including growth hormone/insulin-like growth factor 1 (GH/IGF-1) signaling, DNA repair pathways, and inflammatory pathways. Interestingly, catalase was significantly upregulated by chronic 8K-NBD treatment as were genes regulated by Nrf2 and involved in mitochondrial respiration, suggesting that part of the therapeutic effect could be due to reduced ROS. In addition, of the approximately 300 genes with known NF-κB regulatory elements, 8% showed significant expression differences between the two groups of mice. Expression of 89% (27/30) of these genes was significantly down-regulated in mice treated with NBD, as expected with chronic IKK inhibition.

Taken together, these data strongly suggested that NBD treatment regulates a battery of genes, including those implicated in inflammation and oxidative stress, which can modulate the aging process.

NF-κB Drives DNA Damage and Senescence.

Through the use of liquid chromatography mass spectrometry (LC-MS), it has been demonstrated that oxidative DNA damage (cyclopurine adducts) was increased in the liver and the kidney of Ercc1$^{-/\Delta}$ compared to normal littermates, and increased as the animals aged. The level of damage also increased in WT mice with age. Interestingly, the level of cyclopurines was significantly reduced in p65$^{+/-}$ and Ercc1$^{-/\Delta}$; p65$^{+/-}$ mice and in Ercc1$^{-/\Delta}$ mice chronically treated with 8K-NBD.

These results suggested that NF-κB activity promotes ROS and oxidative damage in both naturally aged and Ercc1$^{-/\Delta}$ mice. Importantly, Ercc1$^{-/\Delta}$; p65$^{+/-}$ mice also had fewer senescent cells compared to Ercc1$^{-/\Delta}$ mice, demonstrating that NF-κB also can drive senescence in vivo.

Reducing NF-κB/p65 Improves Function of MDSPCs.

It has been demonstrated that adult progenitor cells derived from muscle (MDSPCs) of ERCC1-deficient and old WT mice are dysfunctional. Injection of young, but not old, WT MDSCs into ERCC1-deficient mice significantly delayed the onset of age-related pathology and extended lifespan via a paracrine/endocrine mechanism. Interestingly, reducing NF-κB in MDSPCs, either genetically or pharmacologically improved their proliferation and ability to differentiate, suggesting that NF-κB drives aging related loss of stem cell function.

Moreover, IP injection of young p65$^{+/-}$ MDSPCs into a mouse model of muscular dystrophy improved muscle pathology to a much greater extent that WT MDSPCs.

Taken together, these results with MDSPCs suggested that aging can be regulated through a paracrine/endocrine mechanism by young stem cells and that NF-κB plays key role in regulating age-related stem cell function and expression of the therapeutic factor(s).

Determination of Whether Aging-Related NF-κB Activation is Mediated Through a Cell Autonomous and/or Non-Autonomous Mechanism.

Preliminary results indicate that NF-κB is activated in more cells in a variety of tissues in old and progeroid mice compared to young. NF-κB activation was detected in particular cell types, for example, CD11B$^+$Gr1$^+$ cells in the bone marrow and podocytes in the kidney. To determine whether this NF-κB activation is due to a cell autonomous or non-autonomous mechanisms, Ercc1$^{-/\Delta}$ and WT mice containing the NF-κBeGFP reporter are crossed with one of three different strains of mice, defective in different pathways for NF-κB activation. The first strain is deficient in DNA damage induced activation of NF-κB due to a knock-in mutation in NEMO (NEMODK). Arginine mutations in K270 and K302 of NEMO prevent sumoylation in response to DNA damage. NF-κB activation in response to gamma irradiation (IR), but not LPS or TNFα is abrogated in cells from these mice. To address the role of inflammation induced-NF-κB activation, mice deficient in both TNFα receptors (containing targeted deletions in the p55 (Tnfrsf1a) and p75 (Tnfrsf1b) TNFα receptors) or MyD88 are used. These mice are defective for induction of NF-κB by TNFα and IL-1R/TLR, respectively. To confirm that the reporter mice are responding as expected, the NEMODK, TNF-R−/− and MyD88−/− NF-κBeGFP reporter mice (10 weeks of age) is irradiated and the extent of NF-κB activation assessed at 1, 3 and 7 days post-irradiation.

The NEMODK, TNF-R$^{-/-}$ and MyD88$^{-/-}$ Ercc1$^{-/\Delta}$ or WT strains are examined for eGFP-positive cells (3 mice per group) at different time points (every month for Ercc1$^{-/\Delta}$ mice and every 6 months for naturally aged mice) in different tissues (liver, kidney, spleen, brain, muscle, pancreas and bone marrow). The levels of ROS, senescence (liver), oxidative DNA damage (liver and kidney) and onset of age-related pathology are measured in the NEMODK, TNF-R-deficient and IL-1/TLR-signaling deficient mice (5 mice per group). Furthermore, MDSPCs from the muscle of these mice are isolated and analyzed for reduction in number and for defects in proliferation and differentiation compared to young WT MDSPCs.

These experiments will examine which stress pathway(s) is important for driving activation of NF-κB in accelerated and naturally aged mice. To determine whether indeed it is chronic DNA damage that drives NF-κB activation in vivo and whether activation of NF-κB correlates with an increase in ROS, senescence and age related pathologies, the different mouse strains describe above are treated chronically with 8 μg/kg of mechlorethamine (MEC), which increases mono adducts, intra-strand crosslinks and inter-strand crosslinks, once per week for 6 weeks beginning at 8 weeks of age. Treatment of Ercc1-A; p16INK4-luciferase mice with MEC weekly for 6 weeks has been demonstrated to accelerate age-related tissue pathology and senescence in vivo and in MEFs in culture. At 14 and 20 weeks of age, the treated mice are euthanized and tissues collected for analysis of NF-κBeGFP expression compared to untreated animals.

Five mice are used per time point. ROS, senescence, oxidative DNA damage, MDSPC dysfunction, and the age at onset of aging-related pathologies are measured and compared to untreated mice. These experiments will determine whether DNA damage induced by MEC treatment induces NF-κB, cell senescence, ROS and thereby oxidative DNA damage, which would be a completely unprecedented outcome considering that MEC is an alkylating agent.

To examine the role of oxidative stress in driving NF-κB activation, different reporters strains are chronically treated with a mitochondrial-targeted radical scavenger (XJB-5-131; 2 mg/kg i.p. 3× per week to reduce mitochondrial ROS) or with menadione (0.35 mg/g orally per day×30 days to increase mitochondrial ROS). To determine whether localized DNA damage can lead to activation of NF-κB in other, undamaged cells and tissues (consistent with a non cell autonomous mechanism) the NF-κBeGFP transgene are combined tissue specific deletion of Ercc1. ERCC1 is deleted in cells in which significant NF-κB activation was observed (e.g. renal podocytes, CD11B+ cells, myofibers) as well as cells known to be sensitive to loss of Ercc1 (e.g. 1 cells, hepatocytes). Liver, kidney, muscle, pancreas and bone marrow from these mice will be examined for NF-κBeGFP activation at various time points via confocal detection of GFP.

Heterochronic parabiosis has been used to identify systemic factors that regulate tissue homeostasis and lifespan. Similarly, parabiosis is used here to determine if NF-κB activation in one organism can impact tissue homeostasis in a second organism via circulating factors. Ercc1$^{-/\Delta}$ mice are surgically paired with littermate WT NF-κBeGFP at 5-6 weeks of age to determine whether NF-κB activation in response to genotoxic stress activates NF-κB and tissue pathology in trans. Similarly, aged WT mice (24 months) are paired with young WT NF-κBeGFP mice (3 months). Conversely, young WT animals are paired with old WT NF-κBeGFP mice (5 sets of mice per group) to determine if factors secreted by young mice attenuate aging-related NF-κB activation.

The extent of NF-κB activation in each tissue is examined following 1, 2 and 3 months of parabiosis by identification of NF-κBeGFP$^+$ cells. Similarly, the extent of senescence, ROS and oxidative DNA damage in liver and kidney in each of the paired mice is measured. In order to correlate NF-κB activation with age, the onset of age-related pathologies is also monitored and the extent of age-related histological changes in liver, kidney, pancreas, bone, muscle, bone marrow and brain is determined in each set of paired animals. The NEMODK, TNF-R–/– and MyD88–/– NF-κBeGFP reporter mice also can be used in the heterochronic parabiosis experiments.

Examination of the Cell Autonomous and Non-Autonomous Roles of NF-κB in Driving Cell Senescence, ROS Production and DNA Damage In Vitro.

Preliminary results indicate that NF-κB plays a key role in regulating cellular senescence and ROS, especially under conditions of cellular stress. The types of cellular stress (genotoxic, oxidative and inflammatory) observed as activating NF-κB in vivo are characterized further in cell culture. Also, the subsequent role of NF-κB in driving senescence, ROS and further DNA damage through cell autonomous and/or non-autonomous mechanisms is characterized. For all the MEF experiments described below, each time point and treatment is done in triplicate using three independent cell lines of each genotype. Primary MEFs from WT, Ercc1$^{-/-}$ and Ercc1$^{-/-}$; p65$^{-/-}$ mice are passaged at 3% and 20% oxygen, the latter of which induces senescence. The MEFs are transduced at p2 with a lentiviral vector expressing a luciferase-eGFP fusion protein driven from an NF-κB dependent promoter. The extent of NF-κB activation at each subsequent passage is measured by luciferase analysis of cell extracts. Concurrently, the extent of senescence is measured at each passage by measuring cell number (rate of proliferation), SA-β-gal activity, γ-H2AX foci and by p16 expression. This will reveal if NF-κB activation precedes the onset of senescence. To interrogate a cell-autonomous mechanism, populations of NFκB-eGFP positive and negative cells are isolated by flow cytometry and stained for proteins that can discriminate senescent cells (γ-H2AX, SA-β gal and Ki67). To further confirm the role of IKK/NF-κB in maintaining senescence, late passage cells will be treated with an IKK inhibitor and NF-κB activity and senescence measured at 3, 12 and 24 hours post-treatment.

To determine whether NF-κB activation is driving ROS production, the levels of intra-cellular ROS are measured in GFP+ cells using multiple assays at each passage. Whether there is a significant co-localization of NF-κB activation (eGFP+), cell senescence (γH2AX or SA-βgal) and ROS is also measured. In addition ROS is measured in Ercc1$^{-/-}$ and Ercc1$^{-/-}$; p65$^{-/-}$ MEFs. To examine the role of oxidative stress in driving NF-κB activation and senescence, primary MEFs from WT, Ercc1$^{-/-}$ and Ercc1$^{-/-}$; p65$^{-/-}$ mice, transduced with the lentiviral vector carrying a NF-κB-activated luciferase eGFP fusion protein, are treated with XJB-5-131 or menadione to decrease or increase mitochondrial superoxide anion, respectively and NF-κB activation, senescence and ROS measured.

It has been demonstrated that treatment of ERCC1-deficient MEFs with the genotoxin MEC induces cellular senescence in vitro. To determine whether treatment with MEC induces NF-κB dependent senescence, passage 3, 4, and 5 WT, Ercc1–/– and Ercc1–/–p65–/– MEFs are treated with MEC for 24 hours and the extent of NF-κB activation, cell senescence, ROS production and oxidative DNA damage measured.

If the hypothesis is correct, DNA damage induced by MEC (monoadducts, intra-strand crosslinks and inter-strand crosslinks) will induce NF-κB, cell senescence and ROS and thereby increase oxidative DNA damage, demonstrating a feedback loop.

To examine further the role of NEMO sumoylation in driving NF-κB activation and cell senescence, MEFs are isolated from WT and ERCC1-deficient NF-κBeGFP reporter strains homozygous for the NEMODK mutation. NF-κB activation, cellular proliferation and expression of senescence markers will be measured at each passage at 20% O2. If this hypothesis is correct, MEFs containing NEMODK will have reduced NF-κB activation, ROS levels, replicative senescence and oxidative DNA damage compared to controls. To determine whether NF-κB activation has cell non-autonomous effects, MEFs from WT and Ercc1$^{-/-}$; NF-κB-eGFP reporter strains deficient for TNF-R or MyD88 are used.

If inflammatory factors secreted from the senescent cells play a role in driving further activation of NF-κB, eGFP signal, ROS, senescence, and even DNA damage should be reduced in cells defective in TNF-R or IL-1R/TLR signaling.

Since supernatants from senescent Ercc1$^{-/-}$ MEFs, like IR-induced senescence, can drive senescence of WT MEFs, the effect of supernatants from senescent Ercc1$^{-/-}$ MEFs on NF-κB activation, ROS production, cell senescence and oxidative DNA damage is examined. In order to examine the ability of NF-κB, in the absence of initiating DNA damage, to drive senescence, ROS and then DNA damage cell autonomously, WT, p65$^{-/-}$, Ercc1$^{-/-}$ and Ercc1$^{-/-}$; p65$^{-/-}$ MEFs are treated with low doses (5-50 ng) of IL-1β and/or IL-1α chronically (every 2 days) starting at passage 3 (3% O2) and the extent of NF-κB activation, senescence, ROS and oxidative DNA damage measured at each subsequent passage. MEFs deficient in MyD88 are used as a negative control. Here, it is anticipated that treatment with IL-1β or IL-1α will result in NF-κB activation, which, in turn, will lead to an increase in ROS and senescence with subsequent DNA damage that is higher in Ercc1$-/-$ MEFs compared to WT.

This analysis will confirm the presence of a feedback loop and will identify a role for inflammatory stress in inducing senescence, ROS and/or oxidative DNA damage.

Determination of Whether NF-κB Mediates Cellular Senescence, ROS Production, DNA Damage and Aging-Related Degenerative Diseases Via a Cell Autonomous or Non-Autonomous Mechanism In Vivo.

The in vivo experiments will determine what cell autonomous and non-autonomous pathways are important for driving NF-κB activation with aging. The role of activated NF-κB in driving age-related pathology through cell autonomous and non-autonomous pathways in response to different stimuli is assessed using similar mouse models as utilized, but heterozygous for p65. In addition, p65 heterozygosity in the same tissues as ERCC1 is deleted in, are generated using a floxed p65 allele. Initially, to examine the role of NF-κB in inducing age related pathology as well as senescence, ROS and oxidative DNA damage in response to increased DNA damage NF increase the magnitude of the observed effect(s), Ercc1$^{-/\Delta}$; p65$^{+/-}$ and Ercc1$^{-/\Delta}$ mice are injected with 8 µg/kg of MEC, once per week for 6 weeks starting at 8 weeks of age and the onset of age related pathologies monitored as well as analysis of tissue histology and levels of ROS, senescence and oxidative DNA damage performed at 14 and 20 weeks. To examine the effect of oxidative stress induced NF-κB on driving aging, Ercc1$^{-/\Delta}$; p65$^{+/-}$ and Ercc1$^{-/\Delta}$ are treated with menadione (0.35 mg/g orally per day×30 days to increase mitochondrial ROS) starting at 8 weeks of age and the extent of NF-κB activation, ROS, senescence and DNA damage measured at 14 and 20 weeks.

To examine the effect of non-genotoxic stress induced NF-κB on driving aging, Ercc1$^{-/\Delta;\,p}$65$^{+/-}$ and Ercc1$^{-/\Delta}$ mice are injected IP with 100 ng of IL-1β and/or IL-1α every three days starting at 8 weeks of age and the extent of NF-κB activation, ROS, senescence and DNA damage measured at 14 and 20 weeks. To determine whether reducing NF-κB results in expression of soluble factors able to regulate age-related degeneration, DNA damage, senescence and/or ROS, parabiosis experiments are performed where Ercc1$^{-/\Delta}$; p65$^{+/-}$ mice are paired parabiotically with Ercc1$^{-/\Delta}$, starting at 1 month, and the timing of onset of age related pathology determined. Similarly, tissues from both mice are analyzed every two months for the extent of senescence, ROS and DNA damage compared to paired Ercc1$^{-/\Delta}$ and Ercc1$^{-/\Delta}$; p65$^{+/-}$ mice.

As additional controls, Ercc1$^{-/\Delta}$ mice carrying mutations in NEMO (NEMODK), Myd88 or both TNF receptors can be used. Also, if needed, the Ercc1$-/\Delta$ or Ercc1$-/\Delta$; p65$+/-$ mice can be pre-treated with MEC, menadione or IL-1 prior to parabiotic pairing to enhance specific effects.

The results suggest that young, but not old MDSPCs secrete or release soluble factors able to improve lifespan and healthspan. In addition, preliminary results also suggest that p65$^{+/-}$ MDSPCs have improved function over WT MDSPCs. Thus, the ability of MDSPCs derived from p65 heterozygous WT and Ercc1$^{-/\Delta}$ mice to extent lifespan and healthspan of Ercc1$^{-/-}$ and Ercc1$^{-/\Delta}$ mice respectively will be evaluated. For these experiments, 106 of the different MDSPC populations are injected IP and effects on lifespan and healthspan as well as ROS, senescence and DNA damage are examined, as previously reported. Preliminary results suggest that tissue or cell type specific deletion of ERCC1 results in adverse effects in not only the ERCC1-deficient cells, but also in other cells within the microenvironment and possibly systemically.

Thus, the role of NF-κB in conferring the cell autonomous and/or non-autonomous effects observed is evaluated by simultaneously inactivating ERCC1 and one allele of p65 in the same cell type or tissue. For these experiments, mice carrying null and floxed alleles of ERCC1 and one floxed allele of p65 are generated. The pathologies of the tissue specific ERCC1 KO mice are compared to pathologies in the combined tissue specific ERCC1 and p65$^{+/-}$ KO.

Proteomics Used to Identify Proteins Secreted by Primary Differentiated and Stem Cells in which NF-κB is Activated and in the Serum of Mice in which NF-κB Activation is Increased Due to Stress or Aging.

The goal of these experiments is to identify the factor(s) regulated by NF-κB, which are able to confer negative and positive effects on aging. In particular, the factors secreted by ERCC1-deficient MEFs in which NF-κB is activated, able to drive ROS production and cell senescence and/or secreted by MDSPCs genetically depleted of NF-κB that are able to improve tissue homeostasis, are identified by proteomic analysis of the secretomes. Moreover, based on results from the MEF analysis, the factors circulating in the serum of Ercc1$^{-/\Delta}$ or Ercc1$^{-/\Delta}$; p65$^{+/-}$ mice that drive and inhibit aging, respectively, are identified.

Serum from Ercc1$^{-/\Delta}$ and Ercc1$^{-/\Delta}$; p65$^{+/-}$ mice are compared. The un-biased analysis of all ions detected by high resolution Fourier transform mass spectrometry, not just ions that have corresponding MS/MS spectra and peptide sequences, is a powerful approach for discovering biologically relevant peptides and proteins. An important advantage of the dMS approach is that it is not limited to the analysis of tryptic peptides and has been successfully applied to the identification of intact plasma peptides and proteins. To enable the detection of molecules present at low abundance, a variety of classical biochemical sample preparation methods (e.g. ultrafiltration, strong cation exchange chromatography, immuno-depletion, etc.) are used to fractionate the secretome of the different MEF and MDSPC populations.

The fractions are tested for biological activity by their ability to induce senescence of MEFs or for rescue of aged MDSPCs prior to mass spectrometry analysis. Those secreted or released factors identified as regulated by NF-κB in Ercc1$^{-/-}$ MEFs and MDSPCs are validated using either lentiviral gene transfer of shRNA, to reduce expression, or cDNAs, to increase expression, and the effects on MEF and MDSPCs determined.

In particular, the ability of the conditioned media from genetically modified MEFs to induce senescence of WT MEFs is assessed. In addition, the ability of genetically modified MDSPCs to rescue aged MDSPCs and subsequently the ability to extend healthspan and lifespan in ERCC1-deficient mice following IP injection is determined.

Factors present specifically in the serum of Ercc1$^{-/\Delta}$ compared to Ercc1$^{-/\Delta}$; p65$^{+/-}$, representing possible biomarkers of aging, is examined in the serum of naturally aged mice.

These experiments will serve to identify the factors that drive or inhibit aging that are regulated by NF-κB. If successful, the proposed experiments could lead to novel therapeutics for treating age-related degenerative diseases and/or biomarkers of aging.

Example 12

In this study, the role of mTOR in the multilineage differentiation, apoptosis, and senescence of MDSPCs isolated from a murine model of progeria was examined. MDSPCs were isolated from the Ercc1$^{-/\Delta}$ murine model of accelerated aging. These mice exhibited increased mTOR expression and exhibited a reduction in autophagy. Inhibiting mTOR in this adult stem cell population improved their myogenic and chondrogenic capacities, and reduced the adipogenic differentiation capacity of the progeroid MDSPCs.

The purpose of this study was to determine if mTOR signaling plays a role in stem cell dysfunction as it relates to aging. Exposing progeroid MDSPCs to rapamycin promoted multilineage differentiation while attenuating apoptosis and cellular senescence, therefore demonstrating that inhibition of mTOR rescues the defect in Ercc1$^{-/\Delta}$ MDSPCs and could represent a target to delay aging.

Material and Methods

Rapamycin Treatment

Rapamycin was obtained from LC Laboratories (Woburn, Mass., USA), dissolved in dimethyl sulphoxide (DMSO) at 50 mg/ml, and stored at −20° C. MDSPCs from Ercc1$^{-/\Delta}$ and WT mice were treated with 10 nM rapamycin in order to inhibit mTOR. As a control, the same amount of DMSO was used to treat MDSPCs from these two populations.

Myogenic Differentiation Assay

MDSPCs were plated in the afternoon at a density of 1,000 cells/cm$^2$ and cultured for 3 days. The cells were then placed in DMEM supplemented with 2% FBS for an additional 4 days to induce myogenic differentiation, with or without 10 nM rapamycin. On day 7, immunostaining was performed to reveal fast myosin heavy chain expression (f-MyHC), a marker of terminal myogenic differentiation. Cold methanol-fixed cultures were blocked with 5% goat serum and incubated with f-MyHC mouse monoclonal antibody (1:250; SIGMA-ALDRICH®), secondary biotinylated IgG (1:250; Vector Laboratories) for one hour, and streptavidin-594 (1:500; SIGMA-ALDRICH®) for 15 minutes to fluorescently label the myotubes. Nuclei were counter stained with 4', 6' diamidino-2-phyenylindole (DAPI, 100 ng/ml; SIGMA-ALDRICH®) for 10 minutes. The presence of fluorescein was visualized using a Leica DMIRB microscope equipped with a Retiga digital camera and evaluated using Northern Eclipse software (v. 6.0; Empix Imaging). Myogenic differentiation was calculated as the percent of cells expressing f-MyHC. Data from three replica plates for four independent experiments were analyzed. Total RNA was also extracted as described below for quantitative RT-PCR analysis. Expression of myogenic genes MyHC and Desmin were analyzed.

Chondrogenic Differentiation Assay

To assess chondrogenic differentiation, micromass cultures were established as described previously (see Ahrens et al., 1977, *Dev Biol*, 60:69-82; San Antonio et al., 1987, *Dev Biol*, 123:17-24; and Kishimoto et al., 2009, *Cell Biol Int*, 33:1222-1229). A 10 µl suspension containing 1×10$^5$ cells was placed at the center of a well of a 12-well tissue culture dish. The cells were allowed to adhere for 60 min before the wells were filled with 1 ml of chondrogenic medium (Lonza) supplemented with 10 ng/ml transforming growth factor β3 (TGF-β3; R&D System) with or without 10 nM of rapamycin. The medium was changed every three days for six days. Cultured micromass pellets were fixed with 10% neutral buffered formalin containing 0.1% acetylpyridinium chloride and stained with 1% Alcian blue (pH 1.0) for 30 min to stain the highly sulfated proteoglycans that are characteristic of cartilaginous matrices. For quantification, alcian blue stain was solubilized in 4M guanidine HCl, 50 mM Tris-HCl (pH 7.4), 0.1% CHAPS and the pellet's absorbance was measured at a wavelength of 595 nm as previously described (see Kishimoto et al., 2009, *Cell Biol Int*, 33:1222-1229). Data from three replica plates for four independent experiments were analyzed. Total RNA was extracted for quantitative real-time PCR (RT-PCR) analysis. Expression of the chondrogenic genes, collagen type 2A1 (Col2A1) and aggrecan were analyzed.

Adipogenic Differentiation Assay

MDSPCs were seeded on 12 well plates at a concentration of 1×10$^5$ cells per well. After the cells had reached confluence, adipogenic differentiation was induced by exposure to three cycles of standard induction/maintenance media with or without 10 nM rapamycin. This consisted of culturing the cells for 72 hours in adipogenic induction media containing dexamethasone, 3-isobutyl-1-methyl-xanthine (IBMX), recombinant human insulin and indomethacin, followed by 48 hours of culture in maintenance media (LONZA). Adipogenesis was assessed using ADIPORED™ (Lonza), a marker of accumulation of intracellular triglycerides. Cells were stained with ADIPORED™ for 10 min according to the manufacturer's instructions and visualized using fluorescence microscopy. Nuclei were stained with DAPI. For quantification, after 10 min of incubation the plate was placed in the spectrophotometer (INFINITE® M200, Tecan, Switzerland), and the fluorescence was measured using an excitation wavelength of 485 nm and emission detection wavelength at 572 nm. Data from three replica plates for four independent experiments were analyzed. Total RNA was extracted for quantitative RT-PCR analysis. Expression of adipogenic genes Peroxisomes proliferator-activated receptor gamma (PPAR ) and Lipoprotein lipase (LPL) was analyzed.

Apoptosis Assay

Apoptotic cell death was evaluated in cultured cells using the In Situ Cell Death Detection kit containing fluorescein (Roche Applied Science) for TUNEL detection according to the manufacturer's protocol. To visualize the nuclei, the cultures were incubated with DAPI for 10 min. The presence of fluorescein as a cell death marker was visualized using a Leica DMIRB microscope. The number of cells that were TUNEL-positive was calculated and averaged across 15 fields each from three replica plates for four independent experiments. The percent of apoptotic cells was calculated as TUNEL-positive cells divided by the total number of cells, and then multiplied by 100.

Cellular Senescence Assay

Cellular senescence was evaluated in cultured cells using the Senescence β-Galactosidase Staining Kit (Cell Signaling Technology) for SA-β-gal activity according to the manufacturer's protocol. Images were captured using a LEICA® DMIRB microscope. The number of cells that were SA-β- gal-positive was calculated and averaged across 15 fields each from three replica plates for four independent experiments. The percent of senescent cells was calculated as SA-β-gal-positive cells divided by the total number of cells and then multiplied by 100.

SDS-PAGE and Immunoblotting

Cells were lysed in Laemmli Sample Buffer (Bio-Rad), boiled for 5 min, and centrifuged at 4,000 r.p.m. for 5 min. The samples were loaded on a 4-12% SDS-polyacrylamide gel, transferred to an Immobilon PVDF transfer membrane (Millipore, Inc.) and probed with primary antibodies followed by HRP-conjugated secondary antibody. Proteins were visualized with ECL Plus reagent (Amersham Biosciences), and the chemical luminescent reaction visualized using a FOTO/Analyst Luminary/Fx CCD imaging system (Fotodyne Inc.). The following antibodies were used in this study: rabbit anti-Poly (ADP-ribose) polymerase (PARP), rabbit anti-P16, rabbit anti-P21, rabbit anti-LC3, rabbit anti-mTOR, rabbit anti-phospho-mTOR (p-mTOR), rabbit anti-phospho-4E-BP1 (p-4E-BP1) (Thr37/46), rabbit anti-phospho-p70 S6 (p-p70 S6) kinase (Thr389), rabbit anti-GAPDH, HRP-conjugated goat anti-rabbit IgG, and HRP-conjugated goat anti-mouse IgG (all antibodies are from Cell Signaling Technology). The intensities of the bands were quantified using image analysis software, ImageJ version (NIH Image). Values were normalized relative to GAPDH expressions.

RNA Isolation and Quantitative RT-PCR

Total RNA was extracted with QIAshredder homogenizers and the RNEASY® Mini kit (QIAGEN®) according to the manufacturer's protocol. One microgram of total RNA was used for random hexamer-primed cDNA synthesis using a SUPERSCRIPT™ II pre-amplification system (INVITROGEN®). Quantitative RT-PCR reactions were performed in triplicate using iQ5 (BIO-RAD®) and Maxima SYBR Green/ROX qPCR Master Mix (THERMO®) and 300 nM of each of the primers. The primers were designed based on the sequences in the GenBank database. The primer pairs used for this study are shown in Table 6. 2.5% agarose gel electrophoresis was performed to ensure accurate outcomes of the reactions.

Statistical Analysis

The data were expressed as a mean±standard deviation (SD). For multiple comparisons, the one-way ANOVA or the Kruskal-Wallis tests were applied. Pair-wise multiple comparisons were performed using the Tukey-Kramer or Scheffe's post-hoc test. Data analyses were performed using PASW® Statistics 21 (SPSS, Chicago, Ill.). Statistical significance was accepted at $p<0.05$.

Results mTOR Signaling is Elevated in MDSPCs Isolated from Progeroid $Ercc1^{-/\Delta}$ Mice Inhibition of mTOR signaling contributes to the aging-related dysfunction seen in MDSPCs isolated from progeroid $Ercc1^{-/\Delta}$ mice, as shown by the phosphorylation of downstream signaling components of the mTOR pathway (see FIG. 21A). The expression of p-mTOR, p-4E-BP1, and p-p70 S6 kinase in $Ercc1^{-/\Delta}$ MDSPCs was enhanced compared with WT MDSPCs (p-mTOR: $p<0.001$, p-4E-BP1: $p<0.001$, p-p7-S6: $p<0.001$, respectively). Rapamycin treatment of the $Ercc1^{-/\Delta}$ MDSPCs significantly decreased the expression of p-mTOR and p-p70-S6 kinase in $Ercc1^{-/\Delta}$ MDSPCs (p-mTOR: $p<0.001$, p-p7-S6: $p<0.001$, respectively). However, p-4E-BP1 was not significantly reduced by rapamycin treatment ($p=0.506$) (see FIG. 21B). Of note, rapamycin had little, if any, effect on baseline activity of mTOR in WT MDSPCs.

Rapamycin Increased Autophagy in MDSPCs Isolated from Progeroid $Ercc1^{-/\Delta}$ Mice A decline in autophagy, which is regulated by mTOR, contributes to aging (see Cavallini et al., 2007, Autophagy, 3:26-27; Hands et al., 2009, Aging, 1:586-597; Morselli et al., 2009, Aging, 1:961-970; and Ravikumar et al., 2004, Nat Genet, 36:585-595). LC3 expression was measured, which correlates with autophagic activity (see Mizushima et al., 2007, Autophagy, 3:542-545). Immunoblotting analysis revealed that the amount of LC3-II was significantly decreased in $Ercc1^{-/\Delta}$ MDSPCs compared to WT MDSPCs ($p<0.001$) (see FIG. 21C, FIG. 21D). Treatment with rapamycin significantly increased the amount of LC3-II in the $Ercc1^{-/\Delta}$ MDSPC population ($p<0.001$) (see FIG. 21D).

TABLE 6

Primer sequences and product size for RT-PCR

| Gene | | 5' DNA sequence 3' | Amplicon length (bp) |
|---|---|---|---|
| Collagen type II | Forward | 5'-TTGCGTCTACCCCAACCCAG-3' (SEQ ID NO: 17) | 103 |
| | Reverse | 5'-GCCACCGTTCATGGTCTCTC-3' (SEQ ID NO: 18) | |
| Aggrecan | Forward | 5'-GTTGCAGACCAGGAGCAATG-3' (SEQ ID NO: 19) | 79 |
| | Reverse | 5'-TCTCTCGGTCATGAAAGTGGC-3' (SEQ ID NO: 20) | |
| MyHC | Forward | 5'-CCAGGCTGCGGAGGCAATCA-3' (SEQ ID NO: 21) | 115 |
| | Reverse | 5'-GGCCAGCTGCTCTTTCAGGTCG-3' (SEQ ID NO: 22) | |
| Desmin | Forward | 5'-TTCCCTCGAGCAGGCTTCGG-3' (SEQ ID NO: 23) | 147 |
| | Reverse | 5'-GCCATAGGATGGCGCTCGGG-3' (SEQ ID NO: 24) | |
| PPARg | Forward | 5'-ACCGCAAAGAGCACGAGAAG-3' (SEQ ID NO: 25) | 98 |
| | Reverse | 5'-ACCAACGTAAATCACACGGC-3' (SEQ ID NO: 26) | |
| LPL | Forward | 5'-ACTGAGGATGGCAAGCAACA-3' (SEQ ID NO: 27) | 105 |
| | Reverse | 5'-ATTTGTGGAAACCTCGGGCA-3' (SEQ ID NO: 28) | |
| GAPDH | Forward | 5'-CCGTCGTGGATCTGACGTG-3' (SEQ ID NO: 29) | 146 |
| | Reverse | 5'-GTTGCTGTTGAAGTCGCAGG-3' (SEQ ID NO: 30) | |

Rapamycin Restored the Myogenic Differentiation of Progeroid MDSPCs

To determine whether the myogenic differentiation capacity of the progeroid Ercc1$^{-/\Delta}$ MDSPCs was affected by mTOR signaling, the cells were cultured to confluence and then switched to differentiation medium. In the presence or absence of rapamycin, the WT MDSPCs fused to form multinucleated myotubes expressing f-MyHC, a marker of terminal myogenic differentiation (see FIG. 22A and FIG. 22B). In contrast, MDSPCs isolated from the progeroid Ercc1$^{-/\Delta}$ mice formed significantly fewer and smaller myotubes indicating impaired differentiation (p<0.001) (see FIG. 22B). Interestingly, rapamycin significantly improved the myogenic differentiation capacity of the Ercc1$^{-/\Delta}$ MDSPCs (p<0.001) (see FIG. 22A and FIG. 22B). Impaired differentiation of Ercc1$^{-/\Delta}$ MDSPCs was confirmed by measuring the expression of myogenic differentiation markers myosin heavy chain (MyHC) and desmin. The expression of MyHC and desmin in the MDSPCs isolated from the progeroid mice was significantly reduced compared with WT MDSPCs (MyHC: p<0.001, desmin: p<0.001, respectively). The expression of both proteins was up-regulated with rapamycin treatment (MyHC: p<0.001, desmin: p=0.00$^2$, respectively) (see FIG. 22C and FIG. 22D).

Figure 23A:
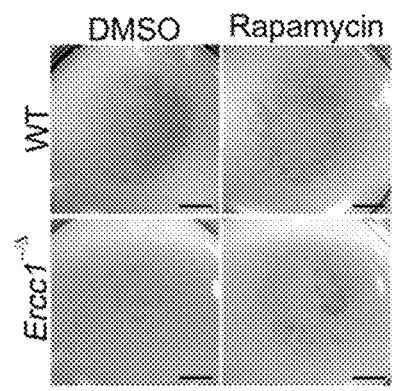
FIGS. 23A-23D depicts the measurement of the effect of rapamycin on chondrogenic differentiation of MDSPCs isolated from progeroid Ercc1$^{-/\Delta}$ mice.
Figure 23B:
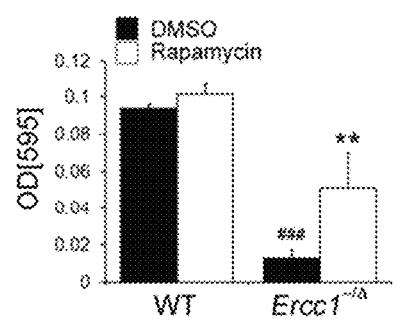
Figure 23C:
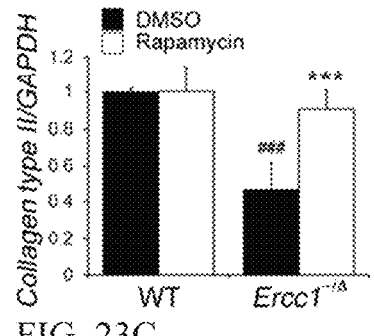
Figure 23D:
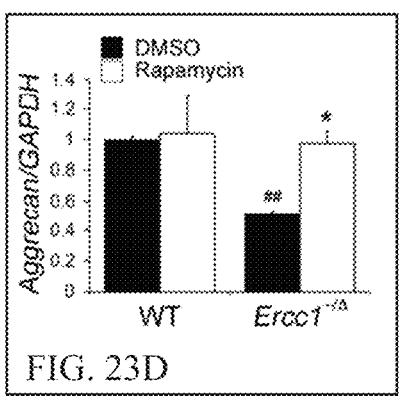

Rapamycin Improves the Chondrogenic Differentiation of Ercc1$^{-/\Delta}$ MDSPCs MDSPC micromass cultures (chondrogenic activity assay) were treated with or without rapamycin and maintained for six days prior to alcian blue staining to detect chondrocytes. Compared with the WT MDSPCs, the progeroid MDSPCs exhibited a marked reduction in chondrogenic differentiation (p<0.001). The chondrogenic differentiation of the progeroid MDSPCs was attenuated with rapamycin treatment (p=0.002) (see FIG. 23A and FIG. 23B). The differentiation defect and the improvement by rapamycin treatment were confirmed by measuring the expression level of two chondrogenic markers, Collagen Type II (Col2a1) and aggrecan. The expression of Col2A1 and aggrecan in MDSPCs isolated from the progeroid mice was significantly reduced compared with the WT MDSPCs (Col2A1II: p<0.001, aggrecan: p=0.002, respectively), and the expression of both Col2A1 and aggrecan was up-regulated with rapamycin treatment (Col2A1: p<0.001, aggrecan: p=0.028, respectively) (see FIG. 23C and FIG. 23D).

Rapamycin Reduces the Adipogenic Differentiation of Ercc1$^{-/\Delta}$ MDSPCs

Figure 24A:
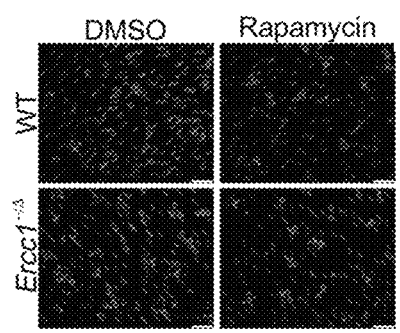
FIGS. 24A-24D depicts the measurement of the effect of rapamycin on adipogenic differentiation of MDSPCs isolated from progeroid Ercc1$^{-/\Delta}$ mice.
Figure 24B:
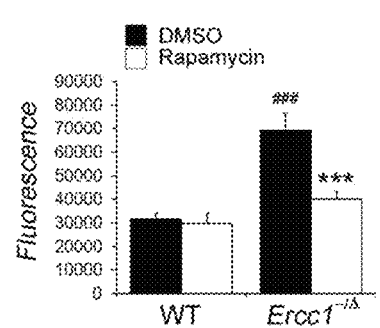
Figure 24C:
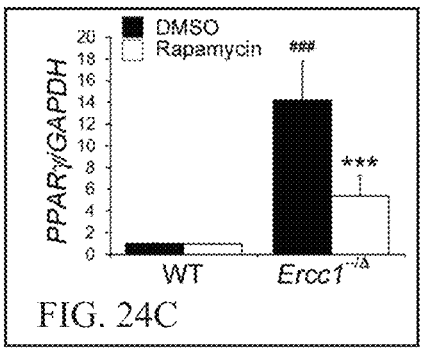
Figure 24D:
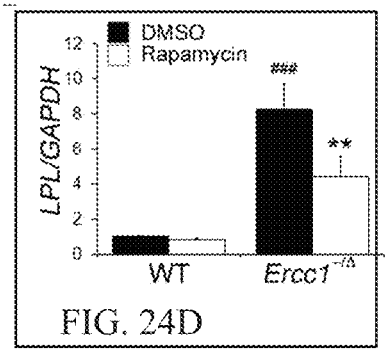

MDSPCs were cultured in adipogenic medium, with or without rapamycin, for 15 days and then stained using AdipoRed (adipogenic marker). The capacity for adipogenic differentiation was higher in the progeroid Ercc1$^{-/\Delta}$ MDSPCs compared to the WT MDSPCs (p<0.001). In addition, adipogenic differentiation in the progeroid MDSPCs was attenuated with rapamycin treatment (p<0.001) (see FIG. 24A and FIG. 24B). PPARγ and LPL (Lipoprotein lipase) mRNA expression (adipogenic markers) was assessed by real-time RT-PCR. Similarly, the expression of PPARγ and LPL was significantly increased in the progeroid MDPSCs compared to the WT MDSPCs (PPARγp<0.001, LPL: p<0.001, respectively). Interestingly, Ercc1$^{-/\Delta}$ MDSPCs treated with rapamycin showed a reduced level of PPARγ and LPL expression (PPARγp<0.001, LPL: p=0.001, respectively) (see FIG. 24C and FIG. 24D).

Rapamycin decreases apoptosis in progeroid MDSPCs

Some adult stem cell populations are dramatically affected by stress, leading to increased apoptosis (see Rossi et al., 2007, Nature, 447:725-729). The level of apoptosis in MDSPCs was determined using the TUNEL assay. The percent of TUNEL positive cells in the Ercc1$^{-/\Delta}$ MDSPCs was significantly higher than in the WT MDSPCs (p<0.001). Rapamycin effectively reduced the percent of TUNEL positive cells in Ercc1$^{-/\Delta}$ MDSPCs (p<0.001) (see FIG. 25A and FIG. 25B). Furthermore, increased expressions of cleaved PARP (apoptosis marker) were detected in progeroid Ercc1$^{-/\Delta}$ MDSPCs relative to WT MDSPCs, and rapamycin served to attenuate the expression of these markers in the MDSPCs (see FIG. 25C).

Rapamycin Decreases the Premature Senescence of Progeroid MDSPCs

Figures 26A, 26B:
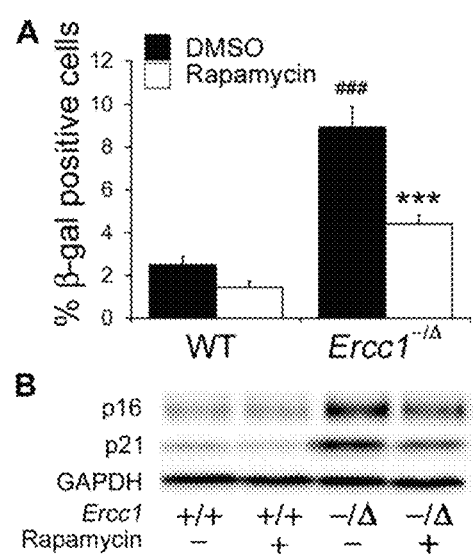
FIGS. 26A-26B depicts the measurement of the effect of rapamycin on senescence in MDSPCs isolated from progeroid Ercc1$^{-/\Delta}$ mice.

Cellular senescence is characterized by cell cycle arrest, which leads to an irreversible loss of differentiation capacity (see Roobrouck et al., 2008, Exp Cell Res, 314:1937-1944). To determine the extent of senescence in MDSPCs isolated from Ercc1$^{-/\Delta}$ mice, senescence-associated beta-galactosidase (SA-β-gal) activity was measured. The percent of SA-β-gal-positive cells in the Ercc1$^{-/\Delta}$ MDSPCs was significantly increased compared to the WT MDSPCs (p<0.001) (see FIG. 26A). However, rapamycin treatment notably reduced the percentage of SA-β-gal-positive cells in the Ercc1$^{-/\Delta}$ MDSPCs (p<0.001) (see FIG. 26A). Moreover, increased expression of p16 and p21 were detected in the progeroid Ercc1$^{-/\Delta}$ MDSPCs compared to the WT MDSPCs, and rapamycin treatment decreased the expression of these senescence markers in the MDSPCs (see FIG. 26B).

These results demonstrated that inhibiting mTOR (e.g., decreasing mTOR activity) using rapamycin improved the myogenic and chondrogenic differentiation potentials of progeroid Ercc1$^{-/\Delta}$ MDSPCs and reduced their adipogenic differentiation capacity by decreasing the percentage of cells undergoing apoptosis, attenuating the rate of senescence, and promoting autophagy. These results provide novel insights into the spontaneous and premature onset of aging-related changes associated with progeria and the role that mTOR has on the accelerated aging of adult stem cells and distinguish important mechanisms through which mTOR impacts the aging process.

OTHER EMBODIMENTS

While the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. An in vitro method of ameliorating a dysfunction of muscle-derived stem/progenitor cells (MDSPCs) isolated from an aged subject, comprising
contacting the MDSPCs with an exogenous amount of isolated young allogeneic muscle-derived stem/progenitor cells (MDSPCs) and one or more inhibitors of mechanistic target of rapamycin (mTOR) and/or inhibitor of kappa B kinase/nuclear factor kappa-light-chain-enhancer of activated B cells (IKK/NF-κB) pathway, thereby ameliorating the dysfunction of the MDSPCs isolated from an aged subject.

2. The method of claim 1, wherein the inhibitor of IKK/NF-κB pathway is a Nemo Binding Domain (8K-NBD) peptide.

3. The method of claim 1, wherein the inhibitor of mTOR is rapamycin.

4. The method of claim 1, wherein said isolated young allogeneic MDSPCs secrete or release regulatory factors selected from recombination signal binding protein for immunoglobulin kappa J region (RBP-JK) inhibitory factor, Stanniocalcin-1, Wingless-Type MMTV Integration Site Family, Member 3A (Wnt3a), KLOTHO, C-C motif chemokine (CCL11), micro-RNA (miRNA)-489, vascular endothelial growth factor (VEGF), and hepatocyte growth factor (HGF), insulin-like growth factor (IGF), and human epidermal growth factor receptor 2 (Her2/neu).

5. The method of claim 1, wherein said isolated young allogeneic MDSPCs restore the myogenic differentiation capacity of the MDSPCs isolated from an aged subject.

6. An in vitro method of restoring the myogenic differentiation capacity of muscle-derived stem/progenitor cells (MDSPCs) isolated from an aged subject, comprising contacting the MDSPCs with an exogenous amount of isolated young allogeneic MDSPCs and one or more inhibitors of mTOR and/or IKK/NF-κB pathway, thereby restoring the myogenic differentiation capacity of the MDSPCs isolated from an aged subject.

7. The method of claim 6, wherein the inhibitor of IKK/NF-κB pathway is a Nemo Binding domain (8K-NBD) peptide.

8. The method of claim 6, wherein the inhibitor of mTOR is rapamycin.

9. The method of claim 6, wherein said isolated young allogeneic MDSPCs secrete or release regulatory factors selected from recombination signal binding protein for immunoglobulin kappa J region (RBP-JK) inhibitory factor, Stanniocalcin-1, Wingless-Type MMTV Integration Site Family, Member 3A (Wnt3a), KLOTHO, C-C motif chemokine (CCL11), micro-RNA (miRNA)-489, vascular endothelial growth factor (VEGF), and hepatocyte growth factor (HGF), insulin-like growth factor (IGF), and human epidermal growth factor receptor 2 (Her2/neu).

\* \* \* \* \*

SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Synthesized primer

```
<400> SEQUENCE: 1
cctagtgtgt gctgcagaaa gagc                                           24

<210> SEQ ID NO 2
<211> LENGTH: 21
<212> TYPE: DNA
<213> ORGANISM: Artificial Sequence
<220> FEATURE:
<223> OTHER INFORMATION: Synthesized primer

<400> SEQUENCE: 2
gaggaagtct tcacgttgac g                                              21

<210> SEQ ID NO 3
<211> LENGTH: 22
<212> TYPE: DNA
<213> ORGANISM: Artificial Sequence
<220> FEATURE:
<223> OTHER INFORMATION: Synthesized primer

<400> SEQUENCE: 3
gcagctttga gatgacatca cc                                             22

<210> SEQ ID NO 4
<211> LENGTH: 21
<212> TYPE: DNA
<213> ORGANISM: Artificial Sequence
<220> FEATURE:
<223> OTHER INFORMATION: Synthesized primer

<400> SEQUENCE: 4
ctcagcctcc tcctttcac a                                               21

<210> SEQ ID NO 5
<211> LENGTH: 21
<212> TYPE: DNA
<213> ORGANISM: Artificial Sequence
<220> FEATURE:
<223> OTHER INFORMATION: Synthesized primer

<400> SEQUENCE: 5
aacctgatag acgacctgca g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthesized primer

<400> SEQUENCE: 6
gcttggacat gtccatctcc a                                              21

<210> SEQ ID NO 7
<211> LENGTH: 20
<212> TYPE: DNA
<213> ORGANISM: Artificial Sequence
<220> FEATURE:
<223> OTHER INFORMATION: Synthesized primer

<400> SEQUENCE: 7
ctacaggcct tgctcagctc                                                20
```

```
<210> SEQ ID NO 8
<211> LENGTH: 20
<212> TYPE: DNA
<213> ORGANISM: Artificial Sequence
<220> FEATURE:
<223> OTHER INFORMATION: Synthesized primer

<400> SEQUENCE: 8
agattgtggg cgtctgtagg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthesized primer

<400> SEQUENCE: 9
gaatgacgga cgcccagatg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthesized primer

<400> SEQUENCE: 10
actggcagcc acttgtaggg                                              20

<210> SEQ ID NO 11
<211> LENGTH: 23
<212> TYPE: DNA
<213> ORGANISM: Artificial Sequence
<220> FEATURE:
<223> OTHER INFORMATION: Synthesized primer

<400> SEQUENCE: 11
cctgagtcag cagattgaga aca                                          23

<210> SEQ ID NO 12
<211> LENGTH: 21
<212> TYPE: DNA
<213> ORGANISM: Artificial Sequence
<220> FEATURE:
<223> OTHER INFORMATION: Synthesized primer

<400> SEQUENCE: 12
ccagtactct ccgctcttcc a                                            21

<210> SEQ ID NO 13
<211> LENGTH: 21
<212> TYPE: DNA
<213> ORGANISM: Artificial Sequence
<220> FEATURE:
<223> OTHER INFORMATION: Synthesized primer

<400> SEQUENCE: 13
tctggtaaag aaggccctgt g                                            21

<210> SEQ ID NO 14
<211> LENGTH: 20
<212> TYPE: DNA
<213> ORGANISM: Artificial Sequence
<220> FEATURE:
<223> OTHER INFORMATION: Synthesized primer
```

<400> SEQUENCE: 14
gtccagggaa tccgatgttg					20

<210> SEQ ID NO 15
<211> LENGTH: 20
<212> TYPE: DNA
<213> ORGANISM: Artificial Sequence
<220> FEATURE:
<223> OTHER INFORMATION: Synthesized primer

<400> SEQUENCE: 15
aagagctatg agctgcctga					20

<210> SEQ ID NO 16
<211> LENGTH: 20
<212> TYPE: DNA
<213> ORGANISM: Artificial Sequence
<220> FEATURE:
<223> OTHER INFORMATION: Synthesized primer

<400> SEQUENCE: 16
tggcatagag gtctttacgg					20

<210> SEQ ID NO 17
<211> LENGTH: 20
<212> TYPE: DNA
<213> ORGANISM: Artificial Sequence
<220> FEATURE:
<223> OTHER INFORMATION: Synthesized primer

<400> SEQUENCE: 17
ttgcgtctac cccaacccag					20

<210> SEQ ID NO 18
<211> LENGTH: 20
<212> TYPE: DNA
<213> ORGANISM: Artificial Sequence
<220> FEATURE:
<223> OTHER INFORMATION: Synthesized primer

<400> SEQUENCE: 18
gccaccgttc atggtctctc					20

<210> SEQ ID NO 19
<211> LENGTH: 20
<212> TYPE: DNA
<213> ORGANISM: Artificial Sequence
<220> FEATURE:
<223> OTHER INFORMATION: Synthesized primer

<400> SEQUENCE: 19
gttgcagacc aggagcaatg					20

<210> SEQ ID NO 20
<211> LENGTH: 21
<212> TYPE: DNA
<213> ORGANISM: Artificial Sequence
<220> FEATURE:
<223> OTHER INFORMATION: Synthesized primer

<400> SEQUENCE: 20
tctctcggtc atgaaagtgg c					21

```
<210> SEQ ID NO 21
<211> LENGTH: 20
<212> TYPE: DNA
<213> ORGANISM: Artificial Sequence
<220> FEATURE:
<223> OTHER INFORMATION: Synthesized primer

<400> SEQUENCE: 21
ccaggctgcg gaggcaatca                                                     20

<210> SEQ ID NO 22
<211> LENGTH: 22
<212> TYPE: DNA
<213> ORGANISM: Artificial Sequence
<220> FEATURE:
<223> OTHER INFORMATION: Synthesized primer

<400> SEQUENCE: 22
ggccagctgc tctttcaggt cg                                                  22

<210> SEQ ID NO 23
<211> LENGTH: 20
<212> TYPE: DNA
<213> ORGANISM: Artificial Sequence
<220> FEATURE:
<223> OTHER INFORMATION: Synthesized primer

<400> SEQUENCE: 23
ttccctcgag caggcttcgg                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthesized primer

<400> SEQUENCE: 24
gccataggat ggcgctcggg                                                     20

<210> SEQ ID NO 25
<211> LENGTH: 20
<212> TYPE: DNA
<213> ORGANISM: Artificial Sequence
<220> FEATURE:
<223> OTHER INFORMATION: Synthesized primer

<400> SEQUENCE: 25
accgcaaaga gcacgagaag                                                     20

<210> SEQ ID NO 26
<211> LENGTH: 20
<212> TYPE: DNA
<213> ORGANISM: Artificial Sequence
<220> FEATURE:
<223> OTHER INFORMATION: Synthesized primer

<400> SEQUENCE: 26
accaacgtaa atcacacggc                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthesized primer
```

```
<400> SEQUENCE: 27
actgaggatg gcaagcaaca                                               20

<210> SEQ ID NO 28
<211> LENGTH: 20
<212> TYPE: DNA
<213> ORGANISM: Artificial Sequence
<220> FEATURE:
<223> OTHER INFORMATION: Synthesized primer

<400> SEQUENCE: 28
atttgtggaa acctcgggca                                               20

<210> SEQ ID NO 29
<211> LENGTH: 19
<212> TYPE: DNA
<213> ORGANISM: Artificial Sequence
<220> FEATURE:
<223> OTHER INFORMATION: Synthesized primer

<400> SEQUENCE: 29
ccgtcgtgga tctgacgtg                                                19

<210> SEQ ID NO 30
<211> LENGTH: 20
<212> TYPE: DNA
<213> ORGANISM: Artificial Sequence
<220> FEATURE:
<223> OTHER INFORMATION: Synthesized primer

<400> SEQUENCE: 30
gttgctgttg aagtcgcagg                                               20
```